United States Patent
Cariou et al.

(10) Patent No.: US 11,285,133 B2
(45) Date of Patent: Mar. 29, 2022

(54) 2- OR 3-IMIDAZOLINES AS CARBAPENEMASES INHIBITORS

(71) Applicants: Centre national de la recherche scientifique, Paris (FR); Université Paris-Sud, Orsay (FR); ASSISTANCE PUBLIQUE—HOPITAUX DE PARIS, Paris (FR)

(72) Inventors: Kevin Cariou, Paris (FR); Robert Dodd, Paris (FR); Eugénie Romero, Gif sur Yvette (FR); Mohamed Benchekroun, Brigthon (GB); Bogdan Iorga, Antony (FR); Thierry Naas, Clamart (FR); Saoussen Oueslati, Paris (FR)

(73) Assignees: CENTRE NATIONAL DE LA RECHERCHE SCIENTIFIQUE, Paris (FR); UNIVERSITÉ PARIS-SUD, Orsay (FR); ASSISTANCE PUBLIQUE—HOPITAUX DE PARIS, Paris (FR)

( * ) Notice: Subject to any disclaimer, the term of this patent is extended or adjusted under 35 U.S.C. 154(b) by 167 days.

(21) Appl. No.: 16/492,502

(22) PCT Filed: Mar. 8, 2018

(86) PCT No.: PCT/EP2018/055820
§ 371 (c)(1),
(2) Date: Sep. 9, 2019

(87) PCT Pub. No.: WO2018/162670
PCT Pub. Date: Sep. 13, 2018

(65) Prior Publication Data
US 2021/0128530 A1    May 6, 2021

(30) Foreign Application Priority Data
Mar. 9, 2017 (EP) ..................................... 17305257

(51) Int. Cl.
| | |
|---|---|
| *C07D 233/06* | (2006.01) |
| *A61K 31/4164* | (2006.01) |
| *A61K 47/55* | (2017.01) |
| *A61K 31/407* | (2006.01) |
| *C07D 233/22* | (2006.01) |
| *C07D 233/24* | (2006.01) |

(52) U.S. Cl.
CPC ........ *A61K 31/4164* (2013.01); *A61K 31/407* (2013.01); *A61K 47/552* (2017.08); *C07D 233/06* (2013.01); *C07D 233/22* (2013.01); *C07D 233/24* (2013.01)

(58) Field of Classification Search
CPC ..................................................... A61K 31/41
See application file for complete search history.

(56) References Cited

U.S. PATENT DOCUMENTS

| | | | |
|---|---|---|---|
| 2008/0015156 | A1 | 1/2008 | Udayampalayam et al. |
| 2008/0114015 | A1 | 5/2008 | Tepe |
| 2014/0057888 | A1 | 2/2014 | Udayampalayam et al. |

FOREIGN PATENT DOCUMENTS

| | | |
|---|---|---|
| JP | A-1993255330 | 10/1993 |
| WO | WO-2007133790 | 11/2007 |

OTHER PUBLICATIONS

Hui Chen et al., Org. Letters (2013) vol. 15(1) pp. 212-215.*
Venkatesan et al. (BioOrg & Med Chem'2004). pp. 5807-5817.*
Zhao et al. (BioOrg & Med Chem'2017)pp. 750-758.*
Vippagunta et al. (2001).*
International Search Report dated Apr. 20, 2018 in International Application No. PCT/EP2018/055820.

(Continued)

*Primary Examiner* — Paul V Ward
(74) *Attorney, Agent, or Firm* — B. Aaron Schulman, Esq.; Stites & Harbison, PLLC

(57) ABSTRACT

The present application relates to novel 3-imidazolines of formula (I') and (I) below: (I') (I) Wherein $Ar_1$, $Ar_2$, $Ar_3$, and $R_1$ to $R_6$ are as defined in the claims. The 3-imidazolines of the invention are useful in antibiotic therapies, in particular as inhibitors of carbapenemases. They are also useful as antibiotics themselves. The present invention also concerns a method for preparing more specifically the 3-imidazolines of formula (I). The present invention further relates to conjugates of said compounds with known antibiotics.

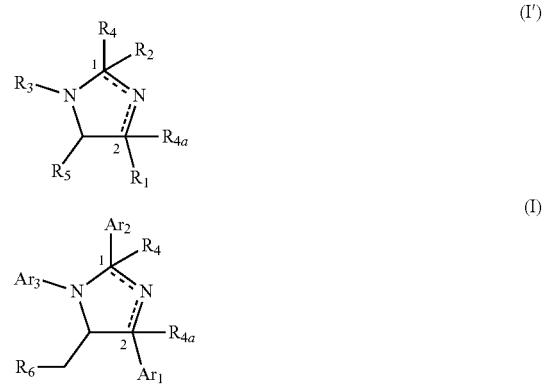

23 Claims, No Drawings

(56) References Cited

OTHER PUBLICATIONS

Chen, et al., "Copper-Catalyzed Aliphatic C—H Amination with an Amidine Moiety", 2013, pp. 212-215, vol. 15, No. 1, Organic Letters.
Aranapakam, et al., "Novel imidazole substituted 6-methylidene-penems as broad-spectrum β-lactamase inhibitors", 2004, pp. 5807-5817, vol. 12, Bioorganic & Medicinal Chemistry.
Zhao, et al., "Discovery of biphenyl imidazole derivatives as potent antifungal agents: Design, synthesis, and structure-activity relationship studies", Jan. 1, 2017, pp. 750-758, Bioorganic & Medicinal Chemistry, XP055465906.
Dabholkar, Vijay V. et al., "Chemistry of Novel Biphenyl Imidazole— Their Synthesis & Microbial Evaluation", Heterocyclic Letters, vol. 4: (2) 409-415 (2014).

* cited by examiner

2- OR 3-IMIDAZOLINES AS CARBAPENEMASES INHIBITORS

The present invention relates to 3-imidazoline derivatives, useful in antibiotic therapies, and methods for preparing same.

BACKGROUND

A recent report by the World Health Organization raises concerns as to the number of multidrug-resistant (i.e. resistant to several drugs and/or drug classes)—or even pandrug-resistant (i.e. resistant to all drugs and/or drug classes known to date) bacteria, which increases exponentially throughout the world. In particular, beta-lactams, which for some time were effective for fighting any infection, have become inefficient because bacteria have now developed new enzymatic resistance pathways.

beta-lactams, such as penicillins, cephalosporins, monobactams and carbapenems, contain a β-lactam moiety, which is the target of bacterial enzymes called beta-lactamases. Currently, beta-lactamase-mediated resistance does not spare even the newest and most powerful beta-lactams (carbapenems).

beta-lactamases act by opening the C(O)—N bond of the lactam ring, which is weakened by the delocalization of the non-binding electrons of the nitrogen adjacent to the carbonyl. The enzymatic mechanism may be explained as depicted on the scheme below:

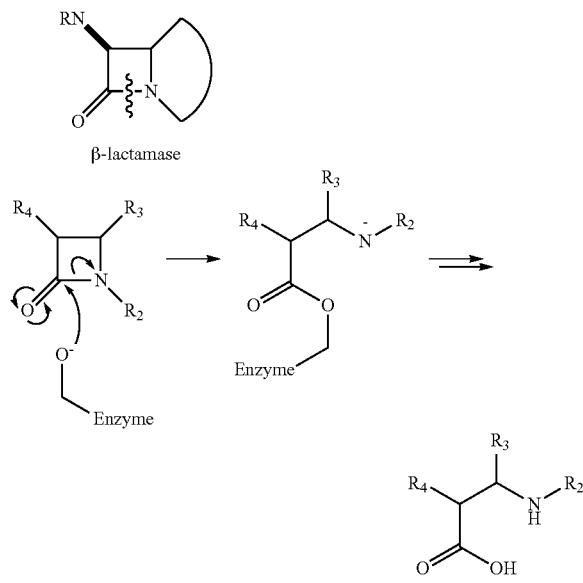

beta-lactamases are classified into four classes, namely classes A-D.

Carbapenemase are specific beta-lactamases, having the capacity to hydrolyze carbapenems. Carbapenemases are of two different types: Serine-beta-lactamases (SBLs, belonging to classes A and D beta-lactamases) and Metallo-beta-lactamases (MBLs, belonging to class B beta-lactamases). Class A carbapenemases include members of the SME, IMI, NMC, GES, and KPC families. The *Klebsiella pneumoniae* Carbapenemases (KPC) are the most prevalent, found mostly on plasmids (of *Klebsiella pneumoniae*). Class D carbapenemases consist of OXA-type beta-lactamases, frequently detected in *Acinetobacter baumannii*. Class B carbapenemases, which are metallo-beta-lactamases that contain zinc in the active site, include the NDM, IMP, VIM, SPM, GIM, and SIM families and have been primarily detected in *Pseudomonas aeruginosa* and have been increasingly reported in Enterobacteriaceae. In particular, antibiotic resistance of wide-spread bacteria such as *K. pneumoniae, E. coli* and *E. cloacae* involves several types of carbapenemases: class B metallo-enzyme NDM-1 (12%), class D oxacillinase OXA-48 (67%) and class A KPC-2 (14%).

Until recently, there were only three marketed class A beta-lactamase inhibitors: clavulanic acid, sulbactam and tazobactam. However, none of them were active on carbapenemases. Worth mentioning is a novel inhibitor avibactam, which inhibits class A carbapenemase (KPC) and some class D carbapenemases (OXA-48), and which has recently been commercialized in the US and in France, and Relebactam, another class A carbapenemase (KPC) inhibitor currently in a phase III clinical trial. Also, Nacubactam, Zidebactam, ETX-2514 are currently in phase I clinical trials, and Vaborbactam is undergoing phase III clinical trials. However, to date, there are no MBL (Metallo-beta-lactamase) inhibitors, nor carbapenemase pan-inhibitors (i.e. inhibiting all classes of carbapenemases, namely carbapenemases of classes A, B and D) approved by the Regulatory Authorities.

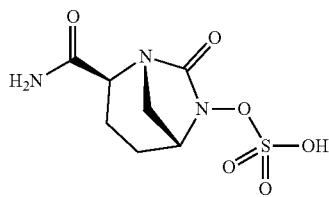

Avibactam

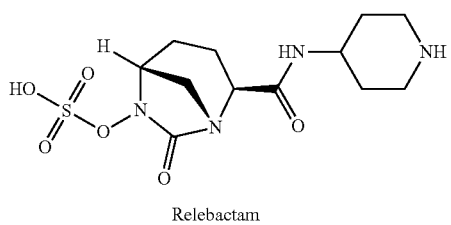

Relebactam

PCT application number EP2016/071115 (WO 2017/042233) discloses azetidinimines as carbapenemases inhibitors, in particular on class B, D and A beta-lactamases, specifically on metallo-enzyme NDM-1, oxacillinase OXA-48 and penicillinase KPC-2, respectively.

However, there is still a need for new carbapenemases inhibitors, and in particular carbapenemase pan-inhibitors (i.e. inhibiting all classes of carbapenemases, namely carbapenemases of classes A, B and D) with a different selectivity profile, such as class-A/B/D carbapenemase inhibitors.

SUMMARY OF THE INVENTION

Applicants surprisingly found that compounds containing a 3-imidazoline moiety were efficient as carbapenemases polyinhibitors, especially active on class A and B carbapenemases.

In a first aspect, the invention relates to a compound of formula (I), such as a compound of formula (Ia):

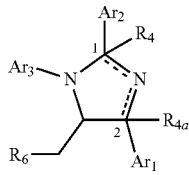

(I)

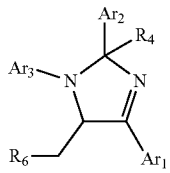

(Ia)

wherein
- ═══ represents a single or double bond, with the proviso that one of the two bonds
- ═══ is a single bond and the other is a double bond;
- $Ar_1$ and $Ar_2$ are identical or different and are independently a mono or polycyclic $C_5$-$C_{12}$ aryl or mono or polycyclic $C_3$-$C_{12}$ heteroaryl group,
- wherein the aryl or heteroaryl group is optionally substituted with:
  - one to three substituents independently selected from the group consisting of: a halogen atom, OH, $C_1$-$C_6$ alkyl, $C_3$-$C_7$ cycloalkyl, $C_1$-$C_6$ alkoxy, $C_3$-$C_7$ cycloalkoxy, nitro, cyano, formyl, amino-$C_1$-$C_{10}$ alkoxy, (carboxylic acid)-$C_1$-$C_{10}$ alkoxy, (carboxylic ($C_1$-$C_6$)alkyl ester)-$C_1$-$C_{10}$ alkoxy, (1,2 diol)-$C_2$-$C_{10}$ alkoxy, —O—($C_1$-$C_6$)alkyl-O—($C_1$-$C_6$)alkyl-OH, ($C_1$-$C_6$)-alkoxy-($C_1$-$C_6$)-alkyl, $C_2$-$C_6$ alkylcarbonyl, $C_1$-$C_6$ alkylthio, $C_1$—$O_6$ thioalkyl, ($C_1$-$C_6$)-alkyl-thio-($C_1$-$C_6$)-alkyl, $C_1$-$C_6$ alkylsulfinyl, $C_1$-$C_6$ alkylsulfonyl, $C_1$-$C_6$ haloalkyl, $C_1$-$C_6$ haloalkoxy, $C_1$-$C_6$ haloalkoxy alkyl, $C_2$-$C_6$ haloalkylcarbonyl, $C_1$-$C_6$ haloalkylthio, $C_1$-$C_6$ haloalkylsulfinyl, $C_1$-$C_6$ haloalkylsulfonyl, $C_2$-$C_6$ alkenyl, $C_2$-$C_6$ alkynyl, $C_2$-$C_6$ haloalkynyl, $C_2$-$C_6$ haloalkenyl, $C_2$-$C_6$ haloalkenyloxy, $C_2$-$C_6$ haloalkynyloxy, $C_2$-$C_6$ alkenyloxy, $C_2$-$C_6$ alkynyloxy, $C_2$-$C_6$ alkenylthio, $C_2$-$C_6$ alkynylthio, $C_2$-$C_6$ haloalkenylthio, $C_2$-$C_6$ haloalkynylthio and/or a $C_1$-$C_6$ alkoxy optionally substituted by a mono or polycyclic $C_5$-$C_{12}$ aryl group,
  - a mono or polycyclic $C_5$-$C_{12}$ aryl or mono or polycyclic $C_3$-$C_{12}$ heteroaryl group optionally substituted with a halogen atom, OH, $C_1$-$C_6$ alkyl, or $C_1$-$C_6$ alkoxy; and/or
  - a bridging group of formula O—$CH_2$—O— or O—$CH_2CH_2$—O—;
- $Ar_3$ is a mono or polycyclic $C_5$-$C_{12}$ aryl group or mono or polycyclic $C_3$-$C_{12}$ heteroaryl group, optionally substituted with substituents independently selected from the group consisting of:
  - halogen atoms, OH, $C_1$-$C_6$ alkyl, $C_3$-$C_7$ cycloalkyl, $C_1$-$C_6$ alkoxy, $C_3$-$C_7$ cycloalkoxy, cyano, formyl, nitro, $C_1$-$C_6$ alkyl, $C_3$-$C_7$ cycloalkyl, $C_1$-$C_6$ alkoxy, ($C_1$-$C_6$)-alkoxy-($C_1$-$C_6$)-alkyl, $C_2$-$C_6$ alkylcarbonyl, $C_1$-$C_6$ alkylthio, $C_1$-$C_6$ thioalkyl, ($C_1$-$C_6$)-alkylthio-($C_1$-$C_6$)-alkyl, $C_1$-$C_6$ alkylsulfinyl, $C_1$-$C_6$ alkylsulfonyl, $C_1$-$C_6$ haloalkyl, $C_1$-$C_6$ haloalkoxy, $C_1$-$C_6$ haloalkoxy alkyl, $C_2$-$C_6$ haloalkylcarbonyl, $C_1$-$C_6$ haloalkylthio, $C_1$-$C_6$ haloalkylsulfinyl, $C_1$-$C_6$ haloalkylsulfonyl, $C_2$-$C_6$ alkenyl, $C_2$-$C_6$ alkynyl, $C_2$-$C_6$ haloalkynyl, $C_2$-$C_6$ haloalkenyl, $C_2$-$C_6$ haloalkenyloxy, $C_2$-$C_6$ haloalkynyloxy, $C_2$-$C_6$ alkenyloxy, $C_2$-$C_6$ alkynyloxy, $C_2$-$C_6$ alkenylthio, $C_2$-$C_6$ alkynylthio, $C_2$-$C_6$ haloalkenylthio, $C_2$-$C_6$ haloalkynylthio group, and/or a monocyclic $C_5$-$C_6$ aryl group optionally substituted by a $C_1$-$C_6$ alkyloxy group,
  - a mono or polycyclic $C_5$-$C_{12}$ aryl or mono or polycyclic $C_3$-$C_{12}$ heteroaryl group optionally substituted with a halogen atom, OH, $C_1$-$C_6$ alkyl, or $C_1$-$C_6$ alkoxy; and/or
  - a bridging group of formula O—$CH_2$—O— or O—$CH_2CH_2$—O—;
- $R_4$ is present when the bond ═══ between the carbon 1 and the nitrogen atom is a single bond and is absent when the bond ═══ between the carbon 1 and the nitrogen atom is a double bond;
- $R_{4a}$ is present when the bond ═══ between the carbon 2 and the nitrogen atom is a single bond and is absent when the bond ═══ between the carbon 2 and the nitrogen atom is a double bond;
- $R_4$ is a hydrogen atom or a $C_1$-$C_6$ alkyl group optionally substituted with substituents independently selected from the group consisting of: halogen atoms, hydroxyl (OH), nitro, cyano, formyl, $C_3$-$C_7$ cycloalkyl, $C_1$-$C_6$-alkoxy, amino, $C_1$-$C_6$ alkylamino, di($C_1$-$C_6$)alkylamino, COOH, COO—($C_1$-$C_6$)alkyl, $CONH_2$, CONH ($C_1$-$C_6$)alkyl, $C_1$-$C_6$ thioalkyl, SH, S($C_1$-$C_6$)alkyl, S(O) ($C_1$-$C_6$)alkyl, S($O_2$)($C_1$-$C_6$)alkyl, a mono or polycyclic $C_5$-$C_{12}$ aryl group;
- $R_{4a}$ is a hydrogen atom or a $C_1$-$C_6$ alkyl group optionally substituted with substituents independently selected from the group consisting of: halogen atoms, hydroxyl (OH), oxo (═O), nitro, cyano, formyl, $C_3$-$C_7$ cycloalkyl, $C_1$-$C_6$-alkoxy, amino, arylimido optionally substituted, $C_1$-$C_6$ alkylamino, di($C_1$-$C_6$)alkylamino, COOH, COO—($C_1$-$C_6$)alkyl, $CONH_2$, CONH($C_1$-$C_6$)alkyl, $C_1$-$C_6$ thioalkyl, SH, S($C_1$-$C_6$)alkyl, S(O)($C_1$-$C_6$)alkyl, S($O_2$)($C_1$-$C_6$)alkyl, a mono or polycyclic $C_5$-$C_{12}$ aryl group;
- $R_6$ is a hydrogen atom, a halogen atom, a cyano, $C_1$-$C_{10}$ alkyl, $C_3$-$C_{10}$ cycloalkyl, $C_1$-$C_{10}$ alkoxy, $C_1$-$C_{10}$ haloalkoxy, ($C_1$-$C_6$)-alkoxy-($C_1$-$C_6$)-alkyl, ($C_1$-$C_6$)-haloalkoxy-($C_1$-$C_6$)-alkyl, $C_1$-$C_{10}$ thioalkyl, ($C_1$-$C_6$)-alkylthio-($C_1$-$C_6$)-alkyl, $C_1$-$C_{10}$ alkylsulfinyl, $C_1$-$C_{10}$ haloalkylsulfinyl, $C_1$-$C_{10}$ haloalkylsulfonyl, $C_1$-$C_{10}$ alkylsulfonyl, $C_5$-$C_{12}$ arylsulfonyl, formyl, $C_2$-$C_{10}$ alkylcarbonyl, $C_2$-$C_{10}$ alkenyl, $C_2$-$C_{10}$ alkynyl, $C_2$-$C_{10}$ alkenyloxy, $C_2$-$C_{10}$ alkynyloxy, $C_2$-$C_{10}$ alkenylthio, $C_2$-$C_{10}$ alkynylthio, $C_1$-$C_{10}$ haloalkyl, $C_2$-$C_{10}$ haloalkenyl, $C_2$-$C_{10}$ haloalkynyl, $C_2$-$C_{10}$ haloalkylcarbonyl, $C_1$-$C_{10}$ haloalkylthio, $C_2$-$C_{10}$ haloalkenyloxy, $C_2$-$C_{10}$ haloalkynyloxy, $C_2$-$C_{10}$ haloalkenylthio, $C_2$-$C_{10}$ haloalkynylthio, ($C_5$-$C_{12}$)-aryl-($C_1$-$C_6$)-alkyl, ($C_5$-$C_{12}$)-aryl-($C_1$-$C_6$)-alkyl ester or a mono or polycyclic $C_5$-$C_{12}$ aryl or mono or polycyclic $C_3$-$C_{12}$ heteroaryl group, each group being optionally substituted with substituents independently selected from the group consisting of: halogen atoms, hydroxyl (OH), nitro, cyano, formyl, $C_3$-$C_7$ cycloalkyl, $C_1$-$C_6$-alkoxy, amino, $C_1$-$C_6$ alkylamino, di($C_1$-$C_5$)alkylamino, COOH, COO—($C_1$-$C_5$)alkyl, $CONH_2$, CONH($C_1$-$C_5$)alkyl, $C_1$-$C_6$ thioalkyl, SH, S($C_1$-$C_5$)alkyl, S(O)($C_1$-$C_5$)alkyl, S($O_2$)($C_1$-$C_6$)alkyl, a mono or polycyclic $C_5$-$C_{12}$ aryl group, a solvate or a salt thereof.

In a particular aspect, the compound of formula (I) is a compound of formula (Ia) or (Ib):

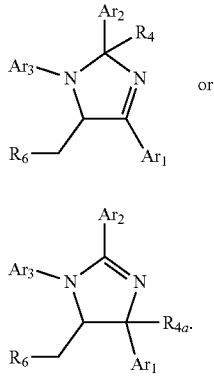
(Ia)

(Ib)

In another aspect, the present invention concerns a method for preparing a compound of formula (I) as defined above, comprising the following successive steps:

a) a compound of formula (II):

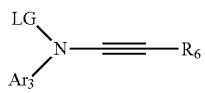
(II)

with $Ar_3$ and $R_6$ as defined above and LG a leaving group, is added to a compound of formula (III):

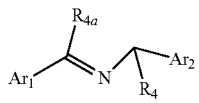
(III)

with $Ar_1$, $Ar_2$ and $R_4$ as defined above, in the presence of a base;

b) isolating the compound of formula (I) as defined above.

In a particular aspect, the compound of formula (III) is a compound of formula (IIIa) to prepare a compound of formula (Ia) or is a compound of formula (IIIb) to prepare a compound of formula (Ib):

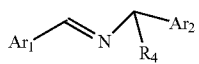
(IIIa)

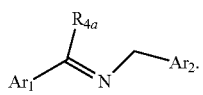
(IIIb)

In another aspect, the present invention relates to a compound of formula (I'), such as a compound of formula (I'a):

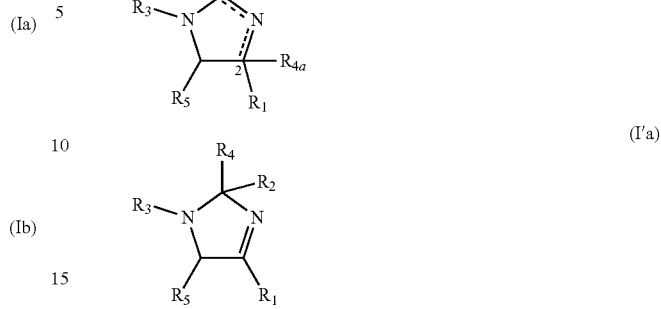
(I')

(I'a)

wherein

=== represents a single or double bond, with the proviso that one of the two bonds === is a single bond and the other is a double bond;

$R_1$, $R_2$, and $R_3$ are identical or different, and are independently from each other a hydrogen, halogen, nitro, cyano, formyl, $C_1$-$C_{10}$ alkyl, $C_3$-$C_{10}$ cycloalkyl, 3- to 8-membered heterocycle, $C_1$-$C_{10}$ alkoxy, $C_2$-$C_{10}$ alkylcarbonyl, a $C_6$-$C_{13}$ arylcarbonyl, a $C_4$-$C_{13}$ heteroaryl carbonyl, $C_1$-$C_{10}$ haloalkoxy, ($C_1$-$C_6$)-alkoxy-($C_1$-$C_6$)-alkyl, ($C_1$-$C_6$)-haloalkoxy-($C_1$-$C_6$)-alkyl, $C_1$-$C_{10}$ thioalkyl, ($C_5$-$C_{12}$)-aryl-($C_1$-$C_6$)-alkyl ester, ($C_1$-$C_6$)-alkylthio-($C_1$-$C_6$)-alkyl, $C_1$-$C_{10}$ alkylsulfinyl, $C_1$-$C_{10}$ haloalkylsulfinyl, $C_1$-$C_{10}$ haloalkylsulfonyl, $C_1$-$C_{10}$ alkylsulfonyl, $C_5$-$C_{12}$ arylsulfonyl, $C_2$-$C_{10}$ alkenyl, $C_2$-$C_{10}$ alkynyl, $C_2$-$C_{10}$ alkenyloxy, $C_2$-$C_{10}$ alkynyloxy, $C_2$-$C_{10}$ alkenylthio, $C_2$-$C_{10}$ alkynylthio, $C_1$-$C_{10}$ haloalkyl, $C_2$-$C_{10}$ haloalkenyl, $C_2$-$C_{10}$ haloalkynyl, $C_2$-$C_{10}$ haloalkylcarbonyl, $C_1$-$C_{10}$ haloalkylthio, $C_2$-$C_{10}$ haloalkenyloxy, $C_2$-$C_{10}$ haloalkynyloxy, $C_2$-$C_{10}$ haloalkenylthio, $C_2$-$C_{10}$ haloalkynylthio, ($C_5$-$C_{12}$)-aryl-($C_1$-$C_6$)-alkyl, a ($C_1$-$C_6$)alkyl-($C_5$-$C_{12}$)aryl, a ($C_1$-$C_6$)alkyl-($C_5$-$C_{12}$)heteroaryl, a mono or polycyclic $C_5$-$C_{12}$ aryl or mono or polycyclic $C_3$-$C_{12}$ heteroaryl fragments, wherein the $C_1$-$C_{10}$ alkyl, $C_3$-$C_{10}$ cycloalkyl, 3- to 8-membered heterocycle, $C_1$-$C_{10}$ alkoxy, $C_2$-$C_{10}$ alkylcarbonyl, a $C_6$-$C_{13}$ arylcarbonyl, a $C_4$-$C_{13}$ heteroaryl carbonyl, $C_1$-$C_{10}$ haloalkoxy, ($C_1$-$C_6$)-alkoxy-($C_1$-$C_6$)-alkyl, ($C_1$-$C_6$)-haloalkoxy-($C_1$-$C_6$)-alkyl, $C_1$-$C_{10}$ thioalkyl, ($C_5$-$C_{12}$)-aryl-($C_1$-$C_6$)-alkyl ester, ($C_1$-$C_6$)-alkylthio-($C_1$-$C_6$)-alkyl, $C_1$-$C_{10}$ alkylsulfinyl, $C_1$-$C_{10}$ haloalkylsulfinyl, $C_1$-$C_{10}$ haloalkylsulfonyl, $C_1$-$C_{10}$ alkylsulfonyl, $C_5$-$C_{12}$ arylsulfonyl, $C_2$-$C_{10}$ alkenyl, $C_2$-$C_{10}$ alkynyl, $C_2$-$C_{10}$ alkenyloxy, $C_2$-$C_{10}$ alkynyloxy, $C_2$-$C_{10}$ alkenylthio, $C_2$-$C_{10}$ alkynylthio, $C_1$-$C_{10}$ haloalkyl, $C_2$-$C_{10}$ haloalkenyl, $C_2$-$C_{10}$ haloalkynyl, $C_2$-$C_{10}$ haloalkylcarbonyl, $C_1$-$C_{10}$ haloalkylthio, $C_2$-$C_{10}$ haloalkenyloxy, $C_2$-$C_{10}$ haloalkynyloxy, $C_2$-$C_{10}$ haloalkenylthio, $C_2$-$C_{10}$ haloalkynylthio, ($C_5$-$C_{12}$)-aryl-($C_1$-$C_6$)-alkyl, a ($C_1$-$C_6$)alkyl-($C_5$-$C_{12}$)aryl, a ($C_1$-$C_6$)alkyl-($C_5$-$C_{12}$)heteroaryl, a mono or polycyclic $C_5$-$C_{12}$ aryl or mono or polycyclic $C_3$-$C_{12}$ heteroaryl fragment is optionally substituted with:

one or several (1 to 3) halogen atoms, hydroxyl (OH), nitro, cyano, formyl, $C_1$-$C_6$ alkyl, $C_3$-$C_7$ cycloalkyl, 3- to 8-membered heterocycle, amino-$C_1$-$C_{10}$ alkoxy, (carboxylic acid)-$C_1$-$C_{10}$ alkoxy, (carboxylic ($C_1$-$C_6$)alkyl ester)-$C_1$-$C_{10}$ alkoxy, (1,2 diol)-$C_2$-$C_{10}$ alkoxy, —O—($C_1$-$C_6$)alkyl-O—($C_1$-$C_6$)alkyl-OH, ($C_1$-$C_6$)-alkoxy-($C_1$-$C_6$)-alkyl, $C_2$-$C_6$ alkylcarbonyl, $C_1$-$C_6$ alkylthio, $C_1$-$C_6$ thioalkyl, ($C_1$-$C_6$)-alkylthio-($C_1$-$C_6$)-alkyl, $C_1$-$C_6$ alkylsulfinyl, $C_1$-$C_6$ alkylsulfonyl, $C_1$-$C_6$ haloalkyl, $C_1$-$C_6$ haloalkoxy, $C_1$-$C_6$ haloalkoxy alkyl, $C_2$-$C_6$ haloalkylcarbonyl, $C_1$-$C_6$ haloalkylthio, $C_1$-$C_6$ haloalkylsulfinyl, $C_1$-$C_6$ haloalkylsulfonyl, $C_2$-$C_6$ alkenyl, $C_2$-$C_6$ alkynyl, $C_2$-$C_6$ haloalkynyl, $C_2$-$C_6$ haloalkenyl, $C_2$-$C_6$ haloalkenyloxy, $C_2$-$C_6$ haloalkynyloxy, $C_2$-$C_6$ alkenyloxy, $C_2$-$C_6$ alkynyloxy, $C_2$-$C_6$ alkenylthio, $C_2$-$C_6$ alkynylthio, $C_2$-$C_6$ haloalkenylthio, $C_2$-$C_6$ haloalkynylthio and/or a $C_1$-$C_6$ alkoxy optionally substituted by a mono or polycyclic $C_5$-$C_{12}$ aryl group, a mono or polycyclic $C_5$-$C_{12}$ aryl or mono or polycyclic $C_3$-$C_{12}$ heteroaryl group optionally substituted with a halogen atom, OH, $C_1$-$C_6$ alkyl, or $C_1$-$C_6$ alkoxy; and/or a bridging group of formula O—$CH_2$—O— or O—$CH_2CH_2$—O— (the bridging group is in particular contemplated when the fragment contains an aryl or heteroaryl moiety, i.e. when it is a $C_6$-$C_{13}$ arylcarbonyl, a $C_4$-$C_{13}$ heteroaryl carbonyl, ($C_5$-$C_{12}$)-aryl-($C_1$-$C_6$)-alkyl ester, $C_5$-$C_{12}$ arylsulfonyl, ($C_5$-$C_{12}$)-aryl-($C_1$-$C_6$)-alkyl, a ($C_1$-$C_6$)alkyl-($C_5$-$C_{12}$)aryl, a ($C_1$-$C_6$)alkyl-($C_5$-$C_{12}$)heteroaryl, a mono or polycyclic $C_5$-$C_{12}$ aryl or mono or polycyclic $C_3$-$C_{12}$ heteroaryl fragment);

$R_4$ is present when the bond ≡≡≡ between the carbon 1 and the nitrogen atom is a single bond and is absent when the bond ≡≡≡ between the carbon 1 and the nitrogen atom is a double bond;

$R_{4a}$ is present when the bond ≡≡≡ between the carbon 2 and the nitrogen atom is a single bond and is absent when the bond ≡≡≡ between the carbon 2 and the nitrogen atom is a double bond;

$R_4$ is a hydrogen atom or a $C_1$-$C_6$ alkyl group optionally substituted with substituents independently selected from the group consisting of: halogen atoms, hydroxyl (OH), nitro, cyano, formyl, $C_3$-$C_7$ cycloalkyl, 3- to 8-membered heterocycle, $C_1$-$C_6$-alkoxy, amino, $C_1$-$C_6$ alkylamino, di($C_1$-$C_6$)alkylamino, COOH, COO—($C_1$-$C_6$)alkyl, $CONH_2$, CONH($C_1$-$C_6$)alkyl, $C_1$-$C_6$ thioalkyl, SH, S($C_1$-$C_6$)alkyl, S(O)($C_1$-$C_6$)alkyl, $S(O_2)$($C_1$-$C_6$)alkyl, a mono or polycyclic $C_5$-$C_{12}$ aryl group;

$R_{4a}$ is a hydrogen atom or a $C_1$-$C_6$ alkyl group optionally substituted with substituents independently selected from the group consisting of: halogen atoms, hydroxyl (OH), oxo (=O), nitro, cyano, formyl, $C_3$-$C_7$ cycloalkyl, $C_1$-$C_6$-alkoxy, amino, arylimido optionally substituted, $C_1$-$C_6$ alkylamino, di($C_1$-$C_6$)alkylamino, COOH, COO—($C_1$-$C_6$)alkyl, $CONH_2$, CONH($C_1$-$C_6$)alkyl, $C_1$-$C_6$ thioalkyl, SH, S($C_1$-$C_6$)alkyl, S(O)($C_1$-$C_6$)alkyl, $S(O_2)$($C_1$-$C_6$)alkyl, a mono or polycyclic $C_5$-$C_{12}$ aryl group;

$R_5$ is a hydrogen atom, a halogen atom, a cyano, $C_1$-$C_{10}$ alkyl, $C_3$-$C_{10}$ cycloalkyl, 3- to 8-membered heterocycle, $C_1$-$C_{10}$ alkoxy, $C_1$-$C_{10}$ haloalkoxy, ($C_1$-$C_6$)-alkoxy-($C_1$-$C_6$)-alkyl, ($C_1$-$C_6$)-haloalkoxy-($C_1$-$C_6$)-alkyl, $C_1$-$C_{10}$ thioalkyl, ($C_1$-$C_6$)-alkylthio-($C_1$-$C_6$)-alkyl, $C_1$-$C_{10}$ alkylsulfinyl, $C_1$-$C_{10}$ haloalkylsulfinyl, $C_1$-$C_{10}$ haloalkylsulfonyl, $C_1$-$C_{10}$ alkylsulfonyl, $C_5$-$C_{12}$ arylsulfonyl, formyl, $C_2$-$C_{10}$ alkylcarbonyl, $C_2$-$C_{10}$ alkenyl, $C_2$-$C_{10}$ alkynyl, $C_2$-$C_{10}$ alkenyloxy, $C_2$-$C_{10}$ alkynyloxy, $C_2$-$C_{10}$ alkenylthio, $C_2$-$C_{10}$ alkynylthio, $C_1$-$C_{10}$ haloalkyl, $C_2$-$C_{10}$ haloalkenyl, $C_2$-$C_{10}$ haloalkynyl, $C_2$-$C_{10}$ haloalkylcarbonyl, $C_1$-$C_{10}$ haloalkylthio, $C_2$-$C_{10}$ haloalkenyloxy, $C_2$-$C_{10}$ haloalkynyloxy, $C_2$-$C_{10}$ haloalkenylthio, $C_2$-$C_{10}$ haloalkynylthio, ($C_5$-$C_{12}$)-aryl-($C_1$-$C_6$)-alkyl, ($C_5$-$C_{12}$)-aryl-($C_1$-$C_6$)-alkyl ester, a ($C_1$-$C_6$)alkyl-($C_5$-$C_{12}$)aryl, a ($C_1$-$C_6$)alkyl-($C_5$-$C_{12}$) heteroaryl, a $C_5$-$C_{12}$ aryl or a $C_3$-$C_{12}$ heteroaryl group, each group being optionally substituted with substituents independently selected from the group consisting of: halogen atoms, hydroxyl (OH), nitro, cyano, formyl, $C_3$-$C_7$ cycloalkyl, $C_1$-$C_6$-alkoxy, amino, $C_1$-$C_6$ alkylamino, di($C_1$-$C_6$)alkylamino, COOH, COO—($C_1$-$C_6$)alkyl, $CONH_2$, CONH($C_1$-$C_6$)alkyl, $C_1$-$C_6$ thioalkyl, SH, S($C_1$-$C_6$)alkyl, S(O)($C_1$-$C_6$)alkyl, $S(O_2)$($C_1$-$C_6$)alkyl, a mono or polycyclic $C_5$-$C_{12}$ aryl group, or a compound of formula (I) as defined above for use as an inhibitor of a carbapenemase enzyme, in particular a carbapenemase of class A, B and/or D, preferably of a NDM-1 type, OXA-48 type or a KPC-type enzymes.

In a particular aspect, the compound of formula (I') is a compound of formula (I'a) or (I'b):

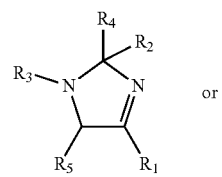

(I'a)

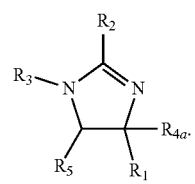

(I'b)

In another aspect, the present invention relates to a conjugate of a compound of formula (I) or (I') with an antibiotic, in particular for use as a simultaneous inhibitor of a penicillin-binding protein (i.e. as antibiotic) and of a carbapenemase enzyme, in particular a carbapenemase of class A, B and/or D, preferably of a NDM-1-type, OXA-48-type or a KPC-type enzymes.

In another aspect, the present invention relates to a conjugate of a compound of formula (I) or (I') with an antibiotic, typically an antibiotic containing a beta-lactam moiety.

In another aspect, the present invention relates to a compound of formula (I') or (I) as defined above or a conjugate thereof with an antibiotic, for use as drug.

In another aspect, the present invention relates to a pharmaceutical composition comprising at least one compound of formula (I) or (I') as defined above, or a conjugate thereof with an antibiotic, and a pharmaceutically acceptable carrier, in particular for use as drug.

In another aspect, the present invention relates to a kit comprising:
   at least one first container containing a first therapeutically active compound of formula (I) or (I') as defined above or a conjugate thereof with an antibiotic, and mixtures thereof, and
   at least one second container containing a second therapeutically active substance which is an antibiotic,
as a combination product for simultaneous, sequential or separate use, in particular in antibiotherapy.

Definitions

As understood herein, "mixtures of enantiomers" means any mixture of enantiomers. The mixtures can be racemic, i.e. 50/50% of each enantiomer by weight (w/w), or non-racemic, i.e. enriched in one or the other of the enantiomer so that the weight ratio (w/w) is between 50/50% and 75/25%, between 75/25% and 90/10% or above 95% of one enantiomer in comparison with the other. Typically, the compounds of the invention are either racemic or over 95%, preferably over 96%, preferably over 97%, preferably over 98%, even more preferably over 99%.

As understood herein, "mixtures of diastereomers" means any mixture of diastereoisomers in any proportions.

As customary in the art, in the present invention, "Me" stands for methyl (—CH$_3$), Bn stands for benzyl (—CH$_2$—C$_6$H$_5$) and Ph stands for phenyl (—C$_6$H$_5$).

The expressions "C$_1$-C$_{10}$ alkyl"/"alkyl" (i.e. the number of carbons in "alkyl" are not explicitly given) in the present invention mean a linear or branched saturated aliphatic group with 1 to 10 carbon atoms if not otherwise specified. An alkyl group covered by the scope of the present invention is for example a group chosen from methyl, ethyl, propyl, isopropyl, butyl, tert-butyl, isobutyl, n-pentyl, n-hexyl, etc.

The expressions "C$_3$-C$_{10}$ cycloalkyl"/"cycloalkyl" (i.e. the number of carbons in "cycloalkyl" are not explicitly given) in the present invention mean a cyclic alkyl group with 3 to 10 carbon atoms if not otherwise specified. A cycloalkyl group covered by the scope of the present invention is for example a group chosen from cyclopropyl, cyclobutyl, cyclopentyl, cyclohexyl, methylcyclohexyl, etc.

As used herein, a "3- to 8-membered heterocycle" is understood as a saturated or partially unsaturated 3- to 8-membered ring comprising 1 or 2 heteroatoms in the ring atoms selected from the group consisting of O, N (or NH where appropriate), S, S(O), and S(O)$_2$, the other ring atoms being carbon atoms. Examples of 3- to 8-membered heterocycles include epoxide, aziridine, oxetane, azetidine, thiethane, thiethane oxide, thiethane dioxide, pyrrolidine, tetrahydrofurane, dihydrofurane, tetrahydrothiophene, dihydrothiophene, piperidine, morpholine, thioxane, piperazine, etc. . . . . Preferably, the 3- to 8-membered heterocycle is a 3- to 6-heterocycle.

The expression "C$_1$-C$_{10}$ thioalkyl" in the present invention means a C$_1$-C$_{10}$ alkyl moiety as presently defined, substituted by a thiol group, i.e. SH or a salt thereof.

The expression "C$_1$-C$_6$ alkylthio" in the present invention represents a "(C$_1$-C$_6$ alkyl)-S—" group, i.e. an alkyl moiety with 1 to 6 carbon atoms, if not otherwise specified, as defined above linked to the rest of the molecule by a sulfur atom.

The expression "(C$_1$-C$_6$)-alkylthio-(C$_1$-C$_6$)-alkyl" in the present invention represents a "(C$_1$-C$_6$)-alkylthio" as presently defined linked by its sulfur atom to any carbon atom of a "C$_1$-C$_6$ alkyl" as defined presently.

The expressions "C$_1$-C$_{10}$ alkoxy"/"C$_1$-C$_{10}$ alkyloxy" represent a "(C$_1$-C$_6$ alkyl)-O—" group, i.e. an alkyl moiety with 1 to 10 carbon atoms, if not otherwise specified, as defined above, linked to the rest of the molecule by an oxygen atom. Examples of alkoxy groups covered by the scope of the present invention are methoxy, ethoxy groups etc.

The expression "(1,2 diol)-C$_2$-C$_{10}$ alkoxy" in the present invention represents an alkoxy group as defined above, wherein two adjacent carbon atoms are each linked to a hydroxyl group. The "1,2" does not limit the position to the first and second carbon atom attached to the rest of the molecule. Indeed, it is meant in the general context of the present invention that the hydroxyl groups are linked to two adjacent carbon, such as in position 2,3; 3,4; 4,5 . . . i.e. "n, n+1" wherein n is the position on the alkyl moiety, and thus n+1 cannot be superior to the total number of carbon atoms.

The expression "(carboxylic acid)-C$_1$-C$_{10}$ alkoxy" in the present invention represents an alkoxy group as defined above, wherein at least one carbon atom is linked to a fragment "COOH", "COO$^-$" or a salt thereof. Preferably, the "COOH" or "COO—" group or salt thereof is linked to the last carbon of the main linear chain of said C$_1$-C$_{10}$ alkoxy group.

The expression "(carboxylic (C$_1$-C$_6$)alkyl ester)-C$_1$-C$_{10}$ alkoxy" in the present invention represents an alkoxy group as defined above, wherein at least one carbon atom is linked to a carboxylic ester group of formula —COO—(C$_1$-C$_6$) alkyl, through the carboxylic group. Preferably, the carboxylic ester group is linked to the last carbon of the main linear chain of said C$_1$-C$_{10}$ alkoxy group.

The expression "C$_1$-C$_6$ NH$_2$-substituted alkyl" in the present invention represents an alkyl group as defined above, wherein at least one carbon atom is substituted by an amino (NH$_2$) group. Preferably, the N$_3$ group is linked to the last carbon of the main linear chain of said C$_1$-C$_6$ alkyl group.

The expression "C$_1$-C$_{10}$ alkylsulfinyl" in the present invention represents a "(C$_1$-C$_{10}$ alkyl)-S(=O)—", i.e. an alkyl moiety of 1 to 10 carbon atoms, if not otherwise specified, as defined above, linked to the rest of the molecule by a sulphur atom which is mono oxidised.

The expression "C$_1$-C$_{10}$ alkylsulfonyl" in the present invention represents a "(C$_1$-C$_{10}$ alkyl)-S(=O)$_2$—", i.e. an alkyl moiety of 1 to 10 carbon atoms, if not otherwise specified, as defined above, linked to the rest of the molecule by a sulphur atom which is oxidised twice.

The expression "(C$_1$-C$_6$)-alkoxy-(C$_1$-C$_6$)-alkyl" in the present invention represents a "(C$_1$-C$_6$)-alkoxy" as defined above linked by its oxygen atom to any carbon atom of a "C$_1$-C$_6$ alkyl" group as defined above, the latter alkyl moiety being linked to the rest of the molecule.

The term "formyl" in the present invention represents a H—C(=O)— group.

The expression "C$_2$-C$_{10}$ alkylcarbonyl" in the present invention means an alkyl group as presently defined linked to a carbonyl, the carbonyl being itself linked to the rest of the molecule (e.g. of formula (I)).

The expressions "C$_5$-C$_{12}$ aryl"/"aryl" (i.e. the number of carbons in "aryl" are not explicitly given) in the present invention mean a cyclic (mono- or polycyclic) aromatic group comprising between 5 and 12 carbon atoms if not otherwise specified. Examples of aryl groups covered by the scope of the present invention are phenyl, naphthyl, etc.

The expression "monocyclic C$_5$-C$_{12}$ aryl" in the present invention represents an aryl fragment as defined here-above with only one hydrocarbon ring such as a phenyl fragment.

The expression "polycyclic C$_5$-C$_{12}$ aryl" in the present invention represents an aryl fragment as defined above with more than one hydrocarbon ring such as a naphthalene, anthracene, or a phenanthrene fragment.

The expression "heteroaryl" in the present invention means a cyclic (mono- or polycyclic) aromatic group comprising between 5 and 12 atoms which can be carbon atoms and/or heteroatoms such as nitrogen, oxygen or sulphur (e.g. the heteroaryl can comprise between 3 to 9 carbon atoms and between 1 and 5 heteroatoms). Examples of heteroaryl groups covered by the scope of the present invention are pyridine, thiophene, thiazole, imidazole, pyrazole, pyrrole, quinoline, indole, pyridazine, quinoxaline, dihydrobenzofuran etc.

The expression "monocyclic $C_5$-$C_{12}$ heteroaryl" in the present invention represents a heteroaryl fragment as defined here-above with only one multi-atom ring such as a pyridyl, thiazole, imidazole, etc. fragment.

The expression "polycyclic $C_5$-$C_{12}$ heteroaryl" in the present invention represents a heteroaryl fragment as defined above with more than one multi-atom ring such as a quinoline, indole, quinoxaline, etc. fragment.

As used herein, an "aryl or heteroaryl substituted by a bridging group" is understood as an aryl or heteroaryl group wherein the bridging group substitutes two carbons, preferably two adjacent carbons, of the aryl or heteroaryl, and forms together with said aryl or heteroaryl a fused polycyclic group. For instance, if the aryl or heteroaryl is monocyclic, then said monocyclic aryl or heteroaryl substituted by a bridging group is a fused bicyclic group. In general, the bridging group substitutes two adjacent atoms on the aryl (or heteroaryl) group. Examples of such aryl or heteroaryl substituted by a bridging group include 1,3-benzodioxole and 1,4-benzodioxane.

The expression "$(C_5$-$C_{12})$-aryl-$(C_1$-$C_6)$-alkyl" in the present invention represents a "$(C_5$-$C_{12})$-aryl" as defined above linked to any carbon atom of a "$C_1$-$C_6$ alkyl" group as defined above, the alkyl moiety being linked to the rest of the molecule.

The expression "$C_5$-$C_{12}$ arylsulfonyl" in the present invention represents a "$(C_5$-$C_{12}$ aryl)-S($=$O)$_2$—", i.e. an aryl moiety of 5 to 12 carbon atoms as defined above linked to a sulphur atom which is oxidised twice.

The expression "arylimido" in the present invention represents a group of formula $=$N—Ar with Ar representing an aryl group as defined above.

The expressions "$C_2$-$C_{10}$ alkenyl"/"alkenyl" (i.e. the number of carbons in "alkenyl" are not explicitly given) in the present invention mean a cyclic, linear or branched aliphatic group with 2 to 10 carbon atoms, if not otherwise specified, comprising at least one unsaturation, i.e. at least one double bond. An alkenyl group covered by the scope of the present invention is for example a group chosen from ethylene, propyl-1-ene, propyl-2-ene, butyl-1-ene, butyl-2-ene, etc.

The expression "$C_2$-$C_{10}$ alkenylthio" in the present invention represents a "$(C_2$-$C_{10}$ alkenyl)-S—", i.e. an alkenyl moiety of 2 to 10 carbon atoms, if not otherwise specified, as defined above linked to the rest of the molecule by a sulfur atom.

The expression "$C_2$-$C_{10}$ alkenyloxy", in the present invention represents a "$(C_1$-$C_6$ alkenyl)-O—" group, i.e. an alkenyl moiety with 2 to 10 carbon atoms, if not otherwise specified, as defined above, linked to the rest of the molecule by an oxygen atom. Examples of alkenyloxy groups covered by the scope of the present invention are ethylenoxy, propyl-1-enoxy groups etc.

The expressions "$C_2$-$C_{10}$ alkynyl"/"alkynyl" (i.e. the number of carbons in "alkynyl" are not explicitly given) in the present invention mean a cyclic, linear or branched aliphatic group with 2 to 10 carbon atoms, if not otherwise specified, comprising at least one double insaturation, i.e. at least one triple bond. Examples of alkenyl groups covered by the scope of the present invention are acetylene, propyl-1-yne, propyl-2-yne, butyl-1-yne, butyl-2-yne, etc.

The expression "$C_2$-$C_{10}$ alkynyloxy", in the present invention means an alkynyl group defined above bound to an oxygen atom. Examples of alkynyloxy groups covered by the scope of the present invention are acetylenoxy, propyn-1-yloxy groups etc.

The expression "$C_2$-$C_{10}$ alkynylthio" in the present invention represents a "$(C_2$-$C_{10}$ alkynyl)-S—", i.e. an alkynyl moiety of 2 to 10 carbon atoms, if not otherwise specified, as defined above linked to the rest of the molecule by a sulfur atom.

As used herein, a "phenoxy group" refers to a group of formula $C_6H_5O$—, and a "thiophenoxy group" refers to a group of formula $C_6H_5S$—. Also, as used herein, "phenol" refers to $C_6H_5OH$, and "thiophenol" refers to $C_6H_5SH$.

The expression "halogen atom" (equivalent to "halo" when used) in the present invention means at least one atom of fluorine, chlorine, bromine or iodine.

As used herein, a "$C_1$-$C_{10}$ haloalkyl" is understood as a $C_1$-$C_{10}$ alkyl group as presently defined, of the same number of carbon atom, wherein at least one hydrogen atom is substituted with a halogen atom. Examples of $C_1$-$C_{10}$ haloalkyl are $CH_2F_1$, —$CHF_2$—, —$CF_3$, $CH_2Cl_1$, —$CHCl_2$—, —$CCl_3$, $CH_2Br_1$, —$CHBr_2$—, —$CBr_3$, $CH_2I_1$, —$CHI_2$—, —$Cl_3$, —$CH_2$—$CH_2F_1$, —$CH_2$—$CHF_2$—, —$CH_2$—$CF_3$, —$CFH$—$CH_3$, —$CF_2$—$CH_3$, etc.

In all $C_1$-$C_{10}$ alkyl, and derivatives thereof as defined above comprising an alkyl, if not otherwise specified, a preferred embodiment, is a $C_1$-$C_6$ alkyl group, and a more preferred embodiment is as defined above $C_1$-$C_4$ alkyl.

In all $C_1$-$C_{10}$ alkenyl, and derivatives thereof as defined above comprising an alkenyl, if not otherwise specified, a preferred embodiment, is a $C_1$-$C_6$ alkenyl group, and a more preferred embodiment is as defined above $C_1$-$C_4$ alkenyl.

In all $C_1$-$C_{10}$ alkynyl, and derivatives thereof as defined above comprising an alkynyl, if not otherwise specified, a preferred embodiment, is a $C_1$-$C_6$ alkynyl group, and a more preferred embodiment is as defined above $C_1$-$C_4$ alkynyl.

The expression "nitro" in the present invention means a $NO_2$ group.

As used herein, a $C_1$-$C_{10}$ alkylene group is a bivalent linear or branched saturated aliphatic group with 1 to 10 carbon atoms. An alkylene group covered by the scope of the present invention is for example a group chosen from methylene (—$CH_2$—), ethylene (—$CH_2$—$CH_2$—), propylene (—$CH_2$—$CH_2$—$CH_2$—), isopropylene (—$CH_2$—$CH$($CH_3$)—), etc.

The expression "leaving group" (or "LG") in the context of the present invention represents a molecular fragment or an atom departing from the molecule it initially belonged to, with typically a pair of electrons being torn off said molecule. Such "leaving groups" according to the present invention, can be chosen in the group consisting of amides (e.g. acetamide), sulfonyles (e.g. tosylate, mesylates), oxy-carbonyls (i.e. carboxylates), carbamates (e.g. Boc), dinitrogen ($N_2^+$), perfluoroalkylsulfonates (triflate), halogens (i.e. F, Cl, Br, I), amines, thiolates, phosphates, phenoxides. Preferably the "leaving groups" of the present invention are chosen in the group consisting of amides (e.g. acetamide), sulfonyles (e.g. tosylate, mesylates), oxy-carbonyls (i.e. carboxylates), carbamates (e.g. Boc).

An "electron-withdrawing group" ("EWG") means in the context of the present invention that the fragments is an electron attracting fragment, such as para-halogenophenyl, a $CF_3$, a phenyl, a fragment comprising a carbonyl, a cyano, a 3-pyridyl, a 4-methoxy phenyl, an amide, a sulphonamide, a carbamate, a 3,4,5-trimethoxyphenyl, a 4-methylthio-phenyl, a 4-ethoxy-phenyl, a 4-iodo-phenyl, a 4-nitro phenyl or a 4-[(2,3 diol)-propoxy]-phenyl fragment, preferably an inductive attracting fragment such as a para-halogenophenyl, a $CF_3$, a phenyl, a 3-pyridyl, a 4-methoxy phenyl, a 3,4,5-trimethoxyphenyl, a 4-methylthio-phenyl, a 4-ethoxy-phenyl, a 4-iodo-phenyl, a 4-nitro phenyl or a 4-[(2,3 diol)-propoxy]-phenyl fragment.

The term "microwaves" ("MW") according to the present invention comprises any electromagnetic radiation with wavelengths ranging from as long as a meter to as short to a millimetre, with frequencies between 300 MHz and 300 GHz. On a practical point of view, the frequency and other characteristics of the microwaves are adapted to the solvent used. For example, in the case of polar solvents like water, a frequency of 2.46 GHz will be used. Thus in the context of the present invention, the frequency of the MW used is preferably comprised between 1 and 10 GHz, more specifically from 2 to 3 GHz, such as 2.46 Ghz.

The expression "ambient temperature" ("AT") in the context of the present invention means a temperature comprised between 20 and 25° C.

An "antibiotic activity" according to the present invention is the generic definition as understood by the skilled person, that is to say an effect of an "antibiotic agent". Such an "antibiotic agent" is a substance that kills, blocks or slows the growth of one or more bacteria. By "growth" is included in the scope of the present invention any cell operation leading to a volumetric increase of the cell (i.e. of the bacterium), a cell division (of the bacteria) or a cell reproduction (of the bacteria).

The expression "pharmaceutical composition" in the present invention means any composition comprising a therapeutically effective dose of a compound of the invention and at least one pharmaceutically acceptable excipient. Said excipients are selected, depending on the pharmaceutical form and the desired method of administration, from the usual excipients known by a person skilled in the art.

The term «pharmaceutically acceptable salt» is intended to mean, in the framework of the present invention, a salt of a compound which is pharmaceutically acceptable (i.e. which is useful to the preparation of a pharmaceutical composition, and what is generally safe and non-toxic, for a pharmaceutical use), and which possesses the pharmacological activity of the corresponding compound. Such salts comprise:

(1) hydrates and solvates,
(2) acid addition salts formed with inorganic acids such as hydrochloric, hydrobromic, sulfuric, nitric and phosphoric acid and the like; or formed with organic acids such as acetic, benzenesulfonic, fumaric, glucoheptonic, gluconic, glutamic, glycolic, hydroxynaphtoic, 2-hydroxyethanesulfonic, lactic, maleic, malic, mandelic, methanesulfonic, muconic, 2-naphthalenesulfonic, propionic, succinic, dibenzoyl-L-tartaric, tartaric, p-toluenesulfonic, trimethylacetic, and trifluoroacetic acid and the like, and
(3) salts formed when an acid proton present in the compound is either replaced by a metal ion, such as an alkali metal ion, an alkaline-earth metal ion, or an aluminium ion; or coordinated with an organic or inorganic base. Acceptable organic bases comprise diethanolamine, ethanolamine, N-methylglucamine, triethanolamine, tromethamine and the like. Acceptable inorganic bases comprise aluminium hydroxide, calcium hydroxide, potassium hydroxide, sodium carbonate and sodium hydroxide.

The terms "drug" or "medicament" are equivalent in the context of the present invention.

The expression "treatment" is intended to be directed towards all types of animals, preferably mammals, more preferably humans. In the case of a treatment of an animal which is not human kind, it will be referred to a veterinary treatment.

DETAILED DESCRIPTION

1. Compounds of Formula (I)

The compound(s) of the present invention contain two stereogenic centres. They may thus be in the form of mixtures of enantiomers and/or diastereomers. The compounds of formula (I) may be as the cis- or trans-diastereomer. Typically, the compounds of formula (I) are cis-diastereomers.

$Ar_1$ and $Ar_2$

In a particular embodiment, $Ar_1$ and $Ar_2$ are identical. In another particular embodiment, $Ar_1$ and $Ar_2$ are different.

In a particular embodiment, $Ar_1$ and $Ar_2$ are independently a mono or polycyclic $C_5$-$C_{12}$ aryl or mono or polycyclic $C_3$-$C_{12}$ heteroaryl group wherein the aryl or heteroaryl group is optionally substituted with:
  one to three, preferably 1 or 2 substituents independently selected from the group consisting of: a halogen atom, OH, $C_1$-$C_6$ alkyl, $C_3$-$C_7$ cycloalkyl, $C_1$-$C_6$ alkoxy, $C_3$-$C_7$ cycloalkoxy, nitro, cyano, formyl, amino-$C_1$-$C_{10}$ alkoxy, (carboxylic acid)-$C_1$-$C_{10}$ alkoxy, (carboxylic ($C_1$-$C_6$)alkyl ester)-$C_1$-$C_{10}$ alkoxy, (1,2 diol)-$C_2$-$C_{10}$ alkoxy, —O—($C_1$-$C_6$)alkyl-O—($C_1$-$C_6$)alkyl-OH, ($C_1$-$C_6$)-alkoxy-($C_1$-$C_6$)-alkyl, $C_2$-$C_6$ alkylcarbonyl, $C_1$-$C_6$ alkylthio, $C_1$—$O_6$ thioalkyl, ($C_1$-$C_6$)-alkylthio-($C_1$-$C_6$)-alkyl, $C_1$-$C_6$ alkylsulfinyl, $C_1$-$C_6$ alkylsulfonyl, $C_1$-$C_6$ haloalkyl, $C_1$-$C_6$ haloalkoxy, $C_1$-$C_6$ haloalkoxy alkyl, $C_2$-$C_6$ haloalkylcarbonyl, $C_1$-$C_6$ haloalkylthio, $C_1$-$C_6$ haloalkylsulfinyl, $C_1$-$C_6$ haloalkylsulfonyl, $C_2$-$C_6$ alkenyl, $C_2$-$C_6$ alkynyl, $C_2$-$C_6$ haloalkynyl, $C_2$-$C_6$ haloalkenyl, $C_2$-$C_6$ haloalkenyloxy, $C_2$-$C_6$ haloalkynyloxy, $C_2$-$C_6$ alkenyloxy, $C_2$-$C_6$ alkynyloxy, $C_2$-$C_6$ alkenylthio, $C_2$-$C_6$ alkynylthio, $C_2$-$C_6$ haloalkenylthio, $C_2$-$C_6$ haloalkynylthio and/or a $C_1$-$C_6$ alkoxy optionally substituted by a mono or polycyclic $C_5$-$C_{12}$ aryl group,
  a mono $C_5$-$C_6$ aryl group optionally substituted with a $C_1$-$C_6$ alkoxy; and/or
  a bridging group of formula O—$CH_2$—O— or O—$CH_2CH_2$—O—.

In a particular embodiment, $Ar_1$ and $Ar_2$ are independently a mono or polycyclic $C_5$-$C_{12}$ aryl or mono or polycyclic $C_3$-$C_{12}$ heteroaryl group wherein the aryl or heteroaryl group is optionally substituted with:
  one to three, preferably 1 or 2 substituents independently selected from the group consisting of: a halogen atom, OH, $C_1$-$C_6$ alkyl, $C_3$-$C_7$ cycloalkyl, $C_1$-$C_6$ alkoxy, $C_3$-$C_7$ cycloalkoxy, nitro, cyano, formyl, amino-$C_1$-$C_{10}$ alkoxy, (carboxylic acid)-$C_1$-$C_{10}$ alkoxy, (carboxylic ($C_1$-$C_6$)alkyl ester)-$C_1$-$C_{10}$ alkoxy, (1,2 diol)-$C_2$-$C_{10}$ alkoxy, —O—($C_1$-$C_6$)alkyl-O—($C_1$-$C_6$)alkyl-OH, ($C_1$-$C_6$)-alkoxy-($C_1$-$C_6$)-alkyl, $C_2$-$C_6$ alkylcarbonyl, $C_1$-$C_6$ alkylthio, $C_1$-$C_6$ thioalkyl, ($C_1$-$C_6$)-alkylthio-($C_1$-$C_6$)-alkyl, $C_1$-$C_6$ alkylsulfinyl, $C_1$-$C_6$ alkylsulfonyl, $C_1$-$C_6$ haloalkyl, $C_1$-$C_6$ haloalkoxy, $C_1$-$C_6$ haloalkoxy alkyl, $C_2$-$C_6$ haloalkylcarbonyl, $C_1$-$C_6$ haloalkylthio, $C_1$-$C_6$ haloalkylsulfinyl, $C_1$-$C_6$ haloalkylsulfonyl, $C_2$-$C_6$ alkenyl, $C_2$-$C_6$ alkynyl, $C_2$-$C_6$ haloalkynyl, $C_2$-$C_6$ haloalkenyl, $C_2$-$C_6$ haloalkenyloxy, $C_2$-$C_6$ haloalkynyloxy, $C_2$-$C_6$ alkenyloxy, $C_2$-$C_6$ alkynyloxy, $C_2$-$C_6$ alkenylthio, $C_2$-$C_6$ alkynylthio, $C_2$-$C_6$ haloalkenylthio, $C_2$-$C_6$ haloalkynylthio and/or a $C_1$-$C_6$ alkoxy optionally substituted by a mono or polycyclic $C_5$-$C_{12}$ aryl group, and/or a bridging group of formula O—$CH_2$—O— or O—$CH_2CH_2$—O—.

In a particular embodiment, $Ar_1$ and $Ar_2$ are independently a mono or polycyclic $C_5$-$C_{12}$ aryl or mono or polycyclic $C_3$-$C_{12}$ heteroaryl group wherein the aryl or heteroaryl group is optionally substituted with one to three electron-donating groups (EDG), such as OH, $C_1$-$C_6$ alkyl, $C_3$-$C_7$ cycloalkyl, $C_1$-$C_6$ alkoxy, $C_3$-$C_7$ cycloalkoxy, (1,2 diol)-$C_2$-$C_{10}$ alkoxy, —O—($C_1$-$C_6$)alkyl-O—($C_1$-$C_6$)alkyl-OH, ($C_1$-$C_6$)-alkoxy-($C_1$-$C_6$)-alkyl, $C_1$-$C_6$ alkylthio, $C_1$-$C_6$ thioalkyl, ($C_1$-$C_6$)-alkylthio-($C_1$-$C_6$)-alkyl, $C_1$-$C_6$ haloalkoxy, $C_1$-$C_6$ haloalkoxy alkyl, a $C_1$-$C_6$ alkoxy optionally substituted by a mono or polycyclic $C_5$-$C_{12}$ aryl group, or a bridging group of formula O—$CH_2$—O— or O—$CH_2CH_2$—O—.

Preferably, the electron-donating groups (EDG) is OH, $C_1$-$C_6$ alkyl, $C_3$-$C_7$ cycloalkyl, $C_1$-$C_6$ alkoxy, $C_3$-$C_7$ cycloalkoxy, (1,2 diol)-$C_2$-$C_{10}$ alkoxy, —O—($C_1$-$C_6$)alkyl-O—($C_1$-$C_6$)alkyl-OH, ($C_1$-$C_6$)-alkoxy-($C_1$-$C_6$)-alkyl, $C_1$-$C_6$ haloalkoxy, $C_1$-$C_6$ haloalkoxy alkyl, a $C_1$-$C_6$ alkoxy optionally substituted by a mono or polycyclic $C_5$-$C_{12}$ aryl group, or a bridging group of formula O—$CH_2$—O— or O—$CH_2CH_2$—O—. More preferably, it is OH, $C_1$-$C_6$ alkyl, $C_3$-$C_7$ cycloalkyl, $C_1$-$C_6$ alkoxy, $C_3$-$C_7$ cycloalkoxy. For instance, it is OH or a linear $C_1$-$C_6$ alkoxy, such as a methoxy group.

In a particular embodiment, $Ar_1$ and $Ar_2$ are independently a mono or polycyclic $C_5$-$C_{12}$ aryl, such as a phenyl group or a naphthyl group (preferably a phenyl group), optionally substituted with 1 to three substituents as listed above, particularly electron-donating groups, such as listed above. For example, $Ar_1$ and $Ar_2$ are independently a phenyl group, optionally substituted with 1 to 3 substituents selected from the group consisting of OH, $C_1$-$C_6$ alkyl, $C_3$-$C_7$ cycloalkyl, $C_1$-$C_6$ alkoxy, $C_3$-$C_7$ cycloalkoxy, (1,2 diol)-$C_2$-$C_{10}$ alkoxy, —O—($C_1$-$C_6$)alkyl-O—($C_1$-$C_6$)alkyl-OH, ($C_1$-$C_6$)-alkoxy-($C_1$-$C_6$)-alkyl, $C_1$-$C_6$ haloalkoxy, $C_1$-$C_6$ haloalkoxy alkyl, a $C_1$-$C_6$ alkoxy optionally substituted by a mono or polycyclic $C_5$-$C_{12}$ aryl group, or a bridging group of formula O—$CH_2$—O— or O—$CH_2CH_2$—O—. More preferably, it is OH, $C_1$-$C_6$ alkyl, $C_3$-$C_7$ cycloalkyl, $C_1$-$C_6$ alkoxy, $C_3$-$C_7$ cycloalkoxy. For instance, $Ar_1$ and $Ar_2$ are independently a phenyl group, optionally substituted with 1 to 3 OH or linear $C_1$-$C_6$ alkoxy, such as a methoxy group.

In a particular embodiment, $Ar_1$ and $Ar_2$ are independently a mono or polycyclic $C_5$-$C_{12}$ aryl, such as a phenyl group, optionally substituted with 1 to three substituents, notably with 1 substituent, selected from the group consisting of a halogen atom, OH, $C_1$-$C_6$ alkyl, $C_1$-$C_6$ alkoxy, $C_1$-$C_6$ haloalkyl, $C_1$-$C_6$ haloalkoxy, and a bridging group of formula O—$CH_2$—O— or O—$CH_2CH_2$—O—. Advantageously, the substituents are selected from the group consisting of a halogen atom, $C_1$-$C_6$ alkyl, $C_1$-$C_6$ alkoxy, $C_1$-$C_6$ haloalkyl and $C_1$-$C_6$ haloalkoxy. More preferably, the substituents are selected from the group consisting of a halogen atom and $C_1$-$C_6$ alkoxy. The halogen is a fluorine, a chlorine, a bromine or an iodine and more particularly a chlorine, a bromine or an iodine.

In a particular embodiment, $Ar_1$ is a phenyl, a bromophenyl, a chlorophenyl, a dichlorophenyl (in particular a 2,4-dichlorophenyl), a fluorophenyl, a (para-)methoxybiphenyl or a methoxyphenyl, such as a phenyl, a chlorophenyl, a fluorophenyl or a methoxyphenyl, and preferably it is a phenyl or a methoxyphenyl. In another particular embodiment, $Ar_2$ is a phenyl, a chlorophenyl, a fluorophenyl or a methoxyphenyl, and preferably it is a methoxyphenyl. Thus, $Ar_1$ and $Ar_2$ can be independently a phenyl, a chlorophenyl, a fluorophenyl or a methoxyphenyl. Typically, $Ar_1$ is a phenyl or a methoxyphenyl and $Ar_2$ is a methoxyphenyl.

$Ar_3$

Advantageously, $Ar_3$ is a mono or polycyclic $C_5$-$C_{12}$ aryl or mono or polycyclic $C_3$-$C_{12}$ heteroaryl group, preferably a mono or polycyclic $C_5$-$C_{12}$ aryl such as a phenyl group, wherein the aryl or heteroaryl group is optionally substituted with:

halogen atoms, OH, $C_1$-$C_6$ alkyl, $C_3$-$C_7$ cycloalkyl, $C_1$-$C_6$ alkoxy, $C_3$-$C_7$ cycloalkoxy, cyano, formyl, nitro, $C_1$-$C_6$ alkyl, $C_3$-$C_7$ cycloalkyl, $C_1$-$C_6$ alkoxy, ($C_1$-$C_6$)-alkoxy-($C_1$-$C_6$)-alkyl, $C_2$-$C_6$ alkylcarbonyl, $C_1$-$C_6$ alkylthio, $C_1$-$C_6$ thioalkyl, ($C_1$-$C_6$)-alkylthio-($C_1$-$C_6$)-alkyl, $C_1$-$C_6$ alkylsulfinyl, $C_1$-$C_6$ alkylsulfonyl, $C_1$-$C_6$ haloalkyl, $C_1$-$C_6$ haloalkoxy, $C_1$-$C_6$ haloalkoxy alkyl, $C_2$-$C_6$ haloalkylcarbonyl, $C_1$-$C_6$ haloalkylthio, $C_1$-$C_6$ haloalkylsulfinyl, $C_1$-$C_6$ haloalkylsulfonyl, $C_2$-$C_6$ alkenyl, $C_2$-$C_6$ alkynyl, $C_2$-$C_6$ haloalkynyl, $C_2$-$C_6$ haloalkenyl, $C_2$-$C_6$ haloalkenyloxy, $C_2$-$C_6$ haloalkynyloxy, $C_2$-$C_6$ alkenyloxy, $C_2$-$C_6$ alkynyloxy, $C_2$-$C_6$ alkenylthio, $C_2$-$C_6$ alkynylthio, $C_2$-$C_6$ haloalkenylthio, $C_2$-$C_6$ haloalkynylthio group, and/or a monocyclic $C_5$-$C_6$ aryl group optionally substituted by a $C_1$-$C_6$ alkyloxy group, a mono $C_5$-$C_6$ aryl group optionally substituted with a $C_1$-$C_6$ alkoxy; and/or a bridging group of formula O—$CH_2$—O— or O—$CH_2CH_2$—O—.

Further advantageously, $Ar_3$ is a mono or polycyclic $C_5$-$C_{12}$ aryl or mono or polycyclic $C_3$-$C_{12}$ heteroaryl group, preferably a mono or polycyclic $C_5$-$C_{12}$ aryl such as a phenyl group, wherein the aryl or heteroaryl group is optionally substituted with:

halogen atoms, OH, $C_1$-$C_6$ alkyl, $C_3$-$C_7$ cycloalkyl, $C_1$-$C_6$ alkoxy, $C_3$-$C_7$ cycloalkoxy, cyano, formyl, nitro, $C_1$-$C_6$ alkyl, $C_3$-$C_7$ cycloalkyl, $C_1$-$C_6$ alkoxy, ($C_1$-$C_6$)-alkoxy-($C_1$-$C_6$)-alkyl, $C_2$-$C_6$ alkylcarbonyl, $C_1$-$C_6$ alkylthio, $C_1$-$C_6$ thioalkyl, ($C_1$-$C_6$)-alkylthio-($C_1$-$C_6$)-alkyl, $C_1$-$C_6$ alkylsulfinyl, $C_1$-$C_6$ alkylsulfonyl, $C_1$-$C_6$ haloalkyl, $C_1$-$C_6$ haloalkoxy, $C_1$-$C_6$ haloalkoxy alkyl, $C_2$-$C_6$ haloalkylcarbonyl, $C_1$-$C_6$ haloalkylthio, $C_1$-$C_6$ haloalkylsulfinyl, $C_1$-$C_6$ haloalkylsulfonyl, $C_2$-$C_6$ alkenyl, $C_2$-$C_6$ alkynyl, $C_2$-$C_6$ haloalkynyl, $C_2$-$C_6$ haloalkenyl, $C_2$-$C_6$ haloalkenyloxy, $C_2$-$C_6$ haloalkynyloxy, $C_2$-$C_6$ alkenyloxy, $C_2$-$C_6$ alkynyloxy, $C_2$-$C_6$ alkenylthio, $C_2$-$C_6$ alkynylthio, $C_2$-$C_6$ haloalkenylthio, $C_2$-$C_6$ haloalkynylthio group, and/or a monocyclic $C_5$-$C_6$ aryl group optionally substituted by a $C_1$-$C_6$ alkyloxy group, and/or a bridging group of formula O—$CH_2$—O— or O—$CH_2CH_2$—O—.

Preferably, $Ar_3$ is substituted with 1 to 3 substituents selected from the group consisting of halogen atoms, OH, $C_1$-$C_6$ alkyl, $C_3$-$C_7$ cycloalkyl, $C_1$-$C_6$ alkoxy, $C_3$-$C_7$ cycloalkoxy, ($C_1$-$C_6$)-alkoxy-($C_1$-$C_6$)-alkyl, $C_2$-$C_6$ alkylcarbonyl, $C_1$-$C_6$ alkylthio, $C_1$-$C_6$ thioalkyl, ($C_1$-$C_6$)-alkylthio-($C_1$-$C_6$)-alkyl, $C_1$-$C_6$ alkylsulfinyl, $C_1$-$C_6$ alkylsulfonyl, $C_1$-$C_6$ haloalkyl, $C_1$-$C_6$ haloalkoxy, $C_1$-$C_6$ haloalkoxyalkyl, $C_2$-$C_6$ haloalkylcarbonyl, $C_1$-$C_6$ haloalkylthio, $C_1$-$C_6$ haloalkylsulfinyl, $C_1$-$C_6$ haloalkylsulfonyl, $C_2$-$C_6$ alkenyl, $C_2$-$C_6$ alkynyl, $C_2$-$C_6$ haloalkynyl, $C_2$-$C_6$ haloalkenyl, $C_2$-$C_6$ haloalkenyloxy, $C_2$-$C_6$ haloalkynyloxy, $C_2$-$C_6$ alkenyloxy, $C_2$-$C_6$ alkynyloxy, $C_2$-$C_6$ alkenylthio, $C_2$-$C_6$ alkynylthio, $C_2$-$C_6$ haloalkenylthio, $C_2$-$C_6$ haloalkynylthio group, and/or a monocyclic $C_5$-$C_6$ aryl group optionally substituted by a $C_1$-$C_6$ alkyloxy group; a mono $C_5$-$C_6$ aryl group optionally substituted with a $C_1$-$C_6$ alkoxy; and/or $Ar_3$ is substituted with a bridging group of formula O—$CH_2$—O— or O—$CH_2CH_2$—O—.

Advantageously, $Ar_3$ is optionally substituted with 1, 2 or 3, preferably 1 or 2, substituents selected from the group consisting of a halogen atom (such as a iodine, a bromine or a chlorine atom), $C_1$-$C_6$ alkyl, $C_3$-$C_7$ cycloalkyl, $C_1$-$C_6$ alkoxy, $C_3$-$C_7$ cycloalkoxy, a $C_1$-$C_6$ haloalkyl, a $C_1$-$C_6$ alkoxy, OH, and a phenyl group optionally substituted with a $C_1$-$C_6$ alkoxy such as a methoxy or an ethoxy group. More preferably, $Ar_3$ is optionally substituted with 1, 2 or 3, preferably 1 or 2, substituents selected from the group consisting of a halogen atom (such as a iodine, a bromine or a chlorine atom), $C_1$-$C_6$ alkyl, $C_3$-$C_7$ cycloalkyl, $C_1$-$C_6$ alkoxy, $C_3$-$C_7$ cycloalkoxy, a $C_1$-$C_6$ haloalkyl, a $C_1$-$C_6$ alkoxy and OH. Even more preferably, $Ar_3$ is optionally substituted with 1, 2 or 3 (preferably 1 or 2) substituents selected from the group consisting of a halogen atom (such as iodine, bromine or chlorine), a $C_1$-$C_6$ haloalkyl, a $C_1$-$C_6$ alkoxy and OH. Most preferably, $Ar_3$ is optionally substituted with 1 or 2 (preferably 1) substituents selected from the group consisting of iodine, bromine, chlorine, $CF_3$, $OCH_3$ and OH.

In a particular embodiment, $Ar_3$ is a mono or polycyclic $C_5$-$C_{12}$ aryl group, preferably a phenyl or naphthyl group, optionally substituted with 1 to 3 substituents independently selected from the group defined above.

In a particular embodiment, $Ar_3$ is a mono or polycyclic $C_5$-$C_{12}$ aryl group, preferably phenyl or naphthyl group, optionally substituted with 1 or 2, substituents selected from the group consisting of a halogen atom, $C_1$-$C_6$ alkyl, $C_3$-$C_7$ cycloalkyl, $C_1$-$C_6$ alkoxy, $C_3$-$C_7$ cycloalkoxy, $C_1$-$C_6$ haloalkyl, $C_1$-$C_6$ alkoxy and OH, preferably a halogen atom (such as iodine, bromine or chlorine), $C_1$-$C_6$ haloalkyl, $C_1$-$C_6$ alkoxy and OH. More preferably, $Ar_3$ is optionally substituted with 1 or 2 (preferably 1) substituents selected from the group consisting of iodine, bromine, chlorine, $CF_3$, $OCH_3$, $OCH_2CH_3$ and OH. For instance, $Ar_3$ is a phenyl group optionally substituted with 1 substituent selected from the group consisting of iodine, bromine, chlorine, $CF_3$, $OCH_3$ (and OH).

In a particular embodiment, $Ar_3$ is a mono or polycyclic $C_5$-$C_{12}$ aryl group, preferably a phenyl group, optionally substituted with 1, 2 or 3, preferably 1, substituents selected from the group consisting of a halogen atom, OH, $C_1$-$C_6$ alkyl, $C_1$-$C_6$ alkoxy, $C_1$-$C_6$ haloalkyl, $C_1$-$C_6$ haloalkoxy and a bridging group of formula O—$CH_2$—O— or O—$CH_2CH_2$—O—. Advantageously, the substituents are selected from the group consisting of a halogen atom, $C_1$-$C_6$ alkyl, $C_1$-$C_6$ alkoxy, $C_1$-$C_6$ haloalkyl and $C_1$-$C_6$ haloalkoxy. More preferably, the substituents are selected from the group consisting of a halogen atom, $C_1$-$C_6$ haloalkyl and $C_1$-$C_6$ alkoxy. The halogen is a fluorine, a chlorine, a bromine or an iodine and more particularly a chlorine, a bromine or an iodine.

In a particular embodiment, $Ar_3$ is a phenyl, a bromophenyl, a chlorophenyl, a fluorophenyl, an iodophenyl, a methoxyphenyl or a trifluoromethyl-phenyl.

$R_4$

In a particular embodiment, $R_4$ is a hydrogen atom or a linear $C_1$-$C_6$ alkyl group optionally substituted with 1 to 3 substituents independently selected from the group consisting of: halogen atoms, hydroxyl (OH), $C_1$-$C_6$-alkoxy, amino, $C_1$-$C_6$-alkylamino, di($C_1$-$C_6$)alkylamino, COOH, COO—($C_1$-$C_6$)alkyl, $CONH_2$, CONH($C_1$-$C_6$)alkyl, $C_1$-$C_6$ thioalkyl, SH, S(O)($C_1$-$C_6$)alkyl, S($O_2$)($C_1$-$C_6$)alkyl, and a mono $C_5$-$C_6$ aryl group.

In a particular embodiment, $R_4$ is a hydrogen atom or a linear $C_1$-$C_4$ alkyl group optionally substituted with 1 to 3 substituents independently selected from the group consisting of: halogen atoms, hydroxyl (OH), linear $C_1$-$C_6$-alkoxy, amino, linear $C_1$-$C_6$-alkylamino, di(linear $C_1$-$C_6$)alkylamino, linear $C_1$-$C_6$ thioalkyl, SH, linear S(O)($C_1$-$C_6$)alkyl, linear S($O_2$)($C_1$-$C_6$)alkyl.

In a preferred embodiment, $R_4$ is a methyl group or H. Most preferably, $R_4$ is H.

$R_{4a}$

In a particular embodiment, $R_{4a}$ is a hydrogen atom or a linear $C_1$-$C_6$ alkyl group optionally substituted with 1 to 3 substituents independently selected from the group consisting of: halogen atoms, hydroxyl (OH), oxo (=O), $C_1$-$C_6$-alkoxy, amino, arylimido optionally substituted, $C_1$-$C_6$-alkylamino, di($C_1$-$C_6$)alkylamino, COOH, COO—($C_1$-$C_6$) alkyl, $CONH_2$, CONH($C_1$-$C_6$)alkyl, $C_1$—$O_6$ thioalkyl, SH, S(O)($C_1$-$C_6$)alkyl, S($O_2$)($C_1$-$C_6$)alkyl, and a mono $C_5$-$C_6$ aryl group. Advantageously, the arylimido, preferably a phenylimido, is optionally substituted with 1 to 3, preferably 1, substituents selected from the group consisting of a halogen atom, $C_1$-$C_6$ alkyl, $C_1$-$C_6$ alkoxy, $C_1$-$C_6$ haloalkyl and $C_1$-$C_6$ haloalkoxy.

In a particular embodiment, $R_{4a}$ is a hydrogen atom or a linear $C_1$-$C_4$ alkyl group optionally substituted with 1 to 3 substituents independently selected from the group consisting of:

halogen atoms, hydroxyl (OH), oxo (=O), linear $C_1$-$C_6$-alkoxy, amino, arylimido optionally substituted, linear $C_1$-$C_6$-alkylamino, di(linear $C_1$-$C_6$)alkylamino, linear $C_1$-$C_6$ thioalkyl, SH, linear S(O)($C_1$-$C_6$)alkyl, linear S($O_2$)($C_1$-$C_6$) alkyl. Advantageously, the arylimido, preferably a phenylimido, is optionally substituted with 1 to 3, preferably 1, substituents selected from the group consisting of a halogen atom, $C_1$-$C_6$ alkyl, $C_1$-$C_6$ alkoxy, $C_1$-$C_6$ haloalkyl and $C_1$-$C_6$ haloalkoxy.

In a particular embodiment, $R_{4a}$ is a hydrogen atom or a linear $C_1$-$C_4$ alkyl group optionally substituted with 1 to 3 substituents independently selected from the group consisting of: oxo (=O) and arylimido optionally substituted. Advantageously, the arylimido, preferably a phenylimido, is optionally substituted with 1 to 3, preferably 1, substituents selected from the group consisting of a halogen atom, $C_1$-$C_6$ alkyl, $C_1$-$C_6$ alkoxy, $C_1$-$C_6$ haloalkyl and $C_1$-$C_6$ haloalkoxy.

In a particular embodiment, $R_{4a}$ is a group of formula —C(=X)$R_7$ with X representing O or N—$R_8$, preferably N$R_8$, $R_7$ representing a $C_1$-$C_6$ alkyl such as a methyl, and $R_8$ representing an aryl, such as a phenyl, optionally substituted with 1 to 3, preferably 1, substituents selected from the group consisting of a halogen atom, $C_1$-$C_6$ alkyl, $C_1$-$C_6$ alkoxy, $C_1$-$C_6$ haloalkyl and $C_1$-$C_6$ haloalkoxy, preferably selected from halogen atoms such as chlorine or bromine.

In a preferred embodiment, $R_{4a}$ is a group of formula —C(=X)Me with X representing O or N—$R_8$, preferably N$R_8$, and $R_8$ representing a phenyl optionally substituted with 1 to 3, preferably 1, substituents selected from the group consisting of a halogen atom, $C_1$-$C_6$ alkyl, $C_1$-$C_6$ alkoxy, $C_1$-$C_6$ haloalkyl and $C_1$-$C_6$ haloalkoxy, preferably selected from halogen atoms such as chlorine or bromine.

$R_6$

In $R_6$, each $C_1$-$C_{10}$ alkyl, $C_3$-$C_{10}$ cycloalkyl, $C_1$-$C_{10}$ alkoxy, $C_1$-$C_{10}$ haloalkoxy, ($C_1$-$C_6$)-alkoxy-($C_1$-$C_6$)-alkyl, ($C_1$-$C_6$)-haloalkoxy-($C_1$-$C_6$)-alkyl, $C_1$-$C_{10}$ thioalkyl, ($C_1$-$C_6$)-alkylthio-($C_1$-$C_6$)-alkyl, $C_1$-$C_{10}$ alkylsulfinyl, $C_1$-$C_{10}$ haloalkylsulfinyl, $C_1$-$C_{10}$ haloalkylsulfonyl, $C_1$-$C_{10}$ alkylsulfonyl, $C_5$-$C_{12}$ arylsulfonyl, $C_2$-$C_{10}$ alkylcarbonyl, $C_2$-$C_{10}$ alkenyl, $C_2$-$C_{10}$ alkynyl, $C_2$-$C_{10}$ alkenyloxy, $C_2$-$C_{10}$ alkynyloxy, $C_2$-$C_{10}$ alkenylthio, $C_2$-$C_{10}$ alkynylthio, $C_1$-$C_{10}$ haloalkyl, $C_2$-$C_{10}$ haloalkenyl, $C_2$-$C_{10}$ haloalkynyl, $C_2$-$C_{10}$ haloalkylcarbonyl, $C_1$-$C_{10}$ haloalkylthio, $C_2$-$C_{10}$ haloalkenyloxy, $C_2$-$C_{10}$ haloalkynyloxy, $C_2$-$C_{10}$ haloalkenylthio, $C_2$-$C_{10}$ haloalkynylthio, $(C_5$-$C_{12})$-aryl-$(C_1$-$C_6)$-alkyl, $(C_5$-$C_{12})$-aryl-$(C_1$-$C_6)$-alkyl ester, mono or polycyclic $C_5$-$C_{12}$ aryl and mono or polycyclic $C_3$-$C_{12}$ heteroaryl group is optionally substituted with 1 to 3 substituents independently selected from the group consisting of: halogen atoms, hydroxyl (OH), nitro, cyano, formyl, $C_3$-$C_7$ cycloalkyl, $C_1$-$C_6$-alkoxy, amino, $C_1$-$C_6$ alkylamino, di($C_1$-$C_5$)alkylamino, COOH, COO—($C_1$-$C_6$)alkyl, $CONH_2$, CONH($C_1$-$C_5$)alkyl, $C_1$-$C_6$ thioalkyl, SH, S($C_1$-$C_6$)alkyl, S(O)($C_1$-$C_5$)alkyl, S($O_2$)($C_1$-$C_6$)alkyl, and a mono or polycyclic $C_5$-$C_{12}$ aryl group.

In a particular embodiment, $R_6$ is a hydrogen atom, a halogen atom, $C_1$-$C_{10}$ alkyl, $C_3$-$C_{10}$ cycloalkyl, $C_1$-$C_{10}$ alkoxy, $C_1$-$C_{10}$ haloalkoxy, $(C_1$—$O_6)$-alkoxy-$(C_1$—$O_6)$-alkyl, $(C_1$-$C_6)$-haloalkoxy-$(C_1$-$C_6$-alkyl, $C_1$-$C_{10}$ thioalkyl, $(C_1$-$C_6)$-alkylthio-$(C_1$-$C_6)$-alkyl, $C_1$-$C_{10}$ alkylsulfinyl, $C_1$-$C_{10}$ haloalkylsulfinyl, $C_1$-$C_{10}$ haloalkylsulfonyl, $C_1$-$C_{10}$ alkylsulfonyl, $C_5$-$C_{12}$ arylsulfonyl, formyl, $C_2$-$C_{10}$ alkenyl, $C_2$-$C_{10}$ alkenyloxy, $C_2$-$C_{10}$ alkenylthio, $C_1$-$C_{10}$ haloalkyl, $C_2$-$C_{10}$ haloalkenyl, $C_1$-$C_{10}$ haloalkylthio, $C_2$-$C_{10}$ haloalkenyloxy, $C_2$-$C_{10}$ haloalkenylthio, $(C_5$-$C_{12})$-aryl-$(C_1$-$C_6)$-alkyl, $(C_5$-$C_{12})$-aryl-$(C_1$-$C_6)$-alkyl ester, a mono or polycyclic $C_5$-$C_{12}$ aryl, or mono or polycyclic $C_3$-$C_{12}$ heteroaryl group, optionally substituted. Preferably, each $C_1$-$C_{10}$ alkyl, $C_3$-$C_{10}$ cycloalkyl, $C_1$-$C_{10}$ alkoxy, $C_1$-$C_{10}$ haloalkoxy, $(C_1$-$C_6)$-alkoxy-$(C_1$-$C_6)$-alkyl, $(C_1$—$O_6)$-haloalkoxy-$(C_1$-$C_6)$-alkyl, $C_1$-$C_{10}$ thioalkyl, $(C_1$-$C_6)$-alkylthio-$(C_1$-$C_6)$-alkyl, $C_1$-$C_{10}$ alkylsulfinyl, $C_1$-$C_{10}$ haloalkylsulfinyl, $C_1$-$C_{10}$ haloalkylsulfonyl, $C_1$-$C_{10}$ alkylsulfonyl, $C_5$-$C_{12}$ arylsulfonyl, formyl, $C_2$-$C_{10}$ alkenyl, $C_2$-$C_{10}$ alkenyloxy, $C_2$-$C_{10}$ alkenylthio, $C_1$-$C_{10}$ haloalkyl, $C_2$-$C_{10}$ haloalkenyl, $C_1$-$C_{10}$ haloalkylthio, $C_2$-$C_{10}$ haloalkenyloxy, $C_2$-$C_{10}$ haloalkenylthio, $(C_5$-$C_{12})$-aryl-$(C_1$-$C_6)$-alkyl, $(C_5$-$C_{12})$-aryl-$(C_1$-$C_6)$-alkyl ester, a mono or polycyclic $C_5$-$C_{12}$ aryl, or mono or polycyclic $C_3$-$C_{12}$ heteroaryl group is optionally substituted with 1 to 3 substituents independently selected from the group consisting of: halogen atoms, hydroxyl (OH), $C_1$-$C_6$-alkoxy, amino, $C_1$-$C_6$-alkylamino, di($C_1$-$C_6$)alkylamino, COOH, COO—($C_1$-$C_6$)alkyl, $CONH_2$, CONH($C_1$-$C_6$)alkyl, $C_1$-$C_6$ thioalkyl, SH, S(O)($C_1$-$C_6$)alkyl, S($O_2$)($C_1$-$C_6$)alkyl, and a mono $C_5$-$C_6$ aryl group.

In a particular embodiment, $R_6$ is a hydrogen atom or a linear $C_1$-$C_6$ alkyl group optionally substituted with 1 to 3 substituents independently selected from the group consisting of: halogen atoms, hydroxyl (OH), $C_1$-$C_6$-alkoxy, amino, $C_1$-$C_6$-alkylamino, di($C_1$-$C_6$)alkylamino, COOH, COO—($C_1$-$C_6$)alkyl, $CONH_2$, CONH($C_1$-$C_6$)alkyl, $C_1$-$C_6$ thioalkyl, SH, S(O)($C_1$-$C_6$)alkyl, S($O_2$)($C_1$-$C_6$)alkyl, and a mono $C_5$-$C_6$ aryl group.

In a particular embodiment, $R_6$ is a hydrogen atom or a linear $C_1$-$C_4$ alkyl group optionally substituted with 1 to 3 substituents independently selected from the group consisting of: halogen atoms, hydroxyl (OH), linear $C_1$-$C_6$-alkoxy, amino, linear $C_1$-$C_6$-alkylamino, di(linear $C_1$-$C_6$)alkylamino, linear $C_1$-$C_6$ thioalkyl, SH, linear S(O)($C_1$-$C_6$)alkyl, linear S($O_2$)($C_1$-$C_6$)alkyl.

In a preferred embodiment, $R_6$ is a methyl group or H. Most preferably, $R_6$ is H.

Combinations

Any combinations of particular and/or preferred embodiments of $Ar_1$, $Ar_2$, $Ar_3$, $R_4$, $R_{4a}$ and $R_6$ are encompassed by the present invention.

In a first particular embodiment, the compound of formula (I) is a compound of formula (Ia) and at least one of $R_4$ and $R_6$ is H. For instance, $R_4$ is H, or $R_6$ is H or both $R_4$ and $R_6$ are H. In this particular embodiment, $Ar_1$, $Ar_2$, $Ar_3$, are as defined above, and are advantageously independently a mono or polycyclic $C_5$-$C_{12}$ aryl group, preferably phenyl or naphthyl group, more preferably a phenyl, optionally substituted with 1, 2 or 3 (preferably 1) substituents as listed above for in connection with $Ar_1$, $Ar_2$, $Ar_3$, respectively. Preferably, $Ar_1$, $Ar_2$ and $Ar_3$ are independently a mono or polycyclic $C_5$-$C_{12}$ aryl group, preferably a phenyl group, optionally substituted with 1, 2 or 3 (preferably 1) substituents selected from the group consisting of a halogen atom, $C_1$-$C_6$ alkyl, $C_1$-$C_6$ alkoxy, $C_1$-$C_6$ haloalkyl and $C_1$-$C_6$ haloalkoxy.

In a second particular embodiment, the compound of formula (I) is a compound of formula (Ib) and $R_6$ is H and/or $R_{4a}$ is a group of formula —C(=X)$R_7$, preferably —C(=X)Me, advantageously with X being $NR_8$. Preferably, $R_6$ is H and $R_{4a}$ is a group of formula —C(=X)$R_7$, preferably —C(=X)Me, advantageously with X being $NR_8$. In this particular embodiment, $Ar_1$, $Ar_2$, $Ar_3$, are as defined above, and are advantageously independently a mono or polycyclic $C_5$-$C_{12}$ aryl group, preferably phenyl or naphthyl group, more preferably a phenyl, optionally substituted with 1, 2 or 3 (preferably 1) substituents as listed above for in connection with $Ar_1$, $Ar_2$, $Ar_3$, respectively. Preferably, $Ar_1$, $Ar_2$ and $Ar_3$ are independently a mono or polycyclic $C_5$-$C_{12}$ aryl group, preferably a phenyl group, optionally substituted with 1, 2 or 3 (preferably 1) substituents selected from the group consisting of a halogen atom, $C_1$-$C_6$ alkyl, $C_1$-$C_6$ alkoxy, $C_1$-$C_6$ haloalkyl and $C_1$-$C_6$ haloalkoxy.

For instance, the compound of the invention is:

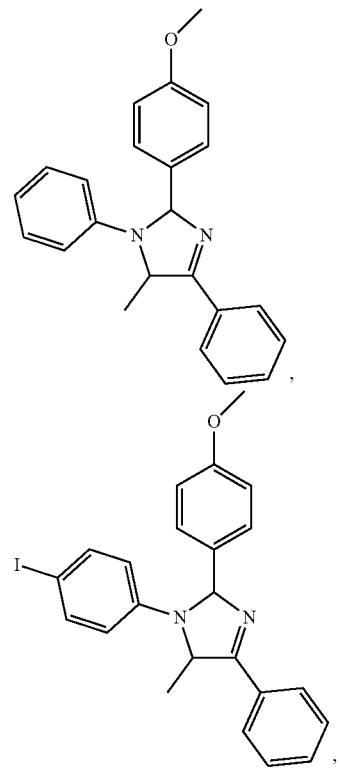

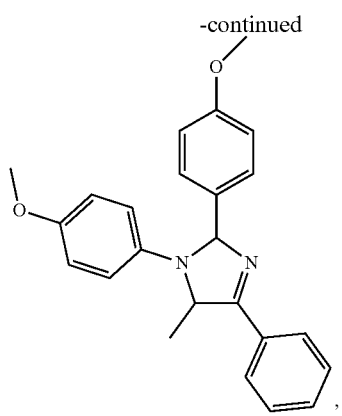
,
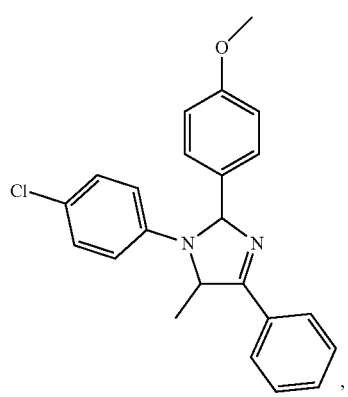
,
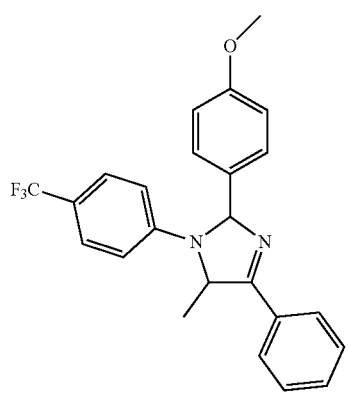
,
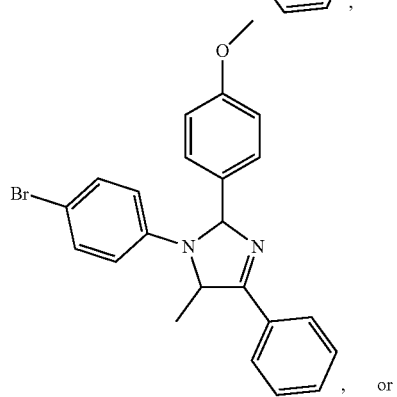
, or
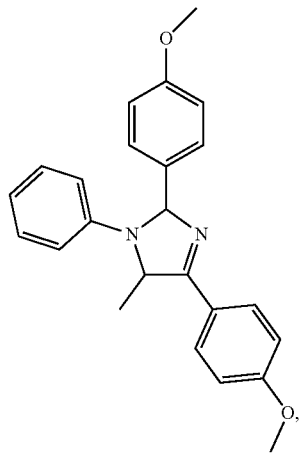
a solvate or a (pharmaceutically acceptable) salt thereof.
The compound of the invention may also be:
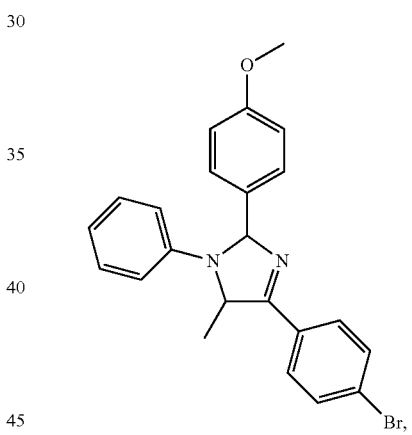
,
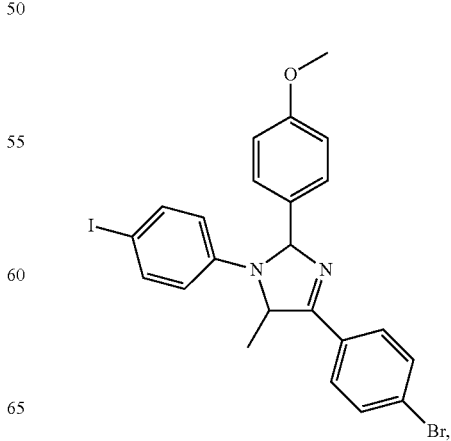
, -continued
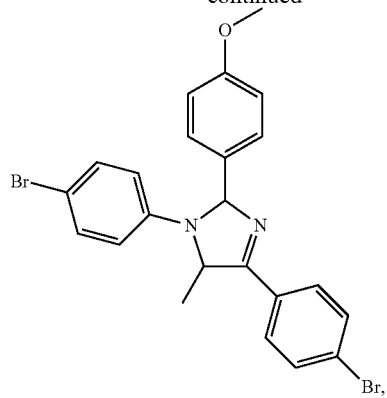
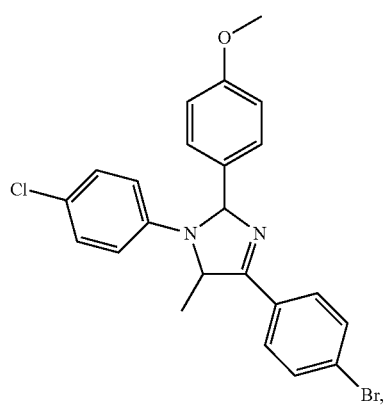
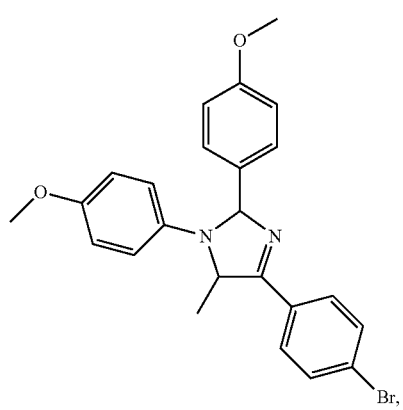
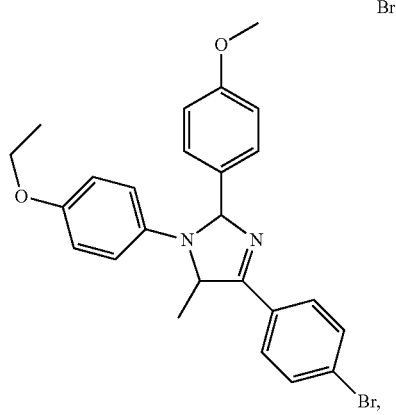
-continued
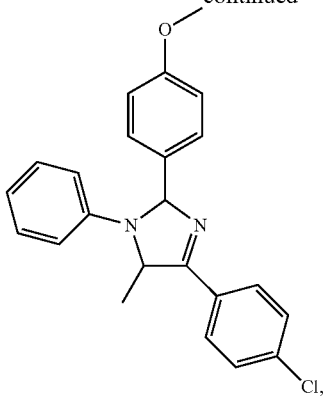
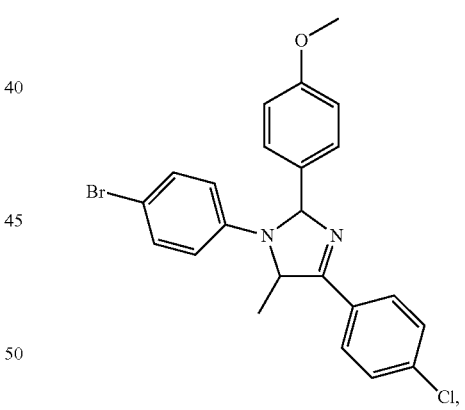
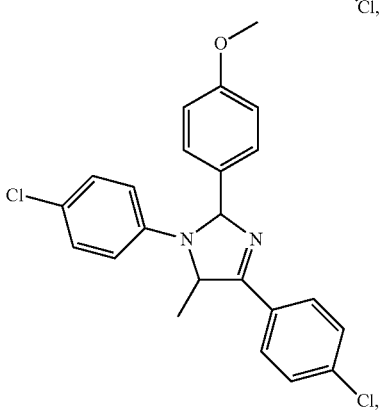

-continued
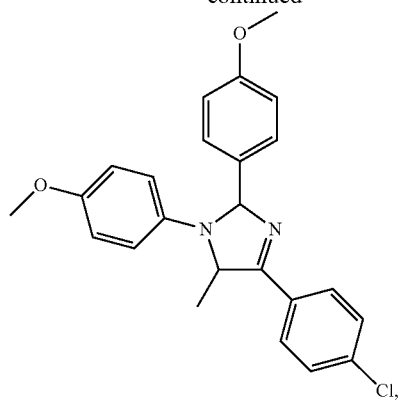
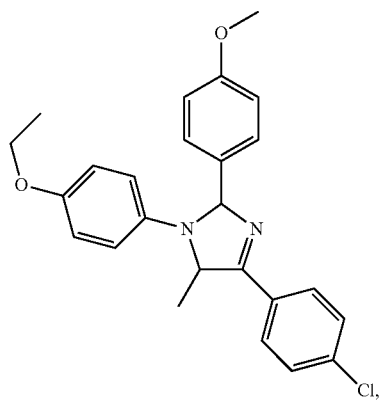
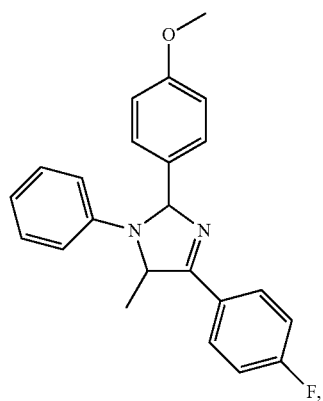
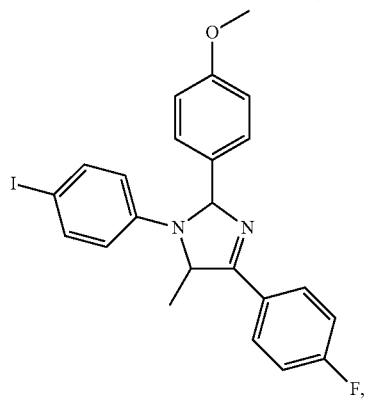
-continued
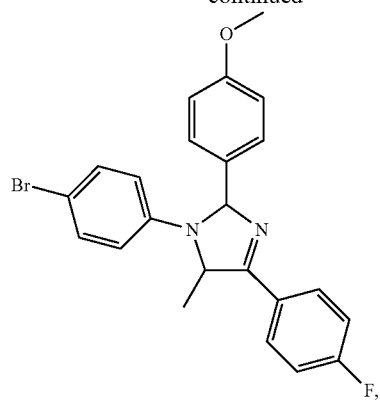
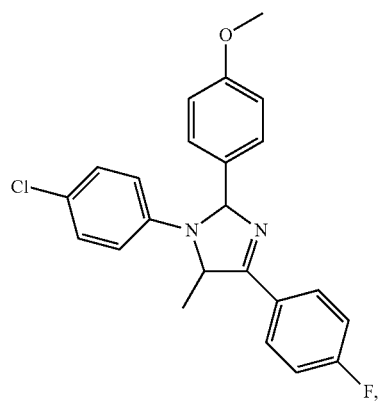
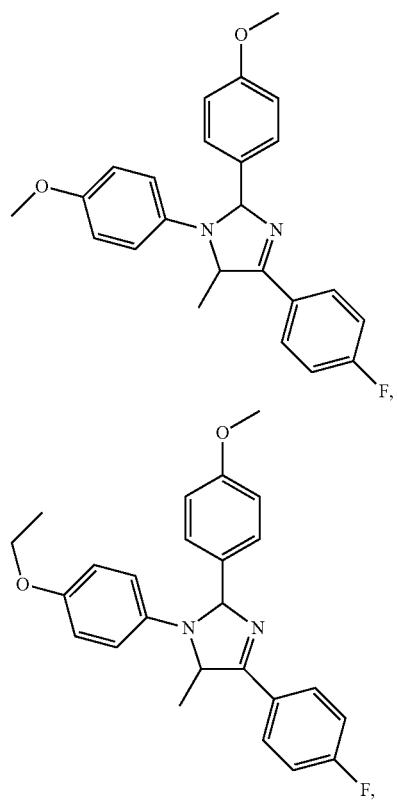

-continued
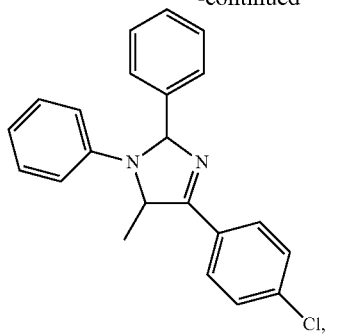
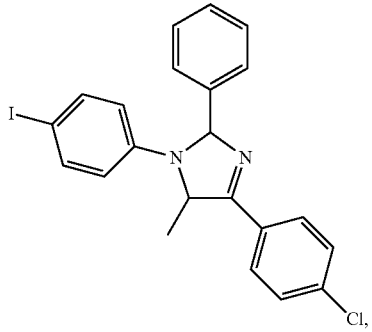
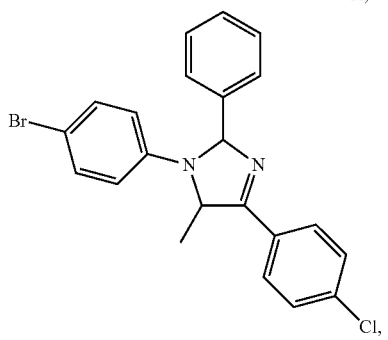
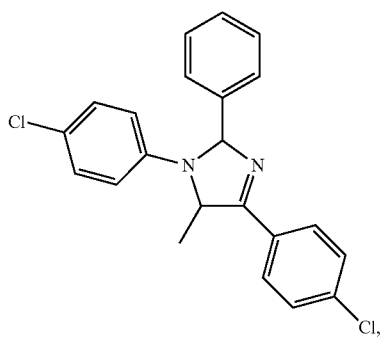
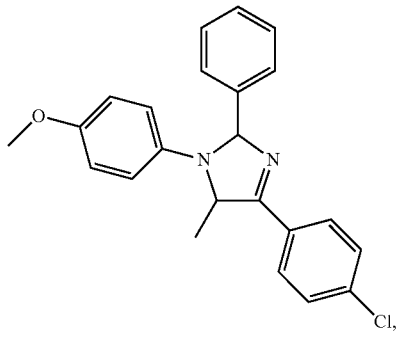
-continued
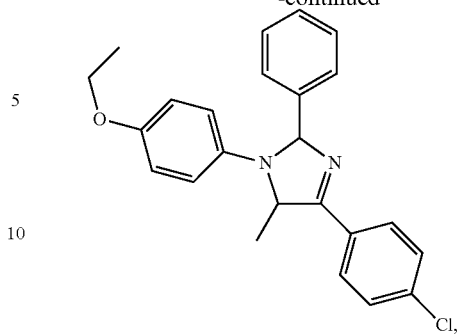
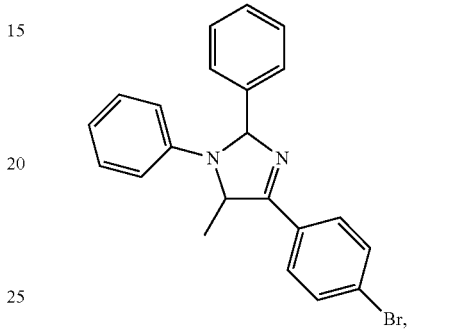
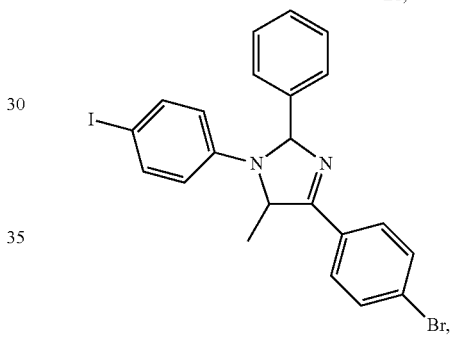
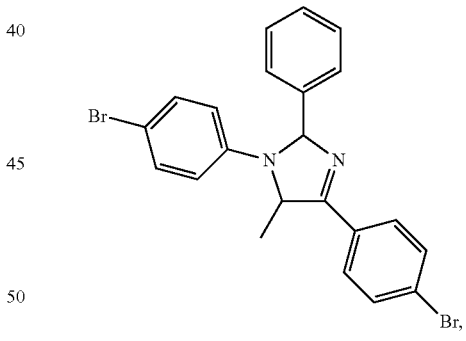
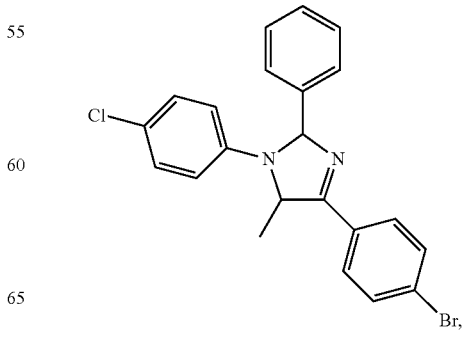

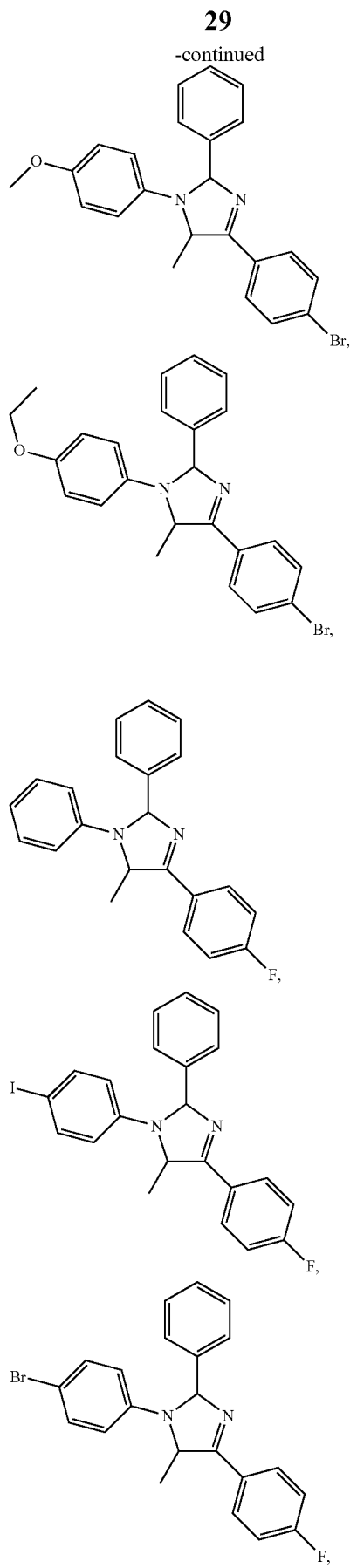
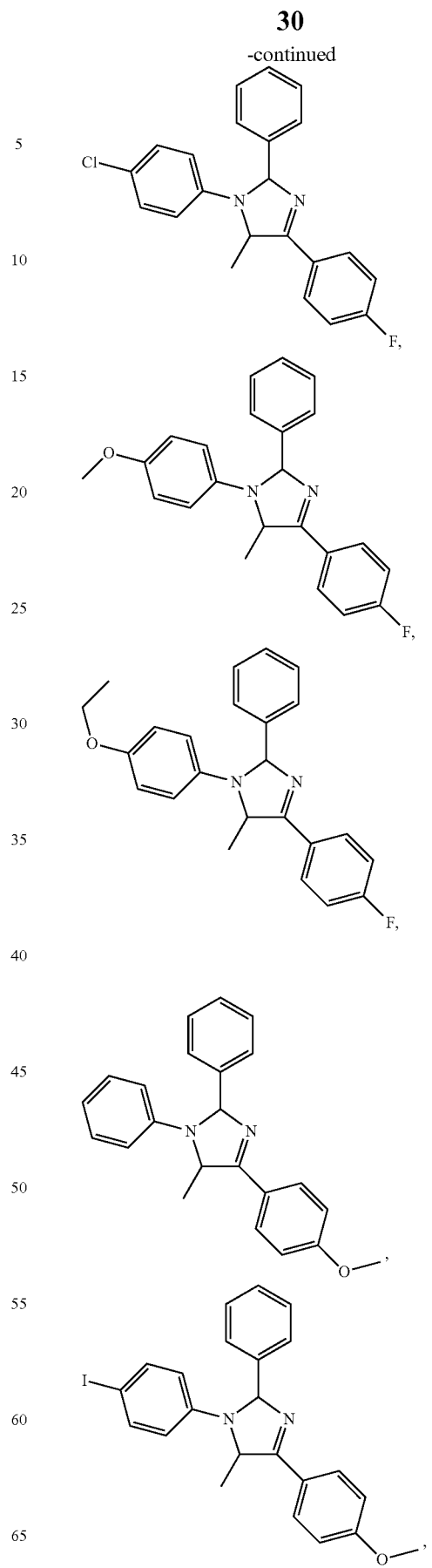

31
-continued
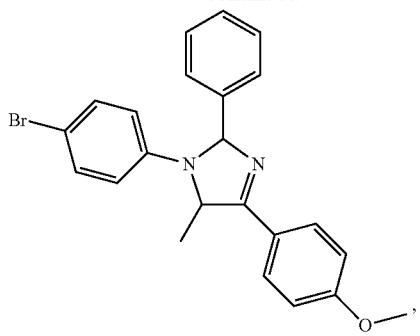
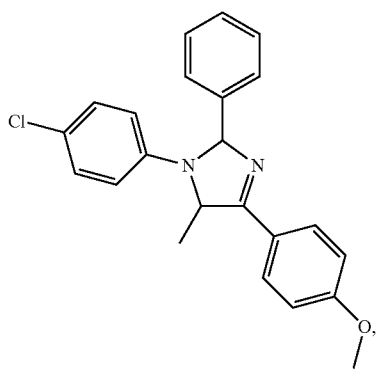
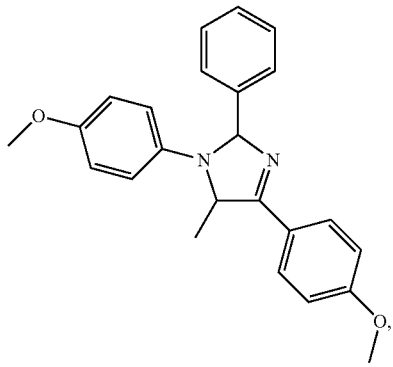
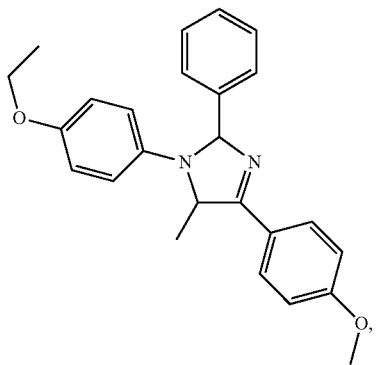
32
-continued
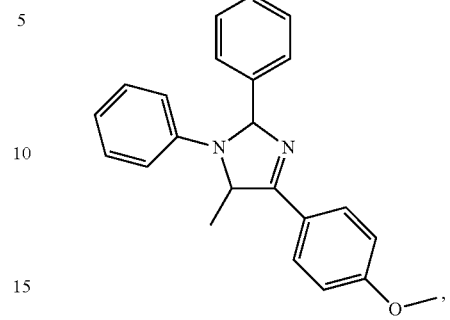
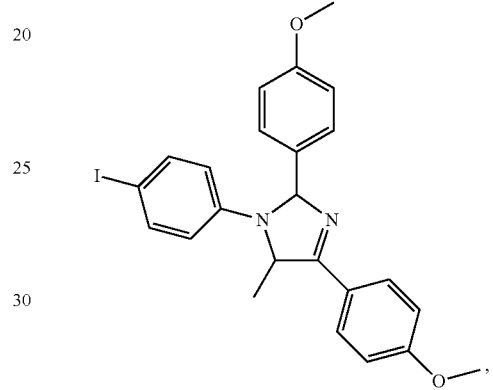
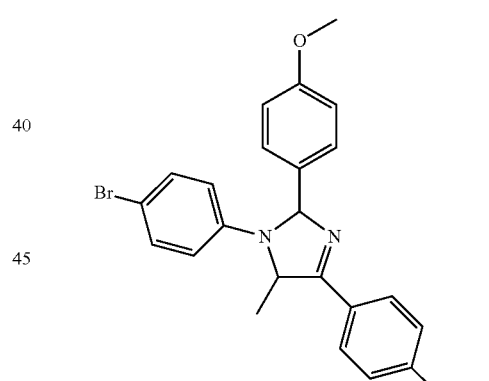
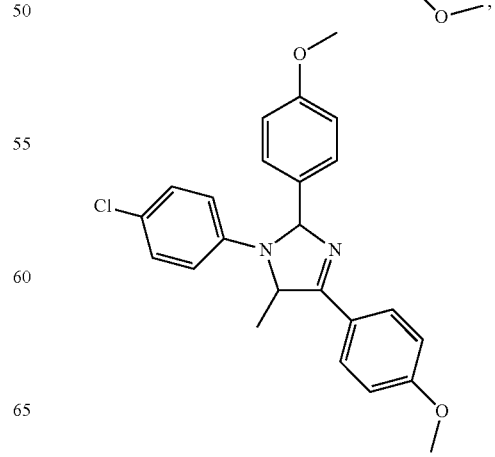

-continued
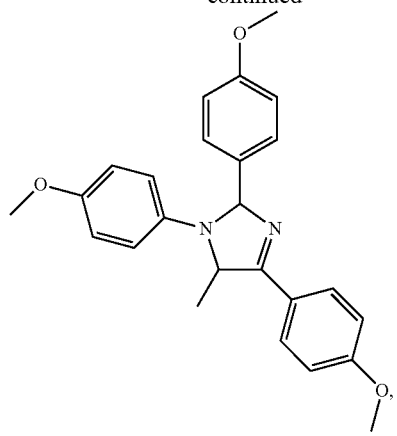
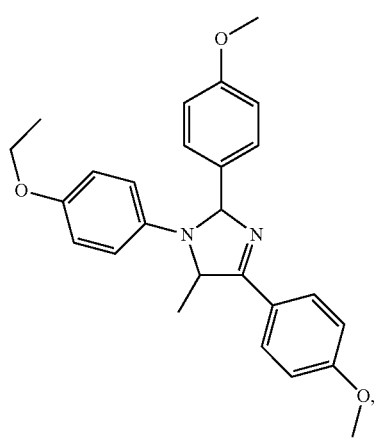
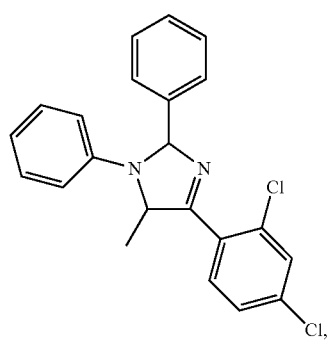
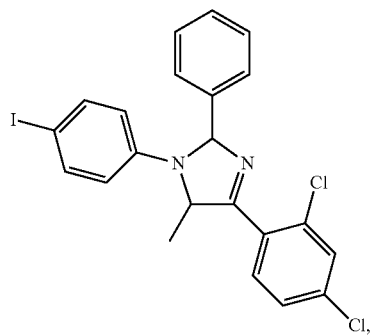
-continued
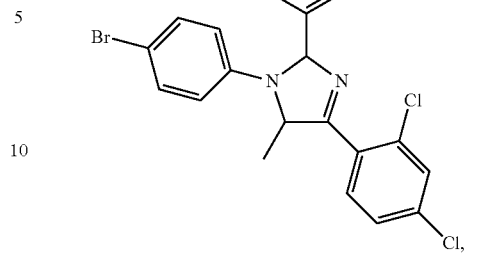
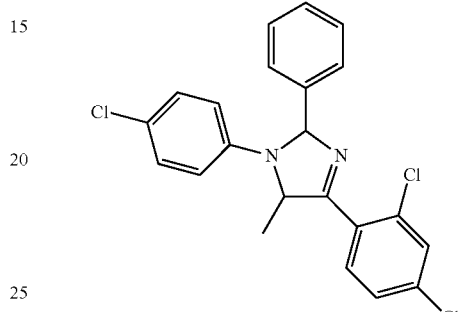
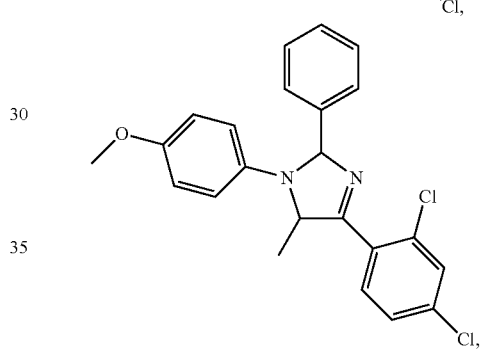
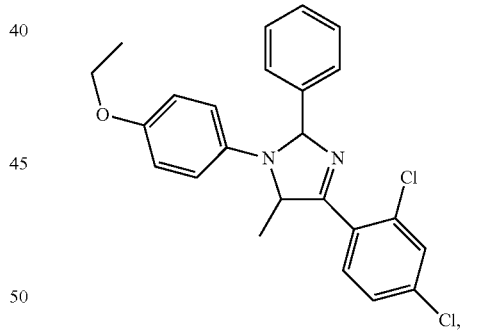
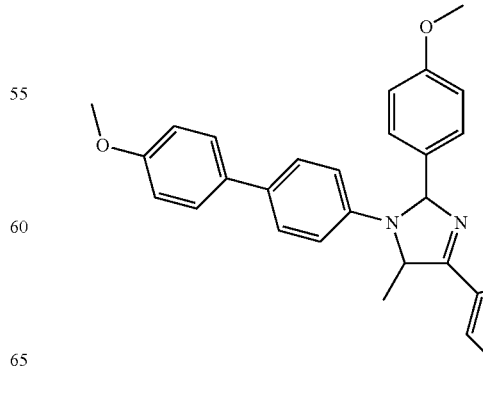

35
-continued
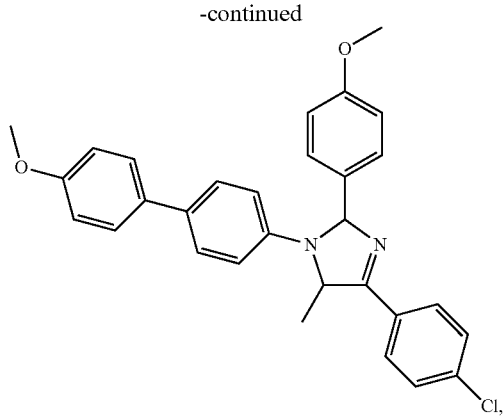
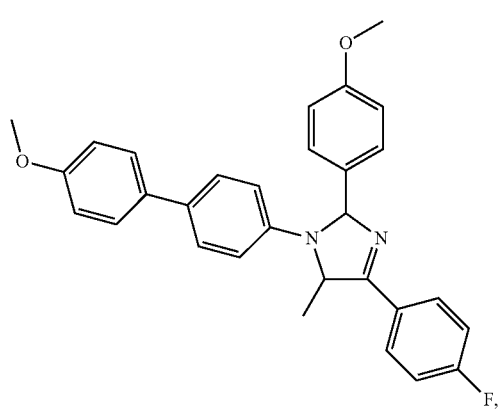
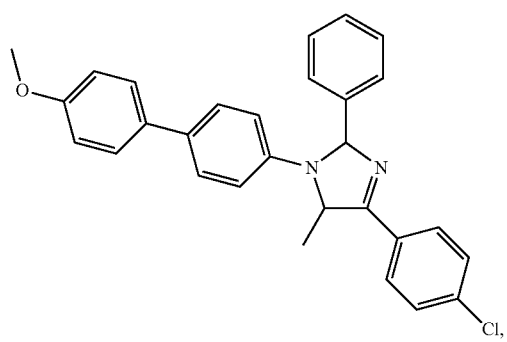
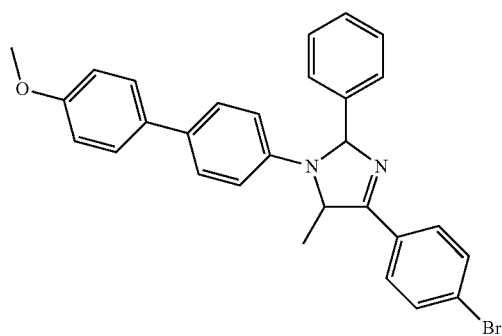
36
-continued
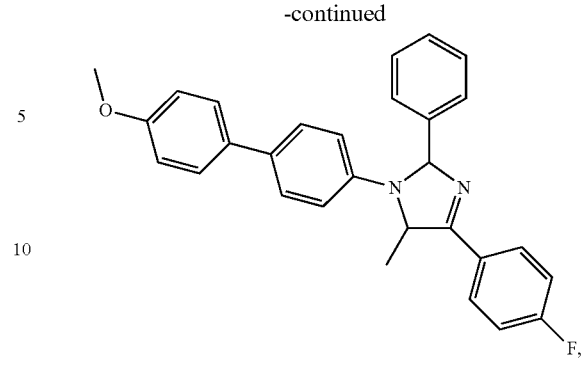
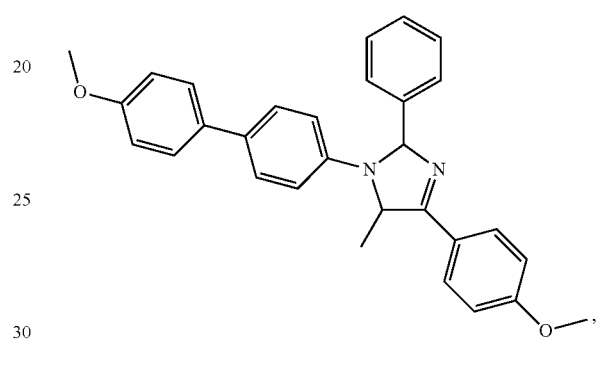
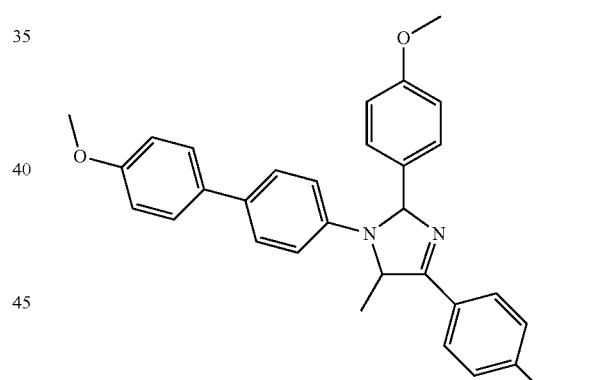
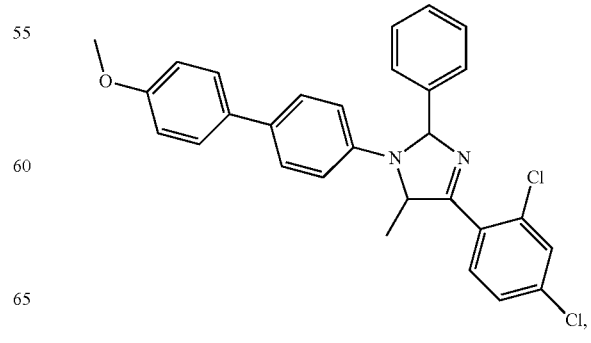

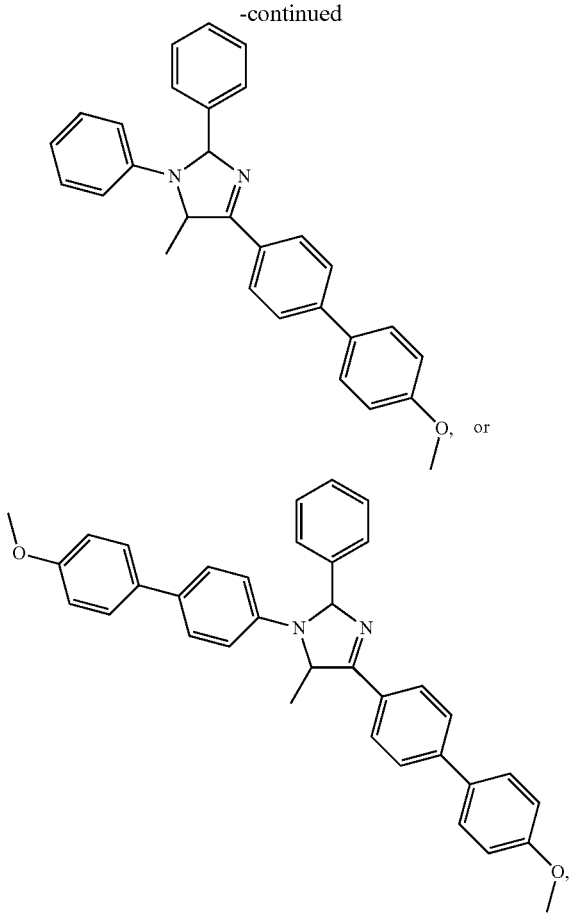

a solvate or a (pharmaceutically acceptable) salt thereof.

The compound of the invention may also be selected from compounds 1 to 31 (cf. examples below) and solvates or (pharmaceutically acceptable) salts thereof.

2. Compounds of Formula (I')

The present invention further relates to compounds of formula (I') as defined above.

The compounds of formula (I') contain several stereogenic centres. They may thus be in the form of mixtures of enantiomers and/or diastereomers.

$R_1$, $R_2$ and $R_3$

In a particular embodiment, $R_1$, $R_2$, and $R_3$ are identical or different, and are independently one from each other $C_1$-$C_{10}$ alkyl, $C_3$-$C_{10}$ cycloalkyl, 3- to 8-membered heterocycle, $C_1$-$C_{10}$ alkoxy, $C_2$-$C_{10}$ alkylcarbonyl, a $C_6$-$C_{13}$ arylcarbonyl, a $C_4$-$C_{13}$ heteroaryl carbonyl, $C_1$-$C_{10}$ haloalkoxy, ($C_1$-$C_6$)-alkoxy-($C_1$-$C_6$)-alkyl, ($C_1$-$C_6$)-haloalkoxy-($C_1$-$C_6$)-alkyl, $C_2$-$C_{10}$ alkylcarbonyl, a $C_6$-$C_{13}$ arylcarbonyl, a $C_4$-$C_{13}$ heteroaryl carbonyl, $C_2$-$C_{10}$ alkenyl, $C_2$-$C_{10}$ alkynyl, $C_2$-$C_{10}$ alkenyloxy, $C_2$-$C_{10}$ alkynyloxy, $C_2$-$C_{10}$ alkenylthio, $C_2$-$C_{10}$ alkynylthio, $C_1$-$C_{10}$ haloalkyl, $C_2$-$C_{10}$ haloalkenyl, $C_2$-$C_{10}$ haloalkynyl, $C_2$-$C_{10}$ haloalkylcarbonyl, $C_2$-$C_{10}$ haloalkenyloxy, $C_2$-$C_{10}$ haloalkynyloxy, ($C_5$-$C_{12}$)-aryl-($C_1$-$C_6$)-alkyl, a ($C_1$-$C_6$)alkyl-($C_5$-$C_{12}$)aryl, a ($C_1$-$C_6$)alkyl-($C_5$-$C_{12}$)heteroaryl, a mono or polycyclic $C_5$-$C_{12}$ aryl or mono or polycyclic $C_3$-$C_{12}$ heteroaryl fragments.

In another particular embodiment, $R_1$, $R_2$, and $R_3$ are identical or different, and are independently one from each other a $C_1$-$C_{10}$ alkyl, $C_3$-$C_{10}$ cycloalkyl, $C_1$-$C_{10}$ alkoxy, $C_2$-$C_{10}$ alkylcarbonyl, a $C_6$-$C_{13}$ arylcarbonyl, a $C_4$-$C_{13}$ heteroaryl carbonyl, $C_1$-$C_{10}$ haloalkoxy, ($C_1$-$C_6$)-alkoxy-($C_1$-$C_6$)-alkyl, ($C_1$-$C_6$)-haloalkoxy-($C_1$-$C_6$)-alkyl, $C_1$-$C_{10}$ thioalkyl, ($C_5$-$C_{12}$)-aryl-($C_1$-$C_6$)-alkyl ester, ($C_1$-$C_6$)-alkylthio-($C_1$-$C_6$)-alkyl, $C_1$-$C_{10}$ alkylsulfinyl, $C_1$-$C_{10}$ haloalkylsulfinyl, $C_1$-$C_{10}$ haloalkylsulfonyl, $C_1$-$C_{10}$ alkylsulfonyl, $C_5$-$C_{12}$ arylsulfonyl, $C_2$-$C_{10}$ alkylcarbonyl, $C_2$-$C_{10}$ alkenyl, $C_2$-$C_{10}$ alkenyloxy, $C_2$-$C_{10}$ alkenylthio, $C_1$-$C_{10}$ haloalkyl, $C_2$-$C_{10}$ haloalkenyl, $C_2$-$C_{10}$ haloalkylcarbonyl, $C_1$-$C_{10}$ haloalkylthio, $C_2$-$C_{10}$ haloalkenyloxy, $C_2$-$C_{10}$ haloalkenylthio, ($C_5$-$C_{12}$)-aryl-($C_1$-$C_6$)-alkyl, a ($C_1$-$C_6$)alkyl-($C_5$-$C_{12}$)aryl, a ($C_1$-$C_6$)alkyl-($C_5$-$C_{12}$)heteroaryl, a mono or polycyclic $C_5$-$C_{12}$ aryl or mono or polycyclic $C_3$-$C_{12}$ heteroaryl fragments.

In another particular embodiment, $R_1$, $R_2$, and $R_3$ are identical or different, and are independently one from each other a $C_1$-$C_{10}$ alkyl, $C_3$-$C_{10}$ cycloalkyl, $C_1$-$C_{10}$ alkoxy, $C_2$-$C_{10}$ alkylcarbonyl, a $C_6$-$C_{13}$ arylcarbonyl, a $C_4$-$C_{13}$ heteroaryl carbonyl, $C_1$-$C_{10}$ haloalkoxy, ($C_1$-$C_6$)-alkoxy-($C_1$-$C_6$)-alkyl, ($C_1$-$C_6$)-haloalkoxy-($C_1$-$C_6$)-alkyl, $C_1$-$C_{10}$ thioalkyl, ($C_5$-$C_{12}$)-aryl-($C_1$-$C_6$)-alkyl ester, ($C_1$-$C_6$)-alkylthio-($C_1$-$C_6$)-alkyl, $C_1$-$C_{10}$ alkylsulfinyl, $C_1$-$C_{10}$ haloalkylsulfinyl, $C_1$-$C_{10}$ haloalkylsulfonyl, $C_1$-$C_{10}$ alkylsulfonyl, $C_5$-$C_{12}$ arylsulfonyl, $C_2$-$C_{10}$ alkylcarbonyl, $C_1$-$C_{10}$ haloalkyl, $C_2$-$C_{10}$ haloalkylcarbonyl, $C_1$-$C_{10}$ haloalkylthio, ($C_5$-$C_{12}$)-aryl-($C_1$-$C_6$)-alkyl, a ($C_1$-$C_6$)alkyl-($C_5$-$C_{12}$)aryl, a ($C_1$-$C_6$)alkyl-($C_5$-$C_{12}$)heteroaryl, a mono or polycyclic $C_5$-$C_{12}$ aryl or mono or polycyclic $C_3$-$C_{12}$ heteroaryl fragments.

In another particular embodiment, $R_1$, $R_2$, and $R_3$ are identical or different, and are independently one from each other a $C_1$-$C_{10}$ alkyl, $C_3$-$C_{10}$ cycloalkyl, $C_1$-$C_{10}$ alkoxy, $C_2$-$C_{10}$ alkylcarbonyl, a $C_6$-$C_{13}$ arylcarbonyl, a $C_4$-$C_{13}$ heteroaryl carbonyl, $C_1$-$C_{10}$ haloalkoxy, ($C_1$-$C_6$)-alkoxy-($C_1$-$C_6$)-alkyl, ($C_1$-$C_6$)-haloalkoxy-($C_1$-$C_6$)-alkyl, ($C_5$-$C_{12}$)-aryl-($C_1$-$C_6$)-alkyl ester, $C_2$-$C_{10}$ alkylcarbonyl, $C_1$-$C_{10}$ haloalkyl, $C_2$-$C_{10}$ haloalkylcarbonyl, ($C_5$-$C_{12}$)-aryl-($C_1$-$C_6$)-alkyl, a ($C_1$-$C_6$)alkyl-($C_5$-$C_{12}$)aryl, a ($C_1$-$C_6$)alkyl-($C_5$-$C_{12}$)heteroaryl, a mono or polycyclic $C_5$-$C_{12}$ aryl or mono or polycyclic $C_3$-$C_{12}$ heteroaryl fragments.

In another particular embodiment, $R_1$, $R_2$, and $R_3$ are identical or different, and at least one of $R_1$, $R_2$, and $R_3$ is a $C_1$-$C_{10}$ haloalkyl, such as a $C_1$-$C_{10}$ fluoroalkyl, for instance a $CF_3$. In particular, $R_1$ may be a $C_1$-$C_{10}$ haloalkyl, such as a $C_1$-$C_{10}$ fluoroalkyl, for instance a $CF_3$.

In another embodiment, $R_1$ is as defined above, but excluding a $CF_3$ group. In another embodiment, $R_1$ is as defined above, but excluding a $C_1$-$C_{10}$ fluoroalkyl, or a $C_1$-$C_{10}$ haloalkyl.

In another particular embodiment, $R_1$, $R_2$, and $R_3$ are identical or different, and at least one of $R_1$, $R_2$, and $R_3$ is a $C_2$-$C_{10}$ alkylcarbonyl, a $C_6$-$C_{13}$ arylcarbonyl or a $C_4$-$C_{13}$ heteroaryl carbonyl. In particular, $R_3$ may be a $C_2$-$C_{10}$ alkylcarbonyl, a $C_6$-$C_{13}$ arylcarbonyl or a $C_4$-$C_{13}$ heteroaryl carbonyl.

In another particular embodiment, $R_3$ is as defined above, but excluding a $CF_3$ group. In another embodiment, $R_1$ is as defined above, but excluding a $C_2$-$C_{10}$ alkylcarbonyl, a $C_6$-$C_{13}$ arylcarbonyl or a $C_4$-$C_{13}$ heteroaryl carbonyl.

In all embodiments, the $C_1$-$C_{10}$ alkyl, $C_3$-$C_{10}$ cycloalkyl, 3- to 8-membered heterocycle, $C_1$-$C_{10}$ alkoxy, $C_2$-$C_{10}$ alkylcarbonyl, a $C_6$-$C_{13}$ arylcarbonyl, a $C_4$-$C_{13}$ heteroaryl carbonyl, $C_1$-$C_{10}$ haloalkoxy, ($C_1$-$C_6$)-alkoxy-($C_1$-$C_6$)-alkyl, ($C_1$-$C_6$)-haloalkoxy-($C_1$-$C_6$)-alkyl, $C_1$-$C_{10}$ thioalkyl, ($C_5$-$C_{12}$)-aryl-($C_1$-$C_6$)-alkyl ester, ($C_1$-$C_6$)-alkylthio-($C_1$-$C_6$)-alkyl, $C_1$-$C_{10}$ alkylsulfinyl, $C_1$-$C_{10}$ haloalkylsulfinyl, $C_1$-$C_{10}$ haloalkylsulfonyl, $C_1$-$C_{10}$ alkylsulfonyl, $C_5$-$C_{12}$ arylsulfonyl, $C_2$-$C_{10}$ alkenyl, $C_2$-$C_{10}$ alkynyl, $C_2$-$C_{10}$ alkenyloxy, $C_2$-$C_{10}$ alkynyloxy, $C_2$-$C_{10}$ alkenylthio, $C_2$-$C_{10}$ alkynylthio, $C_1$-$C_{10}$ haloalkyl, $C_2$-$C_{10}$ haloalkenyl, $C_2$-$C_{10}$ haloalkynyl, $C_2$-$C_{10}$ haloalkylcarbonyl, $C_1$-$C_{10}$ haloalkylthio, $C_2$-$C_{10}$ haloalkenyloxy, $C_2$-$C_{10}$ haloalkynyloxy, $C_2$-$C_{10}$ haloalkenylthio, $C_2$-$C_{10}$ haloalkynylthio, $(C_5$-$C_{12})$-aryl-$(C_1$-$C_6)$-alkyl, a $(C_1$-$C_6)$alkyl-$(C_5$-$C_{12})$aryl, a $(C_1$-$C_6)$alkyl-$(C_5$-$C_{12})$heteroaryl, a mono or polycyclic $C_5$-$C_{12}$ aryl or mono or polycyclic $C_3$-$C_{12}$ heteroaryl fragment (collectively referred to as "the fragments") is optionally substituted with:

one or several (1 to 3, preferably 1 or 2) halogen atoms, hydroxyl (OH), nitro, cyano, formyl, $C_1$-$C_6$ alkyl, $C_3$-$C_7$ cycloalkyl, 3- to 8-membered heterocycle, amino-$C_1$-$C_{10}$ alkoxy, (carboxylic acid)-$C_1$-$C_{10}$ alkoxy, (carboxylic $(C_1$-$C_6)$alkyl ester)-$C_1$-$C_{10}$ alkoxy, (1,2 diol)-$C_2$-$C_{10}$ alkoxy, —O—$(C_1$-$C_6)$alkyl-O—$(C_1$-$C_6)$ alkyl-OH, $(C_1$-$C_6)$-alkoxy-$(C_1$-$C_6)$-alkyl, $C_2$-$C_6$ alkylcarbonyl, $C_1$-$C_6$ alkylthio, $C_1$-$C_6$ thioalkyl, $(C_1$-$C_6)$-alkylthio-$(C_1$-$C_6)$-alkyl, $C_1$-$C_6$ alkylsulfinyl, $C_1$-$C_6$ alkylsulfonyl, $C_1$-$C_6$ haloalkyl, $C_1$-$C_6$ haloalkoxy, $C_1$-$C_6$ haloalkoxy alkyl, $C_2$-$C_6$ haloalkylcarbonyl, $C_1$-$C_6$ haloalkylthio, $C_1$-$C_6$ haloalkylsulfinyl, $C_1$-$C_6$ haloalkylsulfonyl, $C_2$-$C_6$ alkenyl, $C_2$-$C_6$ alkynyl, $C_2$-$C_6$ haloalkynyl, $C_2$-$C_6$ haloalkenyl, $C_2$-$C_6$ haloalkenyloxy, $C_2$-$C_6$ haloalkynyloxy, $C_2$-$C_6$ alkenyloxy, $C_2$-$C_6$ alkynyloxy, $C_2$-$C_6$ alkenylthio, $C_2$-$C_6$ alkynylthio, $C_2$-$C_6$ haloalkenylthio, $C_2$-$C_6$ haloalkynylthio and/or a $C_1$-$C_6$ alkoxy optionally substituted by a mono or polycyclic $C_5$-$C_{12}$ aryl group, a monocyclic $C_5$-$C_6$ aryl group such as a phenyl group, optionally substituted with a $C_1$-$C_6$ alkoxy; and/or a bridging group of formula O—$CH_2$—O— or O—$CH_2CH_2$—O— (the bridging group is in particular contemplated when the fragment contains an aryl or heteroaryl moiety, i.e. when it is a $C_6$-$C_{13}$ arylcarbonyl, a $C_4$-$C_{13}$ heteroaryl carbonyl, $(C_5$-$C_{12})$-aryl-$(C_1$-$C_6)$-alkyl ester, $C_5$-$C_{12}$ arylsulfonyl, $(C_5$-$C_{12})$-aryl-$(C_1$-$C_6)$-alkyl, a $(C_1$-$C_6)$alkyl-$(C_5$-$C_{12})$aryl, a $(C_1$-$C_6)$alkyl-$(C_5$-$C_{12})$heteroaryl, a mono or polycyclic $C_5$-$C_{12}$ aryl or mono or polycyclic $C_3$-$C_{12}$ heteroaryl fragment);

and preferably, the fragments are optionally substituted with:

one or several (1 to 3) halogen atoms, hydroxyl (OH), nitro, cyano, formyl, $C_1$-$C_6$ alkyl, $C_3$-$C_7$ cycloalkyl, 3- to 8-membered heterocycle, amino-$C_1$-$C_{10}$ alkoxy, (carboxylic acid)-$C_1$-$C_{10}$ alkoxy, (carboxylic $(C_1$-$C_6)$ alkyl ester)-$C_1$-$C_{10}$ alkoxy, (1,2 diol)-$C_2$-$C_{10}$ alkoxy, —O—$(C_1$-$C_6)$alkyl-O—$(C_1$-$C_6)$alkyl-OH, $(C_1$-$C_6)$-alkoxy-$(C_1$-$C_6)$-alkyl, $C_2$-$C_6$ alkylcarbonyl, $C_1$-$C_6$ alkylthio, $C_1$-$C_6$ thioalkyl, $(C_1$-$C_6)$-alkylthio-$(C_1$-$C_6)$-alkyl, $C_1$-$C_6$ alkylsulfinyl, $C_1$-$C_6$ alkylsulfonyl, $C_1$-$C_6$ haloalkyl, $C_1$-$C_6$ haloalkoxy, $C_1$-$C_6$ haloalkoxy alkyl, $C_2$-$C_6$ haloalkylcarbonyl, $C_1$-$C_6$ haloalkylthio, $C_1$-$C_6$ haloalkylsulfinyl, $C_1$-$C_6$ haloalkylsulfonyl, $C_2$-$C_6$ alkenyl, $C_2$-$C_6$ alkynyl, $C_2$-$C_6$ haloalkynyl, $C_2$-$C_6$ haloalkenyl, $C_2$-$C_6$ haloalkenyloxy, $C_2$-$C_6$ haloalkynyloxy, $C_2$-$C_6$ alkenyloxy, $C_2$-$C_6$ alkynyloxy, $C_2$-$C_6$ alkenylthio, $C_2$-$C_6$ alkynylthio, $C_2$-$C_6$ haloalkenylthio, $C_2$-$C_6$ haloalkynylthio and/or a $C_1$-$C_6$ alkoxy optionally substituted by a mono or polycyclic $C_5$-$C_{12}$ aryl group, and/or a bridging group of formula O—$CH_2$—O— or O—$CH_2CH_2$—O—.

Of note, the bridging group is in particular contemplated when the fragment contains an aryl or heteroaryl moiety, i.e. when it is a $C_6$-$C_{13}$ arylcarbonyl, a $C_4$-$C_{13}$ heteroaryl carbonyl, $(C_5$-$C_{12})$-aryl-$(C_1$-$C_6)$-alkyl ester, $C_5$-$C_{12}$ arylsulfonyl, $(C_5$-$C_{12})$-aryl-$(C_1$-$C_6)$-alkyl, a $(C_1$-$C_6)$alkyl-$(C_5$-$C_{12})$aryl, a $(C_1$-$C_6)$alkyl-$(C_5$-$C_{12})$heteroaryl, a mono or polycyclic $C_5$-$C_{12}$ aryl or mono or polycyclic $C_3$-$C_{12}$ heteroaryl fragment.

In all embodiments, advantageously, the fragments are optionally substituted with:

one or several (1 to 3) halogen atoms, hydroxyl (OH), nitro, cyano, formyl, $C_1$-$C_6$ alkyl, $C_3$-$C_7$ cycloalkyl, amino-$C_1$-$C_{10}$ alkoxy, (carboxylic acid)-$C_1$-$C_{10}$ alkoxy, (carboxylic $(C_1$-$C_6)$alkyl ester)-$C_1$-$C_{10}$ alkoxy, (1,2 diol)-$C_2$-$C_{10}$ alkoxy, —O—$(C_1$-$C_6)$alkyl-O—$(C_1$-$C_6)$ alkyl-OH, $(C_1$-$C_6)$-alkoxy-$(C_1$-$C_6)$-alkyl, $C_2$-$C_6$ alkylcarbonyl, $C_1$-$C_6$ haloalkyl, $C_1$-$C_6$ haloalkoxy, $C_1$-$C_6$ haloalkoxy alkyl, $C_2$-$C_6$ haloalkylcarbonyl, $C_2$-$C_6$ alkenyl, $C_2$-$C_6$ alkynyl, $C_2$-$C_6$ haloalkynyl, $C_2$-$C_6$ haloalkenyl, $C_2$-$C_6$ haloalkenyloxy, $C_2$-$C_6$ haloalkynyloxy, $C_2$-$C_6$ alkenyloxy, $C_2$-$C_6$ alkynyloxy, and/or a $C_1$-$C_6$ alkoxy optionally substituted by a mono or polycyclic $C_5$-$C_{12}$ aryl group;

a monocyclic $C_5$-$C_6$ aryl group such as a phenyl group, optionally substituted with a $C_1$-$C_6$ alkoxy; and/or a bridging group of formula O—$CH_2$—O— or O—$CH_2CH_2$—O—.

In all embodiments, preferably, the fragments are optionally substituted with:

one or several (1 to 3) halogen atoms, hydroxyl (OH), nitro, cyano, formyl, $C_1$-$C_6$ alkyl, $C_3$-$C_7$ cycloalkyl, amino-$C_1$-$C_{10}$ alkoxy, (carboxylic acid)-$C_1$-$C_{10}$ alkoxy, (carboxylic $(C_1$-$C_6)$alkyl ester)-$C_1$-$C_{10}$ alkoxy, (1,2 diol)-$C_2$-$C_{10}$ alkoxy, —O—$(C_1$-$C_6)$alkyl-O—$(C_1$-$C_6)$ alkyl-OH, $(C_1$-$C_6)$-alkoxy-$(C_1$-$C_6)$-alkyl, $C_2$-$C_6$ alkylcarbonyl, $C_1$-$C_6$ haloalkyl, $C_1$-$C_6$ haloalkoxy, $C_1$-$C_6$ haloalkoxy alkyl, $C_2$-$C_6$ haloalkylcarbonyl, $C_2$-$C_6$ alkenyl, $C_2$-$C_6$ alkynyl, $C_2$-$C_6$ haloalkynyl, $C_2$-$C_6$ haloalkenyl, $C_2$-$C_6$ haloalkenyloxy, $C_2$-$C_6$ haloalkynyloxy, $C_2$-$C_6$ alkenyloxy, $C_2$-$C_6$ alkynyloxy, and/or a $C_1$-$C_6$ alkoxy optionally substituted by a mono or polycyclic $C_5$-$C_{12}$ aryl group, and/or a bridging group of formula O—$CH_2$—O— or O—$CH_2CH_2$—O—.

In all embodiments, preferably, the fragments are optionally substituted with one or several (1 to 3) halogen atoms, hydroxyl (OH), $C_1$-$C_6$ alkyl, $C_3$-$C_7$ cycloalkyl, amino-$C_1$-$C_{10}$ alkoxy, (carboxylic acid)-$C_1$-$C_{10}$ alkoxy, (carboxylic $(C_1$-$C_6)$alkyl ester)-$C_1$-$C_{10}$ alkoxy, (1,2 diol)-$C_2$-$C_{10}$ alkoxy, —O—$(C_1$-$C_6)$alkyl-O—$(C_1$-$C_6)$alkyl-OH, $(C_1$-$C_6)$-alkoxy-$(C_1$-$C_6)$-alkyl, $C_2$-$C_6$ alkylcarbonyl, $C_1$-$C_6$ haloalkyl, $C_1$-$C_6$ haloalkoxy, $C_1$-$C_6$ haloalkoxy alkyl, $C_2$-$C_6$ haloalkylcarbonyl, and/or a $C_1$-$C_6$ alkoxy optionally substituted by a mono or polycyclic $C_5$-$C_{12}$ aryl group.

In all embodiments, when the fragment contains an aryl moiety, said aryl moiety may be substituted with a bridging group of formula O—$CH_2$—O— or O—$CH_2CH_2$—O—.

In a particular embodiment, $R_1$ represents $Ar_1$ (as defined above in connection with the compounds of formula (I)). In another particular embodiment, $R_2$ represents $Ar_2$ (as defined above in connection with the compounds of formula (I)). In another particular embodiment, $R_3$ represents $Ar_3$ (as defined above in connection with the compounds of formula (I)). In another particular embodiment, $R_1$ represents $Ar_1$ and $R_2$ represents $Ar_2$. In another particular embodiment, $R_1$ represents $Ar_1$ and $R_3$ represents $Ar_3$. In another particular embodiment, $R_2$ represents $Ar_2$ and $R_3$ represents $Ar_3$. In another particular embodiment, $R_1$ represents $Ar_1$, $R_2$ represents $Ar_2$, and $R_3$ represents $Ar_3$.

$R_4$

Preferably, $R_4$ is as defined above in connection with the compounds of formula (I).

$R_{4a}$

Preferably, $R_{4a}$ is as defined above in connection with the compounds of formula (I).

$R_5$

In $R_5$, each $C_1$-$C_{10}$ alkyl, $C_3$-$C_{10}$ cycloalkyl, 3- to 8-membered heterocycle, $C_1$-$C_{10}$ alkoxy, $C_1$-$C_{10}$ haloalkoxy, ($C_1$-$C_6$)-alkoxy-($C_1$-$C_6$)-alkyl, ($C_1$-$C_6$)-haloalkoxy-($C_1$-$C_6$)-alkyl, $C_1$-$C_{10}$ thioalkyl, ($C_1$-$C_6$)-alkylthio-($C_1$-$C_6$)-alkyl, $C_1$-$C_{10}$ alkylsulfinyl, $C_1$-$C_{10}$ haloalkylsulfinyl, $C_1$-$C_{10}$ haloalkylsulfonyl, $C_1$-$C_{10}$ alkylsulfonyl, $C_5$-$C_{12}$ arylsulfonyl, $C_2$-$C_{10}$ alkylcarbonyl, $C_2$-$C_{10}$ alkenyl, $C_2$-$C_{10}$ alkynyl, $C_2$-$C_{10}$ alkenyloxy, $C_2$-$C_{10}$ alkynyloxy, $C_2$-$C_{10}$ alkenylthio, $C_2$-$C_{10}$ alkynylthio, $C_1$-$C_{10}$ haloalkyl, $C_2$-$C_{10}$ haloalkenyl, $C_2$-$C_{10}$ haloalkynyl, $C_2$-$C_{10}$ haloalkylcarbonyl, $C_1$-$C_{10}$ haloalkylthio, $C_2$-$C_{10}$ haloalkenyloxy, $C_2$-$C_{10}$ haloalkynyloxy, $C_2$-$C_{10}$ haloalkenylthio, $C_2$-$C_{10}$ haloalkynylthio, ($C_5$-$C_{12}$)-aryl-($C_1$-$C_6$)-alkyl, ($C_5$-$C_{12}$)-aryl-($C_1$-$C_6$)-alkyl ester, ($C_1$-$C_6$)-alkyl-($C_5$-$C_{12}$)-aryl, ($C_1$-$C_6$)-alkyl-($C_3$-$C_{12}$)-heteroaryl, mono or polycyclic $C_5$-$C_{12}$ aryl and mono or polycyclic $C_3$-$C_{12}$ heteroaryl group is optionally substituted with 1 to 3 substituents independently selected from the group consisting of: halogen atoms, hydroxyl (OH), nitro, cyano, formyl, $C_3$-$C_7$ cycloalkyl, $C_1$-$C_6$-alkoxy, amino, $C_1$-$C_6$ alkylamino, di($C_1$-$C_6$)alkylamino, COOH, COO—($C_1$-$C_6$)alkyl, $CONH_2$, $CONH(C_1$-$C_6$)alkyl, $C_1$-$C_6$ thioalkyl, SH, $S(C_1$-$C_6$)alkyl, $S(O)(C_1$-$C_6$)alkyl, $S(O_2)(C_1$-$C_6$)alkyl, and a mono or polycyclic $C_5$-$C_{12}$ aryl group.

In a particular embodiment, $R_5$ is a hydrogen atom, halogen atom, $C_1$-$C_{10}$ alkyl, $C_3$-$C_{10}$ cycloalkyl, $C_1$-$C_{10}$ alkoxy, $C_1$-$C_{10}$ haloalkoxy, ($C_1$—$O_6$)-alkoxy-($C_1$—$O_6$)-alkyl, ($C_1$—$O_6$)-haloalkoxy-($C_1$-$C_6$)-alkyl, $C_1$-$C_{10}$ thioalkyl, ($C_1$-$C_6$)-alkylthio-($C_1$-$C_6$)-alkyl, $C_1$-$C_{10}$ alkylsulfinyl, $C_1$-$C_{10}$ haloalkylsulfinyl, $C_1$-$C_{10}$ haloalkylsulfonyl, $C_1$-$C_{10}$ alkylsulfonyl, $C_5$-$C_{12}$ arylsulfonyl, formyl, $C_2$-$C_{10}$ alkenyl, $C_2$-$C_{10}$ alkenyloxy, $C_2$-$C_{10}$ alkenylthio, $C_1$-$C_{10}$ haloalkyl, $C_2$-$C_{10}$ haloalkenyl, $C_1$-$C_{10}$ haloalkylthio, $C_2$-$C_{10}$ haloalkenyloxy, $C_2$-$C_{10}$ haloalkenylthio, ($C_5$-$C_{12}$)-aryl-($C_1$-$C_6$)-alkyl, ($C_5$-$C_{12}$)-aryl-($C_1$-$C_5$)-alkyl ester, a mono or polycyclic $C_5$-$C_{12}$ aryl, or mono or polycyclic $C_3$-$C_{12}$ heteroaryl group, optionally substituted. Preferably, each $C_1$-$C_{10}$ alkyl, $C_3$-$C_{10}$ cycloalkyl, $C_1$-$C_{10}$ alkoxy, $C_1$-$C_{10}$ haloalkoxy, ($C_1$-$C_6$)-alkoxy-($C_1$-$C_6$)-alkyl, ($C_1$-$C_6$)-haloalkoxy-($C_1$-$C_6$)-alkyl, $C_1$-$C_{10}$ thioalkyl, ($C_1$-$C_6$)-alkylthio-($C_1$-$C_6$)-alkyl, $C_1$-$C_{10}$ alkylsulfinyl, $C_1$-$C_{10}$ haloalkylsulfinyl, $C_1$-$C_{10}$ haloalkylsulfonyl, $C_1$-$C_{10}$ alkylsulfonyl, $C_5$-$C_{12}$ arylsulfonyl, formyl, $C_2$-$C_{10}$ alkenyl, $C_2$-$C_{10}$ alkenyloxy, $C_2$-$C_{10}$ alkenylthio, $C_1$-$C_{10}$ haloalkyl, $C_2$-$C_{10}$ haloalkenyl, $C_1$-$C_{10}$ haloalkylthio, $C_2$-$C_{10}$ haloalkenyloxy, $C_2$-$C_{10}$ haloalkenylthio, ($C_5$-$C_{12}$)-aryl-($C_1$-$C_6$)-alkyl, ($C_5$-$C_{12}$)-aryl-($C_1$-$C_6$)-alkyl ester, ($C_1$-$C_6$)-alkyl-($C_5$-$C_{12}$)-aryl, ($C_1$-$C_6$)-alkyl-($C_3$-$C_{12}$)-heteroaryl, a mono or polycyclic $C_5$-$C_{12}$ aryl, or mono or polycyclic $C_3$-$C_{12}$ heteroaryl group is optionally substituted with 1 to 3 substituents independently selected from the group consisting of: halogen atoms, hydroxyl (OH), $C_1$-$C_6$-alkoxy, amino, $C_1$-$C_6$-alkylamino, di($C_1$-$C_6$)alkylamino, COOH, COO—($C_1$-$C_6$)alkyl, $CONH_2$, $CONH(C_1$-$C_6$)alkyl, $C_1$-$C_6$ thioalkyl, SH, $S(O)(C_1$-$C_6$)alkyl, $S(O_2)(C_1$-$C_6$)alkyl, and a mono $C_5$-$C_6$ aryl group.

In a particular embodiment, $R_5$ is a hydrogen atom or a linear $C_1$-$C_6$ alkyl group optionally substituted with 1 to 3 substituents independently selected from the group consisting of:

halogen atoms, hydroxyl (OH), $C_1$-$C_6$-alkoxy, amino, $C_1$-$C_6$-alkylamino, di($C_1$-$C_6$)alkylamino, COOH, COO— ($C_1$-$C_6$)alkyl, $CONH_2$, $CONH(C_1$-$C_6$)alkyl, $C_1$-$C_6$ thioalkyl, SH, $S(O)(C_1$-$C_6$)alkyl, $S(O_2)(C_1$-$C_6$)alkyl, and a mono $C_5$-$C_6$ aryl group.

In a particular embodiment, $R_5$ is a hydrogen atom or a linear $C_1$-$C_4$ alkyl group optionally substituted with 1 to 3 substituents independently selected from the group consisting of: halogen atoms, hydroxyl (OH), linear $C_1$-$C_6$-alkoxy, amino, linear $C_1$-$C_6$-alkylamino, di(linear $C_1$-$C_6$)alkylamino, linear $C_1$-$C_6$ thioalkyl, SH, linear $S(O)(C_1$-$C_6$)alkyl, linear $S(O_2)(C_1$-$C_6$)alkyl.

In a particular embodiment, $R_5$ represents —$CH_2R_6$ (wherein $R_6$ as defined above in connection with the compounds of formula (I)). Preferably, $R_5$ is $CH_3$.

In a preferred embodiment, $R_6$ is a methyl group or H. Most preferably, $R_6$ is H.

Combinations

Any combinations of particular and/or preferred embodiments of $R_1$, $R_2$, $R_3$, $R_4$, $R_{4a}$ and $R_5$ are encompassed by the present invention.

In a particular embodiment, $R_1$, $R_2$, $R_3$ are identical or different, and at least one of $R_1$, $R_2$ and $R_3$ is a mono or polycyclic $C_5$-$C_{12}$ aryl and mono or polycyclic $C_3$-$C_{12}$ heteroaryl group, optionally substituted with 1 to 3 substituents independently selected from the group consisting of: halogen atoms, hydroxyl (OH), nitro, cyano, formyl, $C_3$-$C_7$ cycloalkyl, $C_1$-$C_6$-alkoxy, amino, $C_1$-$C_6$ alkylamino, di($C_1$-$C_6$)alkylamino, COOH, COO—($C_1$-$C_6$)alkyl, $CONH_2$, $CONH(C_1$-$C_6$)alkyl, $C_1$-$C_6$ thioalkyl, SH, $S(C_1$-$C_6$)alkyl, $S(O)(C_1$-$C_6$)alkyl, $S(O_2)(C_1$-$C_6$)alkyl, and a mono or polycyclic $C_5$-$C_{12}$ aryl group.

In another particular embodiment, $R_1$, $R_2$, $R_3$ are identical or different, and at least two of $R_1$, $R_2$ and $R_3$ are independently a mono or polycyclic $C_5$-$C_{12}$ aryl and mono or polycyclic $C_3$-$C_{12}$ heteroaryl group, optionally substituted with 1 to 3 substituents independently selected from the group consisting of: halogen atoms, hydroxyl (OH), nitro, cyano, formyl, $C_3$-$C_7$ cycloalkyl, $C_1$-$C_6$-alkoxy, amino, $C_1$-$C_6$ alkylamino, di($C_1$-$C_6$)alkylamino, COOH, COO— ($C_1$-$C_6$)alkyl, $CONH_2$, $CONH(C_1$-$C_6$)alkyl, $C_1$-$C_6$ thioalkyl, SH, $S(C_1$-$C_6$)alkyl, $S(O)(C_1$-$C_6$)alkyl, $S(O_2)(C_1$-$C_6$) alkyl, and a mono or polycyclic $C_5$-$C_{12}$ aryl group.

In another particular embodiment, the compound of formula (I') is a compound of formula (I'a) and at least one of $R_4$ is H and $R_5$ is $CH_3$. For instance, $R_4$ is H and/or $R_5$ is $CH_3$, while $R_1$, $R_2$, $R_3$, identical or different, are as defined above. In this particular embodiment, $R_1$, $R_2$, $R_3$ are advantageously independently a mono or polycyclic $C_5$-$C_{12}$ aryl group, preferably phenyl or naphthyl group, more preferably a phenyl, optionally substituted with 1, 2 or 3 (preferably 1) substituents as listed above for in connection with $R_1$, $R_2$, $R_3$, respectively. Preferably, $R_1$, $R_2$, $R_3$ are independently a mono or polycyclic $C_5$-$C_{12}$ aryl group, preferably a phenyl group, optionally substituted with 1, 2 or 3 (preferably 1) substituents selected from the group consisting of a halogen atom, $C_1$-$C_6$ alkyl, $C_1$-$C_6$ alkoxy, $C_1$-$C_6$ haloalkyl and $C_1$-$C_6$ haloalkoxy.

In another particular embodiment, the compound of formula (I') is a compound of formula (I'b) and $R_5$ is $CH_3$ and/or $R_{4a}$ is a group of formula —C(=X)$R_7$, preferably —C(=X)Me, advantageously with X being $NR_8$. For instance, $R_5$ is $CH_3$, $R_{4a}$ is a group of formula —C(=X)$R_7$, preferably —C(=X)Me, advantageously with X being NRs, while $R_1$, $R_2$, $R_3$, identical or different, are as defined above. In this particular embodiment, $R_1$, $R_2$, $R_3$ are advantageously independently a mono or polycyclic $C_5$-$C_{12}$ aryl group, preferably phenyl or naphthyl group, more preferably a phenyl, optionally substituted with 1, 2 or 3 (preferably 1) substituents as listed above for in connection with $R_1$, $R_2$, $R_3$, respectively. Preferably, $R_1$, $R_2$, $R_3$ are independently a mono or polycyclic $C_5$-$C_{12}$ aryl group, preferably a phenyl group, optionally substituted with 1, 2 or 3 (preferably 1) substituents selected from the group consisting of a halogen atom, $C_1$-$C_6$ alkyl, $C_1$-$C_6$ alkoxy, $C_1$-$C_6$ haloalkyl and $C_1$-$C_6$ haloalkoxy.

3. Method for Preparing the Compounds of Formula (I) and (I')

The compounds of formula (I) and (I') may be prepared using various methods known in the literature, such as the method described in patent application DE 1 069 635, or the method described by Kirchner et al. (Justus Liebigs Ann. Chem., 625, 98-103 (1959)), or Steglich et al. (Chem. Ber. 113, 770-786 (1980)).

However, the Inventors have developed a new method for preparing the compounds of formula (I) in particular.

Therefore, the present invention concerns a method for preparing a compound of formula (I) as defined above, comprising the following successive steps:

a) a compound of formula (II):

(II)

with $Ar_3$ and $R_6$ as defined above and LG a leaving group, is added to a compound of formula (III), such as a compound of formula (IIIa):

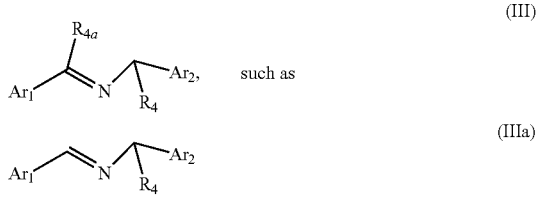

such as (III)

(IIIa)

with $Ar_1$, $Ar_2$ and $R_4$ as defined above, in the presence of a base;

b) isolating the compound of formula (I) as defined above.

Preferably, $R_4$ and $R_6$ have the same definitions in formula (II) as in the case of formula (I) with, if need be, protecting groups on the reacting functions thereof.

LG preferably is an electron-withdrawing group such as a carbamate, a sulfonamide, an amide and or a sulfonyle. More preferably, LG is chosen in the group consisting of Boc (i.e. tert-butyloxycarbonyl), acetamide, mesylate or tosylate. In particular, LG is a carbamate such as a Boc group.

Preferably, the molar ratio compound of formula (II)/compound of formula (III) is greater than 1, more preferably it is equal to or greater than 1.5. For instance, the compound of formula (II)/compound of formula (III) molar ratio is of between 2 and 10.

The addition of step (a) occurs in the presence of a base, which will be referred to as B1. Preferably, B1 is a hydroxide salt or $C_1$-$C_6$ alkoxide salt or a phenoxide salt, in particular a hydroxide salt or tert-butoxide salt, a methoxide salt or a phenoxide salt, typically with an alkaline metal ion such as $Li^+$, $Na^+$ or $K^+$. Preferably, B1 is a tert-butoxide salt such as t-BuONa, t-BuOLi, t-BuOK or t-BuONa. Most preferably B1 is t-BuOLi.

The base B1 is typically in excess, that is, the molar ratio B1/compound of formula (III) (and/or B1/compound of formula (II)) is greater than 1. In other words, B1 is added in a quantity greater than 1.5 equivalents, with respect to the compound of formula (III) (in moles). More preferably, B1 is added in a quantity of between 2 equivalents and 10 equivalents with respect to compound (III).

In a particular embodiment, the equivalents of B1 are the same as the equivalents of compound (II).

The addition of step (a) is typically performed in the presence of a polar solvent, such as dimethylformamide ("DMF"), preferably with a content of water of less than 5% molar, more preferably with a content of water of less than 1% molar (i.e. "dry"), yet in a more preferable embodiment substantially without any water (i.e. "extra dry"). In the most preferred embodiment, step (a) is performed in dry or extra dry DMF.

In a preferred embodiment, the addition of step (a) is performed under heating, advantageously under microwave heating, preferably for a period of time comprised between 1 minute and 24 hours, more preferably between 5 minutes and 5 hours, even more preferably between 10 minutes and 1 hour, such as around (±5 minutes) 20 minutes, 30 minutes, 40 minutes or 50 minutes.

In a preferred embodiment, step (a) is performed in the presence of silica, preferably in the presence of between 0.5 and 5 equivalents of silica with respect to the compound of formula (III). More preferably, step (a) is performed in the presence of between 0.8 and 2 equivalents of silica with respect to the compound of formula (III). In yet a more preferred embodiment, step (a) is performed in the presence of around (±0.1 equivalent) 1 equivalent of silica.

Preferably, the reaction of step (a) is performed under pressure and/or at a temperature above 50° C. For instance, the pressure is greater than 1.5 bar, more preferably greater than 2 bar, even more preferably greater than 3 bar. In this embodiment, heating may be provided either by microwave or by conventional heating.

The temperature of the reaction of step (a) is preferably greater than 60° C., more preferably greater than 75° C., even more preferably greater than 85° C. In a particular preferred embodiment of the present invention, the temperature of step (a) is around 100° C., i.e. 100° C.±5° C. When performed under microwaves, the temperature is preferably maintained at a temperature of around 100° C., i.e. 100° C.±5° C. for a set period of time of between 1 minute and 24 hours, more preferably between 5 minutes and 5 hours, even more preferably between 10 minutes and 1 hour, such as around (±5 minutes) 20 minutes, 30 minutes, 40 minutes or 50 minutes.

Typically, the method of preparation of the invention is carried out in the absence of metals or metallic salts such as copper, copper salts, under oxidized or reduced forms.

In a particular embodiment, step a) comprises the addition of a compound of formula (II) with a compound of formula (III) as defined above, in the presence of a base B1 selected from a hydroxide salt or tert-butoxide salt, a methoxide salt or a phenoxide salt, in a polar solvent such as dry or extra dry DMF.

In a particular embodiment, step a) comprises the addition of a compound of formula (II) with a compound of formula (III) as defined above, in the presence of a base B1 selected from a tert-butoxide salt of an alkaline metal ion such as Li+, in a polar solvent such as dry or extra dry DMF, under pressure and/or at a temperature above 50° C., preferably greater than 75° C., such as 85° C.±5° C. or 100° C.±5° C.

In a particular embodiment, step a) comprises the addition of a compound of formula (II) with a compound of formula (III) as defined above, in the presence of a base B1 selected from a tert-butoxide salt of an alkaline metal ion such as Li+, in a polar solvent such as dry or extra dry DMF, under microwaves, under pressure and/or at a temperature above 50° C., preferably greater than 75° C., such as 85° C.±5° C. or 100° C.±5° C.

Of note, the ynamide compound of formula (II) is easily prepared in three steps from the corresponding aniline of formula $Ar_3$—$NH_2$, namely (i) protection of the nitrogen of the aniline of formula $Ar_3$—$NH_2$ (preferably with a carbamate group such as Boc), (ii) coupling with a bromoalkyne of formula Br—≡—$R_6$ (obtained by bromination of the corresponding alkyne of formula ≡—$R_6$), followed by deprotection of the nitrogen protecting group (for instance under acidic conditions in the case of a Boc protecting group), using methods known in the art. If $R_6$ is H, then the corresponding tri($C_1$-$C_6$)alkylsilylalkyne is used (in particular triisopropylsilylacetylene TIPS-≡) to produce the brominated tri($C_1$-$C_6$)alkylsilylalkyne (Br—≡—Si($C_1$-$C_6$-alkyl)$_3$, and the corresponding triakylsilyl group is later deprotected, after the bromination step or the coupling step (for a review see Evano et al. Angew. Chem. Int. Ed. 2010, 49, 2840-2859). One can in particular refer to PCT application number EP2016/071115 (WO 2017/042233) for exemplary methods of preparation.

Also, the imine compound of formula (III) is easily prepared in one step, for example by condensing the corresponding aldehyde $Ar_1$CHO and amine $Ar_2$CHR$_4$NH$_2$ or by condensing the corresponding ketone $Ar_1R_{4a}$CHO and amine $Ar_2$CH$_2$NH$_2$ using methods known in the art. One can in particular refer to PCT application number EP2016/071115 (WO 2017/042233) for exemplary methods of preparation.

When the compound of formula (II) is reacted with an aldimine of formula (IIIa) with $R_4$=H, two molecules of compound (II) can react with one molecule of formula (IIIa) in order to form a compound of formula (Ib) with $R_{4a}$ being a group of formula —C(CH$_2$R$_6$)=NAr$_3$.

4. Conjugates

The present invention further relates to a conjugate of a compound of formula (I) or (I') with an antibiotics, typically an antibiotic containing a beta-lactam moiety, through a linker, i.e. the compound of formula (I) or (I') and the antibiotics are covalently linked together and form a single molecule.

Such conjugates are common in the art. One can in particular refer to the marketed compound sultamicillin, which is a conjugate of sulbactam (an enhancer) with ampicillin (an antibiotic). A synthesis of sultamicillin is in particular described by del Pozo et al. (Tetrahedron, 2001, 57, 6209-6214). Analogs were also described (U.S. Pat. No. 4,868,297).

The conjugate of the invention may thus be represented by the following formula (IV):

Inhibitor-Linker-Antibio (IV)

wherein Inhibitor is a compound of formula (I) or (I') as defined above, preferably linked to Linker via a phenoxy or a thiophenoxy group, Linker is a covalent linking group or a bond Antiobio is an antibiotic or a derivative thereof, preferably linked to Linker via an ester or amide bond.

Inhibitor

Inhibitor is a compound of formula (I) or (I'), preferably of formula (I), comprising a OH, SH, NH$_2$, ester (—COO— or OOC—), thioester (—C(O)S— or S(O)C—), amide (—CONH— or NHCO—), thioamide (—CSNH— or NHCS—), carbonate (—OC(O)O—) or carbamate (OC(O)NH or NHC(O)O) group, which is used to connect Inhibitor to Linker via an ether, thioether, amino, ester, thioester, amide, thioamide, carbonate or carbamate bond.

Advantageously, Inhibitor is a compound of formula (I), preferably comprising a phenol (C$_6$H$_4$OH), a thiophenol (C$_6$H$_4$SH), an aniline (C$_6$H$_4$NH$_2$), an ester, a thioester, an amide, a thioamide, a carbonate or a carbamate group.

In a particular embodiment, Inhibitor is a compound of formula (I), wherein at least one of $Ar_1$, $Ar_2$ and $Ar_3$ is substituted with one OH, NH$_2$, COOH or CONH$_2$ group, preferably with one OH group. For instance, $Ar_1$ is substituted with one OH group, or $Ar_2$ is substituted with one OH group, or $Ar_3$ is substituted with one OH group. More preferably, $Ar_1$ is a phenyl group substituted with one OH group, or $Ar_2$ is a phenyl group substituted with one OH group, or $Ar_3$ is a phenyl group substituted with one OH group.

Linker

In a particular embodiment, Linker represents any type of linker that may be degraded in vivo by an esterase.

In another embodiment, Linker represents any type of linker which will not interact with the Inhibitor, in particular with a compound of formula (I).

For instance, Linker is a $C_1$-$C_{10}$ alkylene, more preferably a $C_1$-$C_4$ alkylene, such as a methylene (—CH$_2$—). In some embodiment, Linker is linear, while in some other embodiments, Linker is branched.

Linker may also be a $A^1$-($C_1$-$C_{10}$)alkylene-$A^2$-, more $A^1$-($C_1$-$C_4$)alkylene-$A^2$-, such as a $A^1$-CH$_2$-$A^2$- group, wherein $A^1$ and $A^2$ are identical or different and independently are O, NH, S, S(O), S(O)$_2$, C(O)O, OC(O), C(O)NH, NHC(O), OC(O)O, OC(O)NH, NHC(O)O, and wherein a methylene unit (—CH$_2$—) (one or several, for instance 1, 2 or 3) may be replaced by an oxygen atom.

Antibio

Antibio is an antibiotic or a derivative thereof, preferably comprising a carboxylate group (—COO— or OOC—), a thiocarboxylate group (—C(O)S— or S(O)C—), an amide group (—CONH— or NHCO—), a thioamide group (—CSNH— or NHCS—), a carbonate group (—OC(O)O—) or a carbamate group (OC(O)NH or NHC(O)O), connects Antibio to Linker through a covalent ester, thioester, amide, thioamide, carbonate or carbamate bond, preferably through a covalent ester, amide, carbonate or carbamate bond.

Examples of known antibiotics which may be used in the compositions of the invention belong to at least one of the families consisting of the beta-lactam family (such as an amoxicillin and/or ampicillin and/or the cephalosporin family (such as cephazolin)), the tetracycline family (such as chlortetracycline), the rifamycin family (such as rifampicin), the peptide family (such as a polymyxin), the aminoside family (such as streptomycin), the phenicol family (such as chloramphenicol), the macrolide family (such as erythromycin).

Preferably, the combination comprises at least one known beta-lactam antibiotic. Examples of beta lactams preferentially used according to the present invention comprise carbapenems such as imipenem, meropenem, ertapenem and the compound commonly known as "PZ-601" (also known as Razupenem), or cephalosporins. Examples of cephalosporins are cefacetril, cefadroxil, cephalexin, cefaloglycin, cefalonium, cefaloridine, cefapirine; cefatrizine, cafazaflure, cefazedon, cefazolin, cefadrin, cefroxadin, ceftezol, cefaclor, cefamandole, cefuroxime, cefonicid, cofranid, cefprozil, loracrabef, cefotetan, cefoxitin, cefotiam hexetil, ceftriaxone, ceftizoxime, cefoperazone, cefsulodine, ceftibuten, cefixim, cefatamet, cefpodoxim proxetil, cefepime, cefpirome, ceftazidime, cefotaxime, cefalotin, etc. In yet another embodiment, the known antibiotic(s) is/are selected from the group consisting of the beta-lactams (for instance amoxicillin, ampicillin, carbapenems, and/orcephalosporins such as listed above), the glycopeptides, the polymyxins, the gramicidins, tyrocidin, the aminosides, the macrolides, the lincosamides, the synergistins, the phenicols, the tetracyclines, fusidic acid, the oxazolidinones, the rifamycins, the quinolones, the fluoroquinolones, the sulfamides, trimethoprim, and the mixtures thereof.

More preferably, the known antibiotic is selected from the group consisting of the penicillins, oxacillin, cloxacillin, ampicillin, meropenem, ertapenem, PZ-601, amoxicillin, bacampicillin, metampicillin, pivampicillin, azlocillin, mezlocillin, piperacillin, ticarcillin, pivmecillinam, sulbactam, tazobactam, imipenem, cephalexin, cephadroxil, cephaclor, cephatrizine, cephalotin, cephapirin, cephazolin, cephoxitin, cephamandole, cephotetan, cephuroxime, cephotaxime, cephsulodin, cefepime, cephoperazone, cephotiam, cephtazidime, cephtriaxone, cephixime, cephpodoxime, cephepime, colistin, latamoxef, aztreonam, vancomycin, vancocin, teicoplanin, polymyxin B, colistin, bacitracin, tyrothricin, streptomycin, kanamycin, tobramycin, amikacin, sisomycin, dibekacin, netilmycin, spectinomycin, spiramycin, ceftazidime, erythromycin, josamycin, roxithromycin, clarithromycin, azithromycin, lincomycin, clindamycin, virginiamycin, pristinamycin, dalfopristine-quinupristine, chloramphenicol, thiamphenicol, tetracycline, doxycycline, minocycline, fusidic acid, linezolide, rifamycin, rifampicin, nalidixic acid, oxolinic acid, pipemidic acid, flumequin, pefloxacin, norfloxacin, ofloxacin, ciprofloxacin, enoxacin, sparfloxacin, levofloxacin, moxifloxacin, nitroxolin, tilboquinol, nitrofurantoin, nifuroxazide, metronidazole, ornidazole, sulfadiazine, sulfamethisol, trimethoprim, isoniazide and the derivatives and mixtures thereof. Said antibiotics, and more particularly amoxicillin, can optionally be used in association with yet at least another beta-lactamase inhibitor such as clavulanic acid, another 3-imidazoline (compound of formula (I) or (I') of the invention), or an azetidinimine as defined in PCT application number EP2016/071115 (WO 2017/042233).

In a particular embodiment, Antibio is a cephalosporin (in particular as listed above) or ampicillin derivative.

Pro-Drug

In a first embodiment, Linker is degraded in vivo by esterases, thus releasing both the antibiotics (Antibio) and the potentiating agent (Inhibitor). In this first embodiment, the conjugate may thus be regarded as a pro-drug of both the antibiotics (Antibio) and the potentiating agent (Inhibitor).

This may enable increasing the solubility and penetration of both the antibiotics (Antibio) and the potentiating agent (Inhibitor), which might otherwise be different. This ensures that both the antibiotics (Antibio) and the potentiating agent (Inhibitor) are released at the same location (same part of the body), with the same biodistribution profile, thus enhancing their synergistic activity.

This therapeutic approach is for instance the one used in sultamicillin. Such an approach is in particular used when Antibio is linked to Linker via an ester bond, such as a —COO— group.

Therefore, in this embodiment, antibio is preferably a derivative of ampicillin or cephalosporin (in particular as listed above), preferably a cephalosporin.

Vectorization

In a second embodiment, Antibio actually acts as a vectorizing agent: it is used as a substrate for beta-lactamases and/or carbapenemases, which will degrade the "Antibio" part of the conjugate (comprising the beta-lactam moiety), and concomitantly release the potentiating agent (Inhibitor) directly at its desired site of action, i.e. next to the beta-lactamases and/or carbapenemases to be inhibited.

Such a therapeutic strategy has been described for other active substances, not necessarily in the field of antibiotics. Mention may be made of a cephalosporin-taxol conjugate (Lee et al. Current Biology, 1995, vol 2, n° 4, 223-227), a masked MK801 (Yang et al. e.Life 2015, 4, e10206), a cephem (cephalothine)-primaquine conjugate (Blau et al Molecules 2008, 13, 841-854).

In this second embodiment, Antibio is an antibiotic belonging to the beta-lactam family. Examples of antibiotics belonging to the beta-lactam family are listed above. More specifically, in this embodiment Antibio is a cephalosporin derivative.

Preferred Embodiments

In a preferred embodiment, Antibio is cephalosporin or a derivative thereof, ampicillin or a derivative thereof, linked to LINKER via an ester, amide, carbonate or carbamate bond, preferably via an ester or amide bond, more preferably via an ester bond.

Advantageously, in this embodiment, Inhibitor is a compound of formula (I), comprising a phenoxy ($C_6H_4OH$), an aniline ($C_6H_4NH_2$), an ester or an amide group. Preferably, in Inhibitor, at least one of $Ar_1$, $Ar_2$ and $Ar_3$ is substituted with one OH, $NH_2$, COOH or CON $H_2$ group, preferably with one OH group. For instance, $Ar_1$ is substituted with one OH group, or $Ar_2$ is substituted with one OH group, or $Ar_3$ is substituted with one OH group. More preferably, $Ar_1$ is a phenyl group substituted with one OH group, or $Ar_2$ is a phenyl group substituted with one OH group, or $Ar_3$ is a phenyl group substituted with one OH group.

Linker is preferably a $C_1$-$C_4$ alkylene, such as a methylene (—$CH_2$—), or $A^1$-($C_1$-$C_4$)alkylene-$A^2$-, such as a $A^1$-$CH_2$-$A^2$- group, wherein $A^1$ and $A^2$ are identical or different and independently are O, NH, S, S(O), $S(O)_2$, C(O)O, OC(O), C(O)NH, NHC(O), OC(O)O, OC(O)NH, NHC(O)O.

Exemplary formulae (V), (VI) and (VII) of the conjugate of the invention are shown below:

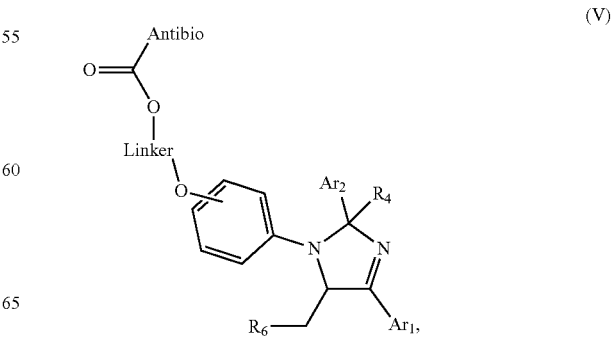

(V)

-continued

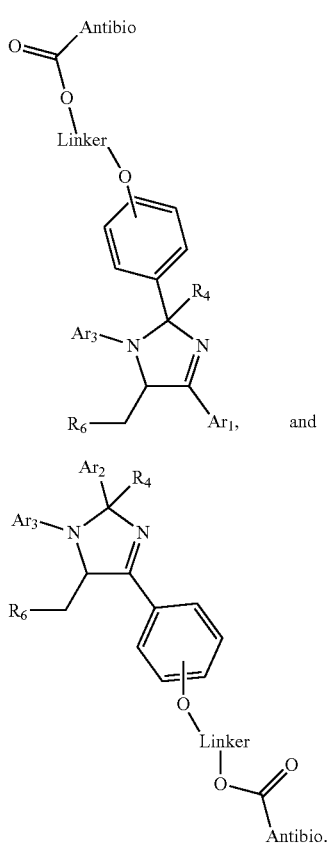

(VI)

(VII)

In formula (V), (VI) and (VII), Antibio is preferably a cephalosporin, in particular as listed above.

4. Pharmaceutical Compositions

The present invention also relates to a pharmaceutical composition comprising at least one compound of formula (I) or (I') or a conjugate thereof with an antibiotic (especially a conjugate of formula (IV)) as presently disclosed and mixtures thereof as active ingredient (in particular in the form of a mixture of enantiomers and/or diastereoisomers of formula (I) or (I') or (IV)), and a pharmaceutically acceptable carrier.

Preferably the composition comprises another therapeutically active substance, advantageously an antibiotic, for instance an antibiotic already known as such and already used as medicament specific in this field and whose activity is potentiated by the compounds of formula (I) and/or (I') or a conjugate thereof with an antibiotic (especially a conjugate of formula (IV)). The antibiotic may however be a compound of formula (I) or (I'), as they also exert antibiotic activity, or a conjugate thereof with an antibiotic (especially a conjugate of formula (IV)).

In a particular embodiment of the present invention, the pharmaceutical composition comprises one compound of formula (I) or (I') as presently disclosed, or a conjugate thereof with an antibiotic (especially a conjugate of formula (IV)), and an antibiotic or a combination of antibiotics as active ingredients, and a pharmaceutically acceptable carrier.

Preferably, the pharmaceutical composition of the present invention comprises at least two therapeutically active substances, one of which exerts a potentiating action on the other(s).

Examples of known antibiotics which may be used in the compositions of the invention belong to at least one of the families consisting of the beta-lactam family (such as an amoxicillin and/or ampicillin and/or a cephalosporin such as cephazolin), the tetracycline family (such as chlortetracycline), the rifamycin family (such as rifampicin), the peptide family (such as a polymyxin), the aminoside family (such as streptomycin), the phenicol family (such as chloramphenicol), the macrolide family (such as erythromycin).

Preferably, the combination comprises at least one known beta-lactam antibiotic. Examples of beta lactams preferentially used according to the present invention comprise carbapenems such as imipenem, meropenem, ertapenem and the compound commonly known as "PZ-601", or cephalosporins, in particular cephalosporins are cefacetril, cefadroxil, cephalexin, cefaloglycin, cefalonium, cefaloridine, cefapirine; cefatrizine, cafazaflure, cefazedon, cefazolin, cefadrin, cefroxadin, ceftezol, cefaclor, cefamandole, cefuroxime, cefonicid, cofranid, cefprozil, loracrabef, cefotetan, cefoxitin, cefotiam hexetil, ceftriaxone, ceftizoxime, cefoperazone, cefsulodine, ceftibuten, cefixim, cefatamet, cefpodoxim proxetil, cefepime, cefpirome, ceftazidime, cefotaxime, cefalotin, etc.

In yet another embodiment, the known antibiotic(s) is/are selected from the group consisting of the beta-lactams (such as an amoxicillin, an ampicillin, carbapenems, and cephalosporins), the glycopeptides, the polymyxins, the gramicidins, tyrocidin, the aminosides, the macrolides, the lincosamides, the synergistins, the phenicols, the tetracyclines, fusidic acid, the oxazolidinones, the rifamycins, the quinolones, the fluoroquinolones, the sulfamides, trimethoprim, and the mixtures thereof.

More preferably, the known antibiotic is selected from the group consisting of the penicillins, oxacillin, cloxacillin, ampicillin, meropenem, ertapenem, PZ-601, amoxicillin, bacampicillin, metampicillin, pivampicillin, azlocillin, mezlocillin, piperacillin, ticarcillin, pivmecillinam, sulbactam, tazobactam, imipenem, cephalexin, cephadroxil, cephaclor, cephatrizine, cephalotin, cephapirin, cephazolin, cephoxitin, cephamandole, cephotetan, cephuroxime, cephotaxime, cephsulodin, cefepime, cephoperazone, cephotiam, cephtazidime, cephtriaxone, cephixime, cephpodoxime, cephepime, colistin, latamoxef, aztreonam, vancomycin, vancocin, teicoplanin, polymyxin B, colistin, bacitracin, tyrothricin, streptomycin, kanamycin, tobramycin, amikacin, sisomycin, dibekacin, netilmycin, spectinomycin, spiramycin, ceftazidime, erythromycin, josamycin, roxithromycin, clarithromycin, azithromycin, lincomycin, clindamycin, virginiamycin, pristinamycin, dalfopristine-quinupristine, chloramphenicol, thiamphenicol, tetracycline, doxycycline, minocycline, fusidic acid, linezolide, rifamycin, rifampicin, nalidixic acid, oxolinic acid, pipemidic acid, flumequin, pefloxacin, norfloxacin, ofloxacin, ciprofloxacin, enoxacin, sparfloxacin, levofloxacin, moxifloxacin, nitroxolin, tilboquinol, nitrofurantoin, nifuroxazide, metronidazole, ornidazole, sulfadiazine, sulfamethisol, trimethoprim, isoniazide and the derivatives and mixtures thereof. Said antibiotics, and more particularly amoxicillin, can optionally be used in association with yet at least another beta-lactamase inhibitor such as clavulanic acid, another 3-imidazoline (compound of formula (I) or (I') of the invention, or an azetidinimine as defined in PCT application number EP2016/071115 (WO 2017/042233).

Of course, the pharmaceutical composition according to the invention is not restricted to the use of only those antibiotics mentioned above. In fact, considering the potentiating effect exerted by the compound defined in the compounds of formula (I), (I') or (IV), other known or future antibiotics can also be successfully used.

These pharmaceutical compositions may be administered orally, rectally, parenterally, intramuscularly or locally by topical application on the skin and the mucosa. Preferably, the pharmaceutical composition is administered orally or parenterally (in particular intravenously).

In all cases, the pharmaceutical form of the pharmaceutical composition of the invention shall be adapted to its use. For example, it can be used in the form of a solution, suspension, tablet . . . for oral administration. The compositions for parenteral administration are generally pharmaceutically acceptable sterile solutions or suspensions which can optionally be prepared immediately before use. The aqueous solutions may be suitable for intravenous administration in so far as the pH is properly adjusted and they are made isotonic, for example by adding a sufficient amount of sodium chloride or glucose.

The compositions according to the present invention can be solid or liquid and present in pharmaceutical forms in current use in human medicine or veterinary use such as, for example, simple or coated tablets, capsules, granules, suppositories, injectable preparations, ointments, creams, gels; they are prepared according to the usual methods. The active principle or principles can be incorporated in the excipients usually used in these pharmaceutical compositions, such as cellulose derivatives (HPMC, HPC, microcrystalline cellulose, etc.), talc, gum Arabic, lactose, starch, magnesium stearate, cocoa butter, aqueous or other media, fatty bodies of animal or plant origin, paraffin derivatives, glycols, different wetting, dispersing or emulsifying agents, preservatives. These compositions can notably take the form of a lyophilisate designed to be dissolved as required in an appropriate solvent, for example pyrogen free sterile water.

The compound(s) and/or pharmaceutical composition(s) according to the invention can be formulated so as to be suitable for a simultaneous or sequential administration of said at least one compound of formula (I) or (I') according to the invention and known antibiotic agent(s) as defined above.

The pharmaceutical composition of the invention thus enables the treatment of local or systemic infections caused by resistant microorganisms using doses of the compound of formula (I) or (I') the present invention, or combinations thereof optionally with a known antibiotics agent(s) as defined above.

In the case of such a combination, the dose of the combined active substance is preferably lower than the simple addition of the doses required for treating the same infections due to susceptible microorganisms with one or the other of these same said compound of formula (I) according to the invention and known antibiotic agent as defined above alone.

The result is to offer a treatment which has at least the following advantages:
 effectiveness at very low doses against nonresistant microorganisms,
 effectiveness against microorganisms resistant to at least one therapeutic agent,
 control of recurrence phenomena, and/or
 control of phenomena of resistant microorganisms selection.

Advantageously, there is a notable reduction in the risks of toxicity and/or adverse effects (well known to the person of the art for the known antibiotics), thanks to the potentiation which enables the administration of very low doses.

Therefore, the present invention in particular concerns a kit comprising:
 at least one first container containing a first therapeutically active compound of formula (I) or (I') as defined above, and
 at least one second container containing a second therapeutically active substance which is an antibiotic, as a combination product for simultaneous, sequential and separate use, in particular in antibiotherapy.

The kit of the invention preferably contains instructions for use. Said kit enables health care personnel to prepare on demand either a mixture of suitable doses of the desired first therapeutic substance(s) and of the desired antibiotic(s), for a simultaneous administration, or to sequentially and separately administer the suitable dose of at least one said first therapeutically active substance, followed by the suitable dose of at least one said second therapeutically active substance, that is, the suitable antibiotic, or vice versa. However, a mixture for simultaneous use shall be preferred for ease of administration.

The present invention thus also relates to a method for treating or preventing a bacteria infection, comprising administering to a patient in need thereof a therapeutically effective dose of the compositions of the invention comprising a compound of formula (I) or (I'), in combination with an effective dose of antibiotics, or the kit of the invention.

The compositions and kits of the invention are thus useful as drugs, especially in antibiotherapies. The compositions of the invention are in particular useful as antibiotics.

5. Therapeutic Applications

The compounds, conjugates, pharmaceutical compositions and kits of the invention are a simple and efficient means to fight the problems related to microbial agents in general which comprise mainly resistance to therapeutic agents and toxicity of the latter resulting from the use of high doses.

The compounds of formula (I) and (I') and conjugates thereof are useful as an inhibitor of a carbapenemase enzyme, in particular a carbapenemase of class A, B and/or D, preferably of a NDM-1 type, OXA-48 type or a KPC-type enzymes. As such, they are useful as as a potentiating agent, preferably of an antibiotic.

Indeed, the combination of at least one compound of formula (I) (and/or (I')) with at least one antibiotic advantageously provides a potentiating effect, i.e. by "potentiating effect/action" it is meant according to the present invention that at least one of the active compounds acts either as a "suicide molecule" as explained above enabling the other active ingredient to be active (i.e. antibiotic), and/or increases the activity of at least one of the other compounds present in term of biological (i.e. antibiotic) activity through e.g. a synergistic effect.

The compounds of formula (I) and (I') are thus also useful as drugs, in particular in antibiotherapies. The compounds of formula (I) and (I') are thus in particular used in combination with an antibiotic, such as described below in connection with the compositions or kits of the invention. In such case, the antibiotic and/or the combination is preferably effective on bacteria chosen from gram-negative bacteria such as Enterobacteriaceae, *Pseudomonas aeruginosa, Acinetobacter baumannii*, preferably drug resistant forms of gram-negative bacteria to one or several classes of antibiotics comprising beta-lactams by production of a beta-lactamase.

The compounds of formula (I) and (I') and compositions comprising same may also be used as antibiotics. In this case, it is preferably effective on bacteria chosen from gram-negative bacteria such as Enterobacteriaceae, *Pseudomonas aeruginosa, Acinetobacter baumannii*, preferably drug resistant forms of gram-negative bacteria to one or several classes of antibiotics comprising beta-lactams by production of a beta-lactamase.

Therefore, said compounds of formula (I) according to the present invention can be used alone, or in combination with each other, or at least one other antibiotic already known. The derivatives thereof, if they have antibiotic activity, can also be used.

In a particular embodiment, the compounds of formula (I) or (I') are used as a drug (antibiotic), in the form of a mixture of enantiomers and/or diastereoisomers.

The present invention further concerns a compound of formula (I) or (I'), for the manufacture of a medicament, in particular a potentiating agent for antibiotics or an antibiotic.

The present invention also relates to a method for treating or preventing a bacteria infection, comprising administering to a patient in need thereof a therapeutically effective dose of a compound of formula (I) or (I'), optionally in combination with an effective dose of antibiotics.

The therapeutically effective dose of the compound(s) of formula (I) or (I') may vary depending on the severity and nature of the condition being treated, the particular subject, the administration route and the other antibacterial product involved. It can be, for example, between 0.1 mg and 1 g per kg per day, by oral route in humans or for veterinary purposes, or between 0.05 mg and 0.5 g per kg per day by intramuscular or intravenous route in humans or for veterinary purposes. The dose of the known antibacterial compound can also vary depending on the condition being treated, the particular subject, the administration route and the product involved, but generally follows the typical doses prescribed by practitioners, for example for human administration as described in the French reference Vidal. This dose can range up to 10 g per day per patient, or even more. Nevertheless, as a result of the potentiation provided by the compounds of general formula (I) to the known antibacterial compound(s), doses of the latter as part of the combination can be reduced compared to standard doses. The inventive combinations can also be used as disinfectants for surgical instruments.

EXAMPLES

The invention shall become clearer in the following examples describing different embodiments, which are given only for purposes of illustration, and should not be constructed as limiting the present invention in any way.

Example 1: Synthesis

1. Material and Methods

Melting points were measured in capillary tubes on a Büchi B-540 apparatus and are uncorrected. Infrared spectra were recorded on a Perkin Elmer Spectrum BX FT-IR spectrometer. Proton (1H) and carbon (13C) NMR spectra were recorded on Bruker spectrometers: Avance 300 MHz (QNP-13C, 31P, 19F-probe or Dual 13C probe) and Avance 500 MHz (BB0-ATM probe or BBI-ATM probe). Carbon NMR (13C) spectra were recorded at 125 or 75 MHz, using a broadband decoupled mode with the multiplicities obtained using a JMOD or DEPT sequence. NMR experiments were carried out in deuterochloroform (CDCl3), chemical shifts (δ) are reported in parts per million (ppm) with reference to CDCl3 (1H: 7.26; 13C: 77.00). The following abbreviations are used for the proton spectra multiplicities: s: singlet, bs: broad singlet, d: doublet, t: triplet, q: quartet, m: multiplet, br: broad. Coupling constants (J) are reported in Hertz (Hz). Mass spectra were obtained either with a LCT (Micromass) instrument using electrospray ionization (ES), or from a Time of Flight analyzer (ESI-MS) for the high-resolution mass spectra (HRMS). Elemental analyses were performed on a Perkin Elmer CHN 2400 analyzer with detection by catharometry. Thin-layer chromatography was performed on silica gel 60 F254 on aluminium plates (Merck) and visualized under a UVP Mineralight UVLS-28 lamp (254 nm) and with ninhydrin and phosphomolybdic acid in ethanol. Flash chromatography was conducted on Merck silica gel 60 (40-63 μm) at medium pressure (300 mbar) or on CombiFlash apparatus (Serlabo Technologies), using standard settings. Chiral High Pressure Liquid Chromatography (HPLC) was performed on a Waters 2695 Separations Module equipped with a diode array UV detector (254 nm) and with a Daicel CHIRACEL IA column (4.6*250 nm, 5 mm). Data are reported as follows: column temperature, eluent, flow rate, retention time. Microwaves irradiation experiments were carried out in an Anton Paar Monowave 300 or Monowave 50 instrument with internal optic-fiber- or IR temperature control.

All reagents were obtained from commercial suppliers unless otherwise stated. Where necessary, organic solvents were routinely dried and/or distilled prior to use and stored over molecular sieves under nitrogen. Commercial DMF (anhydrous DMF) was purchased from Sigma-Aldrich in Sure/Seal™ Bottles or from Acros in AcroSeal™ Bottles. Organic extracts were dried over magnesium sulfate (MgSO$_4$).

2. General Procedures

General Procedure A: Imine Formation

Where the imine is not commercially available, it may be synthesized using the following protocol. Aldehyde (1.0 equiv.), aniline (1.0 equiv.) and silica (1.0 equiv.) are successively added in a round bottom flask followed by the addition of ethanol (0.7M). The mixture is then placed in an ultrasound unit for 5-10 minutes (monitored by TLC) and filtered to remove silica. After concentration under reduced pressure, the crude imine is recrystallized in absolute ethanol.

General Procedure: 3-imidazoline Formation

Imine (0.2 mmol, 1.0 equiv.), ynamide (0.4 mmol, 2.0 equiv.), SiO$_2$ (20 mg, 0.2 mmol, 1.0 equiv.) are successively added in a microwave sealed tube and placed under argon before the addition of t-BuOLi 2.2 M in solution in THF (182 μL, 0.4 mmol, 2.0 équiv.) followed by extra dry DMF (0.3 M). The sealed tube is placed in a microwave apparatus for 1 h at 100° C. The crude material is purified by flash chromatography on silica gel using a mixture of ethyl acetate in petroleum ether as eluent.

The following imidazolines were obtained using the General procedure above (the yield is indicated as a percentage in brackets).

Compound 1
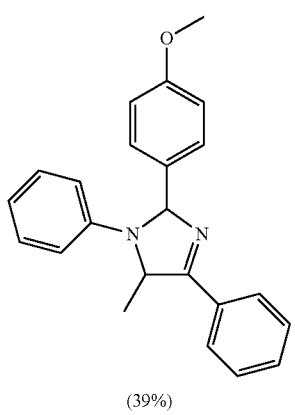
(39%)
Compound 2
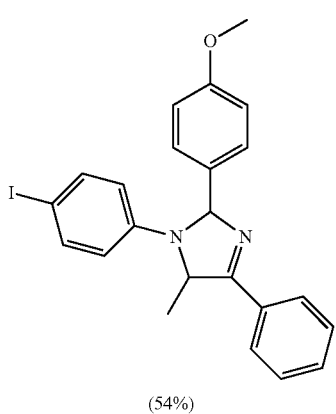
(54%)
Compound 3
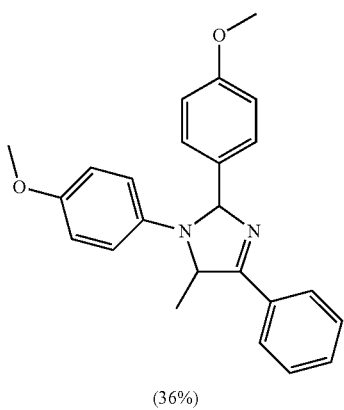
(36%)
Compound 4
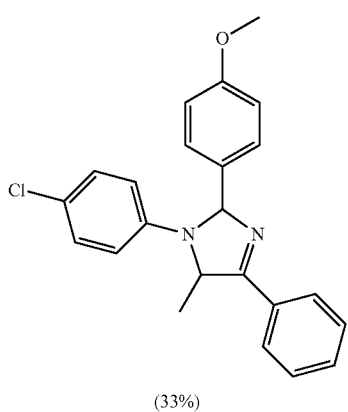
(33%)
Compound 5
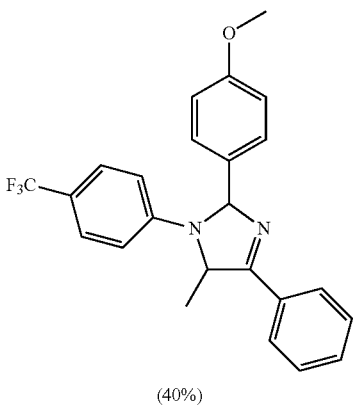
(40%)
Compound 6
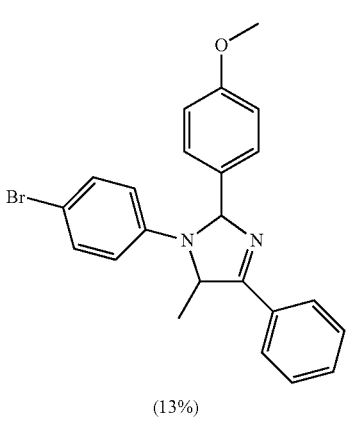
(13%)
Compound 7
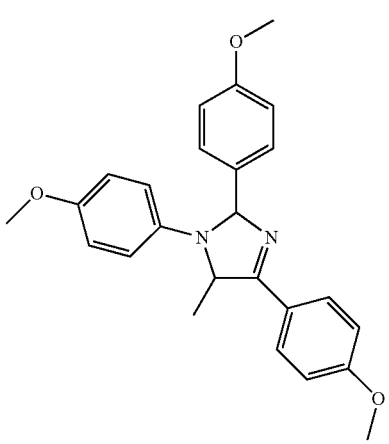
(19%)
Compound 8
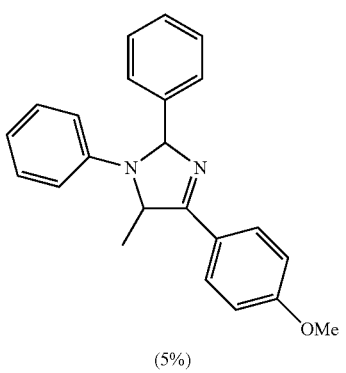
(5%)

-continued
Compound 9
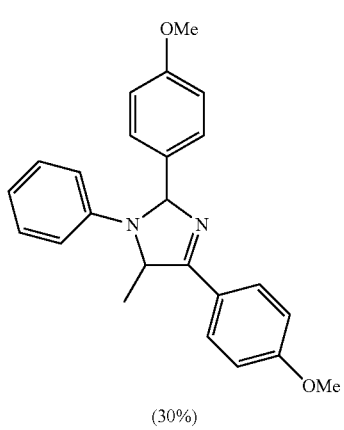
(30%)
Compound 10
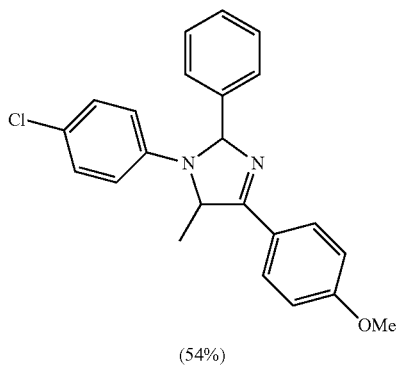
(54%)
Compound 11
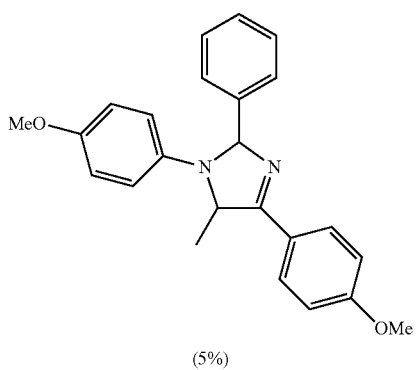
(5%)
Compound 12
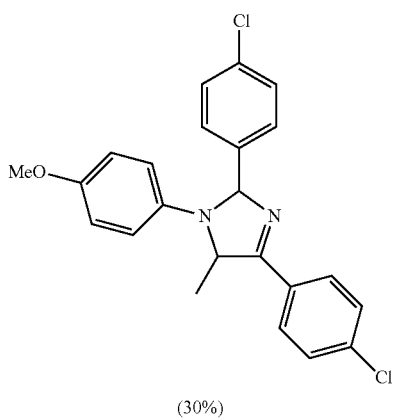
(30%)
-continued
Compound 13
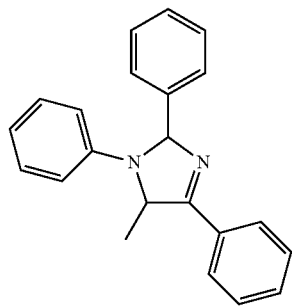
(24%)
Compound 14
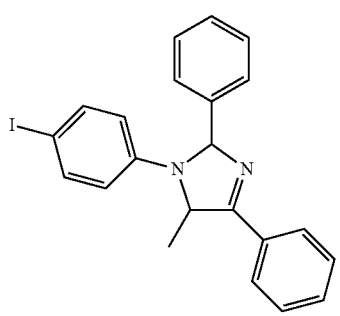
(20%)
Compound 15
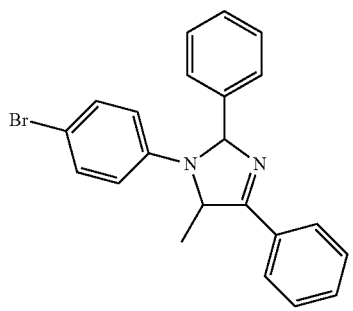
(52%)
Compound 16
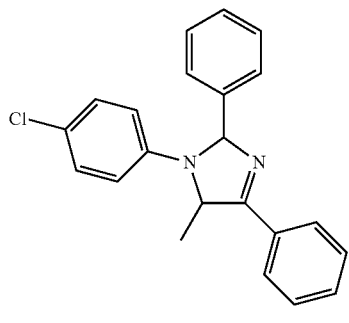
(54%)

Compound 17
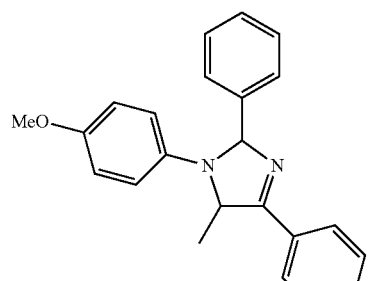
(57%)
Compound 18
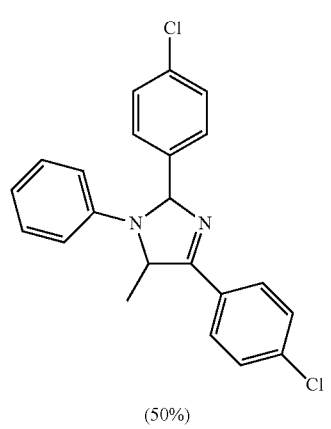
(50%)
Compound 19
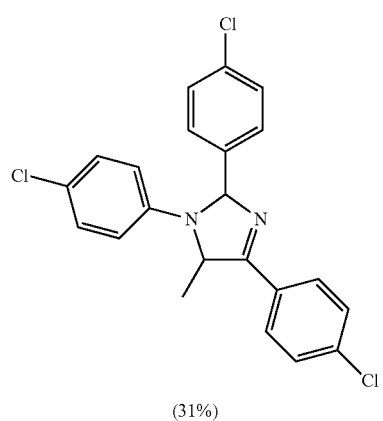
(31%)
Compound 20
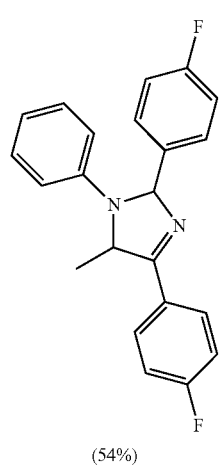
(54%)
Compound 21
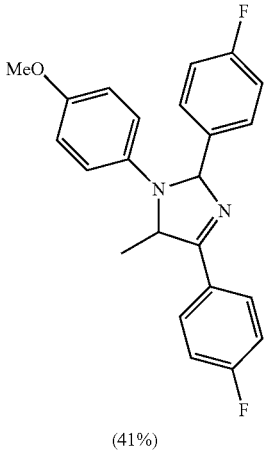
(41%)
Compound 22
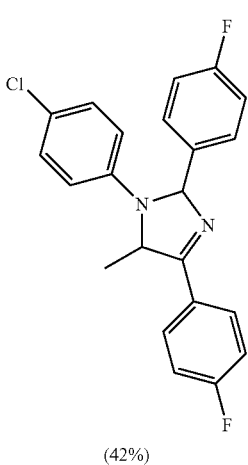
(42%)
Compound 23
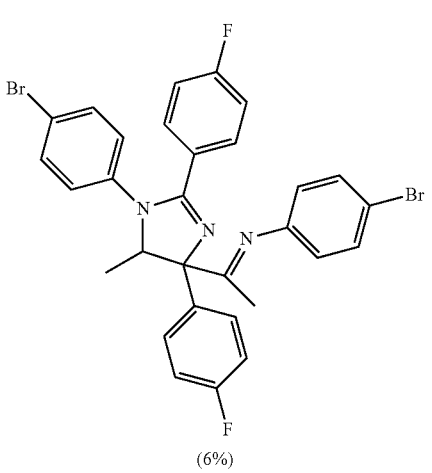
(6%)

Compound 24
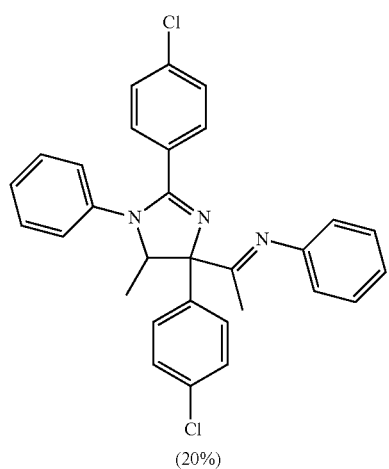
(20%)
Compound 25
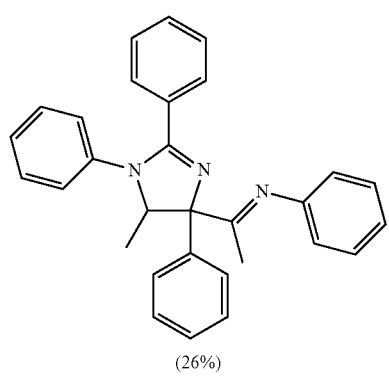
(26%)
Compound 26
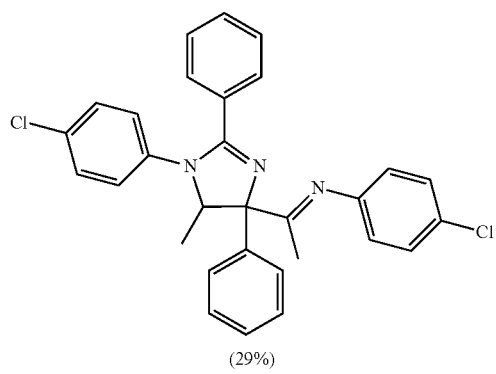
(29%)
Compound 27
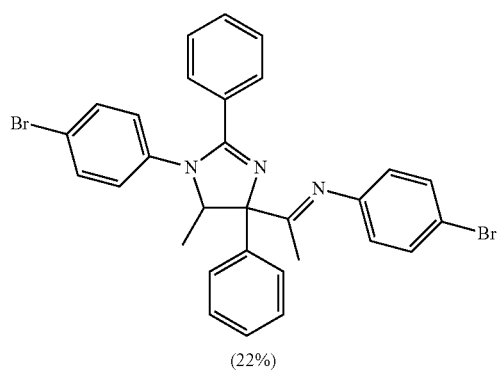
(22%)
Compound 28
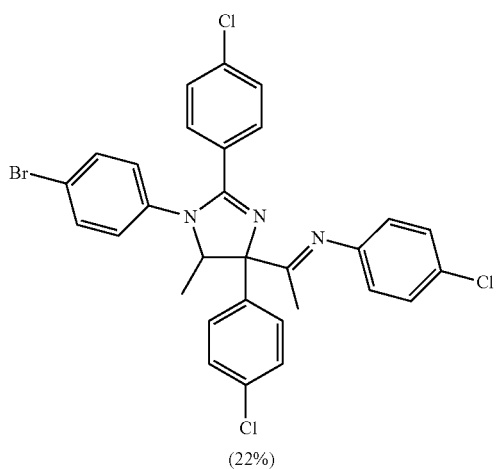
(22%)
Compound 29
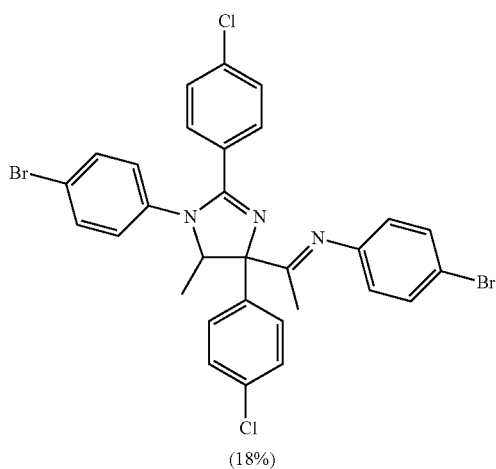
(18%)
Compound 30
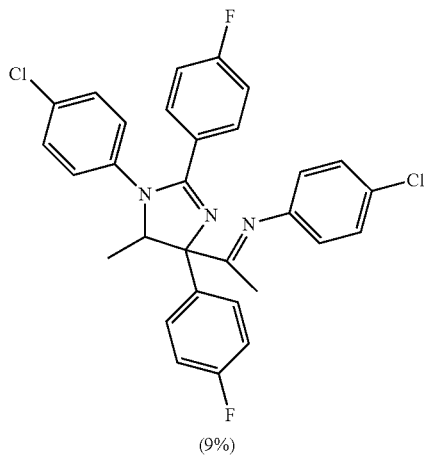
(9%)

Compound 31

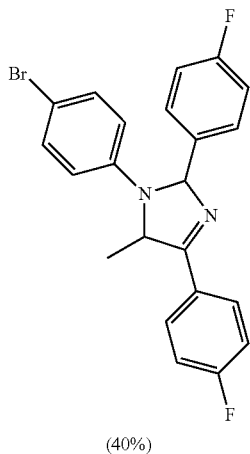

(40%)

3. Analytical Data for 3-Imidazolines According to the Present Invention

Compound 1 (39%)

$^1$H NMR (300 MHz, CDCl$_3$): δ 7.88-7.82 (m, 2H), 7.57-7.45 (m, 4H), 7.31-7.28 (m, 2H), 6.98 (d, J=8.5 Hz, 2H), 6.81 (t, J=7.0 Hz, 1H), 6.67 (d, J=8.3 Hz, 2H), 6.51 (d, J=2.0 Hz, 1H), 5.31 (qd, J=6.6, 2.0 Hz, 1H), 3.86 (s, 3H), 1.69 (d, J=6.6 Hz, 3H). $^{13}$C NMR (75 MHz, CDCl$_3$): δ 170.9 (C), 159.4 (C), 145.2 (C), 132.8 (C), 131.9 (C), 129.5 (2CH), 128.6 (2CH), 128.2 (2CH), 127.9 (CH), 117.5 (CH), 114.2 (2CH), 112.2 (2CH), 91.8 (CH), 62.4 (CH), 55.3 (CH$_3$), 20.0 (CH$_3$). HRMS: [M+H]$^+$ m/z 343.1810, found 343.1818. IR (film): 3060, 2975, 2933, 2836, 1598, 1501, 1338, 1246, 1170, 1029, 908, 834, 747, 730, 693 cm$^{-1}$.

Compound 2 (54%)

$^1$H NMR (300 MHz, CDCl$_3$): δ 7.88-7.82 (m, 2H), 7.51-7.40 (m, 7H), 6.95 (d, J=8.7 Hz, 2H), 6.43-6.39 (m, 3H), 5.31 (qd, J=6.4, 2.1 Hz, 1H), 3.87 (s, 3H), 1.64 (d, J=6.4 Hz, 3H). $^{13}$C NMR (75 MHz, CDCl$_3$): δ 170.7 (C), 159.5 (C), 144.5 (C), 138.8 (C), 138.0 (2CH), 132.2 (C), 131.6 (C), 128.7 (2CH), 128.2 (2CH), 127.9 (2CH), 126.7 (CH), 114.5 (2CH), 114.0 (2CH), 91.6 (CH), 62.2 (CH), 55.4 (CH$_3$), 19.7 (CH$_3$). HRMS: [M+H]$^+$ m/z 469.0776, found 469.0781. IR (film): 3060, 3033, 2973, 2836, 1607, 1585, 1509, 1489, 1340, 1243, 1171, 1029, 836, 806, 731, 695 cm$^{-1}$.

Compound 3 (36%)

$^1$H NMR (300 MHz, CDCl$_3$): δ 7.85-7.81 (m, 2H), 7.52 (d, J=8.7 Hz, 2H), 7.49-7.40 (m, 3H), 6.96 (d, J=8.7 Hz, 2H), 6.87 (d, J=9.0 Hz, 2H), 6.59 (d, J=9.0 Hz, 2H), 6.40 (d, J=2.5 Hz, 1H), 5.23 (qd, J=6.5, 2.5 Hz, 1H), 3.84 (s, 3H), 3.76 (s, 3H), 1.65 (d, J=6.5 Hz, 3H). $^{13}$C NMR (75 MHz, CDCl$_3$): δ 171.0 (C), 159.4 (C), 152.0 (C), 139.9 (C), 133.3 (C), 132.0 (C), 130.9 (CH), 128.6 (2CH), 128.2 (2CH), 128.0 (2CH), 115.2 (2CH), 114.2 (2CH), 112.9 (2CH), 92.3 (CH), 62.8 (CH), 55.8 (CH$_3$), 55.4 (CH$_3$), 20.3 (CH$_3$). HRMS: [M+H]$^+$ m/z 373.1916, found 373.1923. IR (film): 3058, 2934, 2864, 2834, 1609, 1510, 1247, 1169, 1033, 836, 814, 697 cm$^{-1}$.

Compound 4 (33%)

$^1$H NMR (300 MHz, CDCl$_3$): δ 7.85-7.77 (m, 2H), 7.52-7.39 (m, 5H), 7.18 (d, J=8.8 Hz, 2H), 6.96 (d, J=8.5 Hz, 2H), 6.55 (d, J=8.8 Hz, 2H), 6.43 (bs, 1H), 5.25-5.21 (m, 1H), 3.84 (s, 3H), 1.64 (d, J=6.4 Hz, 3H). $^{13}$C NMR (75 MHz, CDCl$_3$): δ 170.7 (C), 159.5 (C), 143.7 (C), 132.3 (C), 131.7 (C), 131.1 (CH), 129.3 (2CH), 128.7 (2CH), 128.2 (2CH), 127.9 (CH), 122.5 (C), 114.3 (2CH), 113.2 (2CH), 91.8 (CH), 62.4 (CH), 55.4 (CH$_3$), 19.8 (CH$_3$). HRMS: [M+H]$^+$ m/z 377.1420, found 377.1423. IR (film): 3061, 2974, 2933, 2837, 1600, 1509, 1495, 1341, 1248, 1171, 1030, 837, 810, 731, 696 cm$^{-1}$.

Compound 5 (40%)

$^1$H NMR (300 MHz, CDCl$_3$): δ 7.87-7.79 (m, 2H), 7.53-7.39 (m, 5H), 7.04-6.84 (m, 5H), 6.74-6.66 (m, 1H), 6.52-6.44 (m, 1H), 5.31-5.23 (m, 1H), 3.84 (s, 3H), 1.68 (d, J=6.4 Hz, 3H). $^{13}$C NMR (75 MHz, CDCl$_3$): δ 170.0 (C), 159.6 (C), 145.2 (2C), 132.0 (C), 131.6 (C), 131.2 (CH), 129.9 (2CH), 128.7 (2CH), 128.2 (2CH), 127.9 (2CH), 115.5 (2CH), 114.3 (2CH), 91.7 (CH), 62.3 (CH), 55.4 (CH$_3$), 19.7 (CH$_3$). HRMS: [M+H]$^+$ m/z 411.1684, found 411.1689.

Compound 6 (13%)

$^1$H NMR (300 MHz, C$_6$D$_6$): δ 7.67 (d, J=9.0 Hz, 2H), 7.39 (d, J=8.5 Hz, 2H), 7.27-7.17 (m, 2H), 7.00 (d, J=8.8 Hz, 1H), 6.56 (d, J=9.0 Hz, 2H), 6.45 (d, J=8.8 Hz, 2H), 4.81 (d, J=7.3 Hz, 1H), 5.31 (dq, J=7.3, 6.2 Hz, 1H), 3.12 (s, 3H), 1.12 (d, J=6.2 Hz, 3H). $^{13}$C NMR (75 MHz, C$_6$D$_6$): δ 160.4 (C), 155.6 (C), 144.1 (C), 142.4 (C), 132.2 (2CH), 131.8 (CH), 131.0 (2CH), 128.7 (2CH), 127.0 (2CH) 126.7 (2CH), 123.5 (C), 117.5 (C), 113.7 (2CH), 71.7 (CH), 70.1 (CH), 54.5 (CH$_3$), 20.8 (CH$_3$). HRMS: $^{79}$Br[M+H]$^+$ m/z 421.0955, found 421.0960.

Compound 7 (19%)

$^1$H NMR (300 MHz, C$_6$D$_6$): δ 7.72 (d, J=8.9 Hz, 2H), 7.61 (d, J=8.6 Hz, 2H), 6.86 (d, J=8.0 Hz, 4H), 6.72 (d, J=8.9 Hz, 2H), 6.58 (d, J=9.1 Hz, 2H), 6.51 (d, J=2.3 Hz, 1H), 4.84 (qd, J=6.4, 2.4 Hz, 1H), 3.42 (s, 3H), 3.30 (s, 3H), 3.20 (s, 3H), 1.43 (d, J=6.5 Hz, 3H). $^{13}$C NMR (75 MHz, C$_6$D$_6$): δ169.9 (C), 161.8 (C); 159.8 (C), 152.6 (C), 140.3 (C), 134.2 (C), 130.1 (2CH), 128.4 (2CH), 125.3 (C), 115.4 (2CH), 114.3 (2CH), 114.0 (2CH), 113.3 (2CH), 92.5 (CH), 62.8 (CH), 55.3 (CH$_3$), 54.7 (CH$_3$), 54.65 (CH$_3$), 20.4 (CH$_3$). HRMS: [M+H]$^+$ m/z 403.2015, found 403.2017. IR (film): 2956, 1607, 1507, 1236, 1167, 1029 cm$^{-1}$ Compound 8 (5%)

$^1$H NMR (300 MHz, C$_6$D$_6$): δ 7.72-7.68 (m, 2H), 7.54 (d, J=8.7 Hz, 2H), 7.23-7.18 (m, 2H), 7.10-7.07 (m, 3H), 6.83-6.81 (m, 3H), 6.60 (d, J=8.1 Hz, 2H), 6.52 (d, J=2.1 Hz, 1H), 4.81 (qd, J=6.4, 2.1 Hz, 1H), 3.28 (s, 3H), 1.32 (d, J=6.4 Hz, 3H). HRMS: [M+H]$^+$ m/z 343.1810, found 343.1807.

Compound 9 (30%)

$^1$H NMR (300 MHz, C$_6$D$_6$): δ7.71 (d, J=8.9 Hz, 2H), 7.56 (d, J=8.6 Hz, 2H), 7.21 (dd, J=8.6, 7.4 Hz, 2H), 6.84-6.80 (m, 3H), 6.71 (d, J=8.9 Hz, 2H), 6.63 (d, J=7.9 Hz, 2H), 6.54

(d, J=1.9 Hz, 1H), 4.84 (qd, J=6.5, 1.9 Hz, 1H), 3.29 (s, 3H), 3.21 (s, 3H), 1.40 (d, J=6.5 Hz, 3H). $^{13}$C NMR (75 MHz, C$_6$D$_6$): δ169.5 (C), 161.9 (C), 159.8 (C), 145.7 (C), 133.7 (C), 130.1 (2CH), 129.6 (2CH), 128.3 (2CH), 125.1 (C), 117.5 (CH), 114.3 (2CH), 113.9 (2CH), 112.6 (2CH), 91.8 (CH), 62.2 (CH), 54.7 (2CH$_3$), 19.9 (CH$_3$). HRMS: [M+H]$^+$ m/z 373.1910, found 373.1913. IR (film): 2959, 1599, 1355, 1244, 1168, 1028 cm$^{-1}$ Compound 10 (54%)

$^1$H NMR (300 MHz, C$_6$D$_6$): δ7.70-7.66 (m, 2H), 7.38 (d, J=7.1 Hz, 2H), 7.23 (t, J=7.4 Hz, 2H), 7.13-7.10 (m, 1H), 6.98-7.95 (m, 3H), 6.81 (d, J=8.8 Hz, 2H), 6.46 (d, J=8.8 Hz, 2H), 4.82 (d, J=7.6 Hz, 1H), 3.57 (quint, J=6.6 Hz, 1H), 1.11 (d, J=6.3 Hz, 3H). $^{13}$C NMR (75 MHz, C$_6$D$_6$): δ162.2 (C), 144.1 (C), 142.2 (C), 131.6 (C), 130.2 (C), 130.0 (CH), 129.3 (2CH), 129.2 (2CH), 128.7 (2CH), 128.2 (2CH), 127.4 (CH), 127.0 (2CH), 126.4 (2CH), 76.9 (CH), 70.2 (CH), 20.7 (CH$_3$). HRMS: [M+H]$^+$ m/z 347.1309, found 347.0945. IR (film): 3061, 1489, 1371, 1090, 752, 696 cm$^{-1}$ Compound 11 (5%)

$^1$H NMR (300 MHz, C$_6$D$_6$): δ 7.73-7.70 (m, 2H), 7.58 (d, J=8.1 Hz, 2H), 7.09-7.05 (m, 3H), 6.88-6.84 (m, 3H), 6.58-6.47 (m, 3H), 6.50 (bs, 1H), 4.86-4.76 (m, 1H), 3.42 (s, 3H), 3.30 (s, 3H), 1.36 (d, J=6.4 Hz, 3H). HRMS: [M+H]$^+$ m/z 373.1916, found 373.1922.

Compound 12 (30%)

$^1$H NMR (300 MHz, C$_6$D$_6$): δ7.60 (d, J=8.5 Hz, 2H), 7.27-7.24 (m, 2H), 7.20-7.14 (m, 2H), 6.93 (d, J=8.5 Hz, 2H), 6.67 (d, J=8.8 Hz, 2H), 6.53 (d, J=8.8 Hz, 2H), 4.70 (d, J=9.1 Hz, 1H), 3.43 (qd, J=9.0, 6.2 Hz, 1H), 3.18 (s, 3H), 1.14 (d, J=6.2 Hz, 3H). $^{13}$C NMR (75 MHz, C$_6$D$_6$): δ162.7 (C), 158.0 (C), 142.9 (C), 136.3 (C), 135.9 (C); 133.1 (C), 130.8 (2CH), 130.3 (C), 128.8 (2CH), 128.5 (2CH), 128.3 (2CH), 127.9 (2CH), 114.7 (2CH), 76.0 (CH), 71.5 (CH), 54.7 (CH$_3$), 20.1 (CH$_3$). HRMS: [M+H]$^+$ m/z 411.1025, found 411.1000. IR (film): 3041, 1608, 1508, 1243, 1089, 1013, 738 cm$^{-1}$ Compound 13 (24%)

$^1$H NMR (300 MHz, C$_6$D$_6$): δ7.81-7.77 (m, 1H), 7.43 (d, J=7.7 Hz, 2H), 7.23 (t, J=7.4 Hz, 2H), 7.13-7.08 (m, 1H), 6.97-6.95 (m, 3H), 6.90-6.85 (m, 3H), 6.79-6.77 (m, 3H), 4.87 (d, J=7.8 Hz, 1H), 3.69 (quint, J=6.6 Hz, 1H), 1.20 (d, J=6.2 Hz, 3H). $^{13}$C NMR (75 MHz, C$_6$D$_6$): δ 162.7 (C), 144.4 (C), 143.9 (C), 132.0 (C), 129.8 (CH), 129.5 (2CH), 129.1 (2CH), 128.7 (2CH), 128.0 (CH), 127.3 (CH), 127.1 (2CH), 125.6 (2CH), 124.9 (CH), 77.0 (CH), 70.5 (CH), 20.8 (CH$_3$). HRMS: [M+H]$^+$ m/z 313.1698, found 313.1714. IR (film): 3060, 1592, 1491, 695 cm$^{-1}$ Compound 14 (20%)

$^1$H NMR (300 MHz, C$_6$D$_6$): δ 7.70 (d, J=7.6 Hz, 2H), 7.38 (d, J=7.5 Hz, 2H), 7.23 (t, J=7.4 Hz, 2H), 7.14-7.10 (m, 3H), 6.99-6.95 (m, 3H), 6.29 (d, J=8.4 Hz, 2H), 4.82 (d, J=7.3 Hz, 1H), 3.60 (quint, J=6.5 Hz, 1H), 1.11 (d, J=6.2 Hz, 3H). $^{13}$C NMR (75 MHz, C$_6$D$_6$): δ 161.8 (C), 144.1 (C), 143.3 (C), 138.1 (C), 131.7 (C), 130.0 (CH), 129.3 (2CH), 128.7 (2CH), 128.2 (2CH), 127.4 (CH), 126.9 (2CH), 126.7 (2CH), 88.5 (CH), 77.0 (C), 69.9 (CH), 20.8 (CH$_3$). HRMS: [M+H]$^+$ m/z 439.0665, found 439.0183. IR (film): 2970, 1712, 1485, 1369, 1218, 1005, 696 cm$^{-1}$ Compound 15 (52%)

$^1$H NMR (300 MHz, C$_6$D$_6$): δ 7.69 (dd, J=7.7, 1.8 Hz, 2H), 7.38 (d, J=7.1 Hz, 2H), 7.23 (d, J=7.4 Hz, 2H), 7.15-7.13 (m, 2H), 7.00-6.94 (m, 4H), 6.40 (d, J=8.8 Hz, 2H), 4.82 (d, J=7.5 Hz, 2H), 3.62-3.54 (dq, J=7.5, 6.2 Hz, 1H), 1.11 (d, J=6.2 Hz, 3H). $^{13}$C NMR (75 MHz, C$_6$D$_6$): δ 161.9 (C), 144.1 (C), 142.7 (C), 132.2 (2CH), 131.7 (C), 130.0 (CH), 129.4 (2CH), 128.7 (2CH), 127.4 (CH), 126.9 (2CH), 126.6 (2CH), 117.9 (C), 77.0 (CH), 70.0 (CH), 20.7 (CH$_3$). HRMS: [M+H]$^+$ m/z 391.0804, found 391.0754. IR (film): 3060, 1487, 1370, 695 cm$^{-1}$ Compound 16 (54%)

$^1$H NMR (300 MHz, C$_6$D$_6$): δ 7.70-7.66 (m, 2H), 7.38 (d, J=7.1 Hz, 2H), 7.23 (t, J=7.4 Hz, 2H), 7.13-7.10 (m, 1H), 6.98-7.95 (m, 3H), 6.81 (d, J=8.8 Hz, 2H), 6.46 (d, J=8.8 Hz, 2H), 4.82 (d, J=7.6 Hz, 1H), 3.57 (quint, J=6.6 Hz, 1H), 1.11 (d, J=6.3 Hz, 3H). $^{13}$C NMR (75 MHz, C$_6$D$_6$): δ 162.2 (C), 144.1 (C), 142.2 (C), 131.6 (C), 130.2 (C), 130.0 (CH), 129.3 (2CH), 129.2 (2CH), 128.7 (2CH), 128.2 (2CH), 127.4 (CH), 127.0 (2CH), 126.4 (2CH), 76.9 (CH), 70.2 (CH), 20.7 (CH$_3$). HRMS: [M+H]$^+$ m/z 347.1309, found 347.0945.IR (film): 3061, 1489, 1371, 1090, 752, 696 cm$^{-1}$ Compound 17 (57%)

$^1$H NMR (300 MHz, C$_6$D$_6$): δ 7.88-7.85 (m, 2H), 7.52 (d, J=7.7 Hz, 2H), 7.28 (t, J=7.4 Hz, 2H), 7.19-7.18 (m, 1H), 7.00-6.98 (m, 3H), 6.76 (d, J=8.3 Hz, 2H), 6.50 (d, J=8.3 Hz, 2H), 4.90 (d, J=8.8 Hz, 1H), 3.63 (quint, J=6.8 Hz, 1H), 3.14 (s, 3H), 1.23 (d, J=6.2 Hz, 3H). $^{13}$C NMR (75 MHz, C$_6$D$_6$): δ 163.5 (C), 157.7 (C), 144.7 (C), 136.9 (C), 132.1 (C), 129.7 (CH), 129.5 (2CH), 128.7 (2CH), 128.0 (2CH), 127.9 (2CH), 127.2 (CH), 127.1 (2CH), 114.6 (2CH), 76.8 (CH), 71.5 (CH), 54.6 (CH$_3$), 20.3 (CH$_3$). HRMS: [M+H]$^+$ m/z 343.1804, found 343.1817. IR (film): 3060, 1507, 1242, 1029, 696 cm$^{-1}$ Compound 18 (50%)

$^1$H NMR (300 MHz, C$_6$D$_6$): δ 7.50 (d, J=8.3 Hz, 2H), 7.22-7.19 (m, 2H), 7.13-7.10 (m, 3H), 6.89-6.82 (m, 4H), 6.69 (d, J=7.5 Hz, 2H), 4.67 (d, J=8.1 Hz, 1H), 3.49 (quint, J=6.6 Hz, 1H), 1.12 (d, J=6.2 Hz, 3H). $^{13}$C NMR (75 MHz, C$_6$D$_6$): δ162.0 (C), 143.4 (C); 142.6 (C), 136.1 (C), 133.2 (C), 130.7 (2CH), 130.1 (C) 129.3 (2CH), 128.8 (2CH), 128.41 (2CH), 128.36 (2CH), 125.7 (2CH), 125.4 (CH), 76.1 (CH), 70.5 (CH), 20.6 (CH$_3$). HRMS: [M+H]$^+$ m/z 381.0919, found 381.0917. IR (film): 3060, 1589, 1488, 1089, 1013, 696 cm$^{-1}$ Compound 19 (31%)

$^1$H NMR (300 MHz, C$_6$D$_6$): δ 7.39 (d, J=8.6 Hz, 2H), 7.21 (d, J=8.5 Hz, 2H), 7.07 (d, J=8.4 Hz, 2H), 6.90 (d, J=8.6 Hz, 2H), 6.83 (d, J=8.7 Hz, 2H), 6.35 (d, J=8.7 Hz, 2H), 4.62 (d, J=8.0 Hz, 1H), 3.38 (qd, J=6.30, 6.27 Hz, 1H), 1.01 (d, J=6.2 Hz, 3H). $^{13}$C NMR (75 MHz, C$_6$D$_6$): δ 161.4 (C), 142.3 (C), 141.6 (C), 136.3 (C), 133.3 (C); 130.9 (C), 130.6 (2CH), 129.7 (C), 129.4 (2CH), 128.9 (2CH), 128.5 (2CH), 128.2 (2CH), 126.6 (2CH), 76.0 (CH), 70.2 (CH), 20.4 (CH$_3$).

HRMS: [M+H]⁺ m/z 415.0529, found 415.0539. IR (film): 2967, 1488, 1089, 1013, 732 cm$^{-1}$ Compound 20 (54%)

$^1$H NMR (300 MHz, C$_6$D$_6$): δ 7.58 (q, J=4.8 Hz, 2H), 7.18 (q, J=4.6 Hz, 2H), 6.93-6.86 (m, 4H), 6.82-6.77 (m, 1H), 6.73-6.70 (m, 2H), 6.57 (t, J=8.8 Hz, 2H), 4.71 (d, J=8.0 Hz, 1H), 3.53 (qd, J=8.0, 6.3 Hz, 1H), 1.14 (d, J=6.3 Hz, 3H). $^{13}$C NMR (75 MHz, C$_6$D$_6$): δ 163.8 (d, J=249.8 Hz, C), 162.5 (d, J=244.7 Hz, C), 161.7 (C), 143.6 (C), 140.0 (C), 131.5 (d, J=8.8 Hz, 2CH), 129.2 (2CH), 128.5 (d, J=8.0 Hz, 2CH), 125.7 (2CH), 125.3 (CH), 115.4 (d, J=21.2 Hz, 2CH), 115.1 (d, J=21.7 Hz, 2CH), 76.1 (CH), 70.7 (CH), 20.6 (CH$_3$). HRMS: [M+H]⁺ m/z 349.1510, found 349.1513. IR (film): 3062, 1602, 1507, 1222, 1152 cm$^{-1}$ Compound 21 (41%)

$^1$H NMR (300 MHz, C$_6$D$_6$): δ 7.64 (dd, J=8.9, 5.5 Hz, 2H), 7.26 (dd, J=8.4, 5.5 Hz, 2H), 6.94 (t, J=8.7 Hz, 2H), 6.70-6.52 (m, 6H), 4.74 (d, J=9.0 Hz, 1H), 3.48 (qd, J=9.0, 6.2 Hz, 1H), 3.18 (s, 3H), 1.16 (d, J=6.2 Hz, 3H). $^{13}$C NMR (75 MHz, C$_6$D$_6$): δ163.7 (d, J=250.1 Hz, C), 162.5 (d, J=244.8 Hz, C), 162.5 (C), 158.0 (C), 140.3 (C); 136.5 (C), 131.5 (d, J=8.7 Hz, 2CH), 128.6 (d, J=7.8 Hz, 2CH), 128.0 (2CH), 115.4 (d, J=21.2 Hz, 2CH), 115.0 (d, J=21.5 Hz, 2CH), 114.7 (2CH), 76.0 (CH), 71.6 (CH), 54.7 (CH$_3$), 20.1 (CH$_3$). HRMS: [M+H]⁺ m/z 379.1616, found 379.1621. IR (film): 2966, 1607, 1505, 1220, 1155, 1034 cm$^{-1}$ Compound 22 (42%)

$^1$H NMR (300 MHz, C$_6$D$_6$): δ 7.48 (dd, J=8.9, 5.5 Hz, 2H), 7.17-7.12 (m, 2H), 6.93-6.83 (m, 4H), 6.58 (t, J=8.7 Hz, 2H), 6.40 (d, J=8.8 Hz, 2H), 4.67 (d, J=7.9 Hz, 1H), 3.42 (qd, J=7.8, 6.3 Hz, 1H), 1.05 (d, J=6.2 Hz, 3H). $^{13}$C NMR (75 MHz, C$_6$D$_6$): δ 163.9 (d, J=250.2 Hz, C), 162.5 (d, J=244.9 Hz, C), 161.2 (C), 141.9 (C), 139.7 (C), 131.4 (d, J=8.7 Hz, 2CH), 130.7 (C), 129.4 (2CH), 128.5 (d, J=7.9 Hz, 2CH), 126.6 (2CH), 126.5 (C), 115.5 (d, J=21.6 Hz, 2CH), 115.2 (d, J=22.3 Hz, 2CH), 76.1 (CH), 70.3 (CH), 20.4 (CH$_3$). HRMS: calculated for $^{35}$Cl [M+H]⁺ m/z 383.1120, found 383.1130. IR (film): 2970, 1604, 1506, 1220, 1155, 1091, 741 cm$^{-1}$ Compound 23 (6%)

$^1$H NMR (300 MHz, C$_6$D$_6$): δ 7.49 (t, J=6.3 Hz, 4H), 7.22 (d, J=7.4 Hz, 2H), 7.03 (d, J=7.5 Hz, 2H), 6.94 (t, J=7.5 Hz, 2H), 6.63 (t, J=8.0 Hz, 2H), 6.39 (d, J=7.6 Hz, 2H), 6.26 (d, J=7.4 Hz, 2H), 5.40 (q, J=6.5 Hz, 1H), 1.13 (s, 3H), 0.75 (d, J=6.6 Hz, 3H). $^{13}$C NMR (75 MHz, C$_6$D$_6$): δ172.2 (C), 164.2 (d, J=248.6 Hz, C), 162.7 (d, J=249.7 Hz, C), 160.8 (C), 150.0 (C), 141.8 (C), 135.6 (C), 132.2 (d, J=8.5 Hz, 2CH), 131.6 (d, J=8.7 Hz, 2CH), 129.5 (d, J=7.7 Hz, 2CH), 126.0 (4CH), 125.9 (C), 121.0 (4CH), 117.9 (C), 116.5 (C), 115.4 (d, J=21.5 Hz, 2CH), 83.5 (C), 64.8 (CH), 17.7 (CH$_3$), 16.8 (CH$_3$). HRMS: calcd for $^{79}$Br*2 [M+H]⁺ m/z 622.0299, found 622.0314. IR (film): 2971, 1657, 1505, 1221, 1155, 1069, 736 cm$^{-1}$ Compound 24 (20%)

$^1$H NMR (300 MHz, C$_6$D$_6$): δ7.54-7.49 (m, 4H), 7.24 (d, J=8.7 Hz, 2H), 7.11-7.09 (m, 1H), 6.96-6.87 (m, 6H), 6.80-6.74 (m, 3H), 6.67 (dd, J=8.5, 1.2 Hz, 2H), 5.71 (q, J=6.8 Hz, 1H), 1.95 (s, 3H), 0.95 (d, J=6.8 Hz, 3H). $^{13}$C NMR (75 MHz, C$_6$D$_6$): δ171.3 (C), 161.3 (C), 151.3 (C), 142.8 (C), 138.9 (C), 136.4 (C), 133.5 (C), 130.9 (2CH), 130.1 (C), 129.4 (2CH), 129.2 (2CH), 129.1 (2CH), 128.6 (2CH), 128.4 (2CH), 125.0 (2CH), 124.9 (CH), 123.4 (CH), 119.3 (2CH), 83.6 (C), 65.1 (CH), 17.8 (CH$_3$), 16.8 (CH$_3$). HRMS: [M+H]⁺ m/z 498.1798, found 498.1512. IR (film): 3062, 1658, 1591, 1486, 1090, 826, 695 cm$^{-1}$ Compound 25 (26%)

$^1$H NMR (300 MHz, C$_6$D$_6$): δ 7.83-7.78 (m, 4H), 7.31-7.24 (m, 2H), 7.12-7.08 (m, 3H), 7.02-6.97 (m, 4H), 6.90-6.84 (m, 5H), 6.64 (dd, J=8.4, 1.2 Hz, 2H), 5.58 (q, J=6.7 Hz, 1H), 1.84 (s, 3H), 0.83 (d, J=6.8 Hz, 3H). $^{13}$C NMR (75 MHz, C$_6$D$_6$): δ171.8 (C), 162.1 (C), 151.7 (C), 143.3 (C), 140.6 (C), 132.1 (C), 130.1 (CH), 129.7 (2CH), 128.9 (2CH), 128.4 (2CH), 128.3 (2CH), 128.1 (2CH), 128.0 (2CH), 127.4 (CH), 124.9 (2CH), 124.4 (CH), 123.2 (CH), 121.2 (C), 119.4 (2CH), 84.1 (C), 65.1 (CH), 17.9 (CH$_3$), 17.0 (CH$_3$). HRMS: [M+H]⁺ m/z 430,2278, found 430, 2267. IR (film): 3060, 3029, 2974,2927, 1711, 1658, 1592, 1491, 1362, 754, 694 cm$^{-1}$ Compound 26 (29%)

$^1$H NMR (300 MHz, C$_6$D$_6$): δ 7.76-7.68 (m, 4H), 7.29 (t, J=7.6 Hz, 2H), 7.19-7.16 (m, 1H), 7.07-7.00 (m, 5H), 6.83 (d, J=8.5 Hz, 2H), 6.52 (d, J=8.6 Hz, 2H), 6.35 (d, J=8.4 Hz, 2H), 5.52 (q, J=6.7 Hz, 1H), 1.83 (s, 3H), 0.85 (d, J=6.7 Hz, 3H). $^{13}$C NMR (75 MHz, C$_6$D$_6$): δ172.6 (C), 161.8 (C); 149.8 (C), 141.6 (C), 140.1 (C), 131.5 (C), 130.4 (CH), 129.8 (C); 129.5 (2CH), 129.2 (2CH), 129.1 (2CH), 128.7 (C); 128.5 (2CH), 128.2 (2CH), 127.9 (2CH), 127.6 (2CH), 125.8 (2CH), 120.7 (CH), 84.1 (C), 64.9 (CH), 17.7 (CH$_3$), 17.1 (CH$_3$). HRMS: [M+H]⁺ m/z 498.1498, found 498.1016. IR (film): 3060, 1658, 1484, 1361, 1213, 1090, 762, 700 cm$^{-1}$ Compound 27 (22%)

$^1$H NMR (300 MHz, C$_6$D$_6$): δ7.71-7.68 (m, 4H), 7.28 (t, J=7.8 Hz, 2H), 7.21-7.17 (m, 4H), 7.01-6.97 (m, 4H), 6.45 (d, J=8.7 Hz, 2H), 6.29 (d, J=8.6 Hz, 2H), 5.50 (q, J=6.7 Hz, 1H), 1.81 (s, 3H), 0.84 (d, J=6.7 Hz, 3H). $^{13}$C NMR (75 MHz, C$_6$D$_6$): δ172.5 (C), 161.7 (C), 150.3 (C), 142.0 (C), 140.0 (C), 132.2 (2CH), 132.0 (2CH), 131.5 (C), 130.4 (CH), 129.5 (2CH), 128.5 (2CH), 128.3 (2CH), 127.9 (2CH), 127.6 (2CH), 126.0 (2CH), 121.1 (CH), 117.5 (C), 116.3 (C), 84.1 (C), 64.8 (CH), 17.7 (CH$_3$), 17.0 (CH$_3$). HRMS: calculated for 2*$^{79}$Br [M+H]⁺ m/z 586.0487, found 586.0449. IR (film): 3060, 1712, 1487, 1217, 1069, 761, 700 cm$^{-1}$ Compound 28 (22%)

$^1$H NMR (300 MHz, C$_6$D$_6$): δ 7.42 (t, J=7.8 Hz, 4H), 7.26 (d, J=7.9 Hz, 2H), 7.08 (d, J=7.7 Hz, 2H), 6.97 (d, J=7.6 Hz, 2H), 6.86 (d, J=7.8 Hz, 2H), 6.42 (d, J=7.8 Hz, 2H), 6.32 (d, J=7.7 Hz, 2H), 5.38 (q, J=6.6 Hz, 1H), 1.71 (s, 3H), 0.72 (d, J=6.7 Hz, 3H). $^{13}$C NMR (75 MHz, C$_6$D$_6$): δ 172.0 (C), 160.9 (C), 149.4 (C), 141.1 (C); 138.4 (C); 136.8 (C); 133.8 (C), 130.8 (2CH), 130.4 (C); 129.5 (C), 129.31 (2CH), 129.27 (2CH), 129.2 (2CH), 129.0 (C), 128.7 (2CH), 128.6 (2CH), 125.8 (2CH), 120.6 (2CH), 83.6 (C), 64.8 (CH), 17.6

(CH₃), 16.8 (CH₃). HRMS: [M+H]⁺ m/z 565.0718, found 566.0703. IR (film): 2975, 1484, 1216, 1089, 1013, 733 cm⁻¹

Compound 29 (18%)

¹H NMR (300 MHz, C₆D₆): δ7.42-7.39 (m, 4H), 7.26 (d, J=8.8 Hz, 2H), 7.22 (d, J=8.6 Hz, 2H), 7.01 (d, J=8.7 Hz, 2H), 6.97 (d, J=8.7 Hz, 2H), 6.36 (d, J=8.7 Hz, 2H), 6.25 (d, J=8.6 Hz, 2H), 5.38 (q, J=6.7 Hz, 1H), 1.71 (s, 3H), 0.72 (d, J=6.8 Hz, 3H). ¹³C NMR (75 MHz, C₆D₆): δ 171.9 (C), 160.7 (C), 149.9 (C); 141.5 (C), 138.3 (C), 136.8 (C); 133.8 (C), 132.3 (2CH), 132.2 (2CH), 130.8 (2CH), 129.5 (C), 129.3 (2CH), 128.8 (2CH), 128.6 (2CH), 126.0 (2CH), 121.0 (2CH), 118.1 (C); 116.6 (C), 83.6 (C), 64.8 (CH), 17.6 (CH₃), 16.8 (CH₃). HRMS: calcd for ⁷⁹Br*2 et ³⁵Cl*2 [M+H]⁺ m/z 653.9308, found 653.9109. IR (film): 3063, 1712, 1481, 1217, 1013, 825, 731 cm⁻¹

Compound 30 (9%)

¹H NMR (300 MHz, C₆D₆): δ 7.51-7.47 (m, 4H), 7.08 (d, J=8.4 Hz, 2H), 6.97-6.86 (m, 4H), 6.63 (t, J=8.5 Hz, 2H), 6.45 (d, J=8.6 Hz, 2H), 6.33 (d, J=8.4 Hz, 2H), 5.41 (q, J=6.7 Hz, 1H), 1.75 (s, 3H), 0.76 (d, J=6.7 Hz, 3H). ¹³C NMR (75 MHz, C₆D₆): δ 172.3 (C), 164.2 (d, J=250.9 Hz, C), 164.2 (d, J=246.3 Hz, C), 160.8 (C), 157.5 (C), 149.5 (C), 141.3 (C), 135.6 (C), 131.6 (d, J=8.6 Hz, 2CH), 130.2 (C), 129.5 (d, J=7.8 Hz, 2CH), 129.2 (d, J=9.2 Hz, 2CH), 128.9 (C), 125.8 (4CH), 120.6 (4CH), 115.3 (d, J=21.5 Hz, 2CH), 83.5 (C), 64.9 (CH), 17.7 (CH₃), 16.8 (CH₃). HRMS: calculated for 2*³⁵Cl [M+H]⁺ m/z 534.1309, found 534.1346. IR (film): 2970, 1604, 1505, 1219, 1155, 1012, 734 cm⁻¹

Compound 31 (40%)

¹H NMR (300 MHz, C₆D₆): δ 7.47 (dd, J=8.9, 5.4 Hz, 2H), 7.16-7.11 (m, 2H), 7.00 (d, J=8.8 Hz, 2H), 6.90 (t, J=8.7 Hz, 2H), 5.57 (t, J=8.7 Hz, 2H), 6.33 (d, J=8.8 Hz, 2H), 4.67 (d, J=7.8 Hz, 1H), 3.42 (qd, J=7.6, 6.3 Hz, 1H), 1.04 (d, J=6.3 Hz, 3H)¹³C NMR (75 MHz, C₆D₆): δ 163.9 (d, J=250.2 Hz, C), 162.5 (d, J=245.0 Hz, C), 161.1 (C), 142.3 (C), 139.7 (C), 132.3 (2CH), 131.4 (d, J=8.8 Hz, 2CH), 128.4 (d, J=7.9 Hz, 2CH), 126.8 (2CH), 118.4 (C), 115.5 (d, J=21.3 Hz, 2CH), 115.2 (d, J=21.7 Hz, 2CH), 76.1 (CH), 70.1 (CH), 20.5 (CH₃). HRMS: [M+H]⁺ m/z 427.0615, found 427.0608. IR (film): 2968, 1604, 1506, 1220, 1155, 1010, 734 cm⁻¹

Example 2: Biological Tests

These tests are conducted by comparing UV absorbance slope measurements of impenem alone, and then imipenem with the concerned 3-imidazolines at given concentrations in the presence of the enzyme. It was thus possible to monitor the hydrolysis of imipenem. Lower the value of the slope, the higher is the percentage of inhibition of the enzyme.

The different biology test results made on the compounds of the present invention are summarized in the table 6.

TABLE 1

Biology test results summary

| Structures | NDM-1 Enzyme IC₅₀ (mM) | KPC Enzyme IC₅₀ (mM) | OXA-48 Enzyme Inhibition at 10 μM * |
|---|---|---|---|
| Compound 1 | 3.7 | 4.9 | 9% |
| Compound 2 | 1.0 | 3.5 | 9% |
| Compound 3 | 4.3 | 11.4 | 11% |
| Compound 4 | 1.4 | 3.9 | Not Detectable |
| Compound 5 | 2.4 | 6.6 | 19% |
| Compound 6 | 20%* | ND* | Not Detectable |
| Compound 7 | 5.8 | 18%* | Not Detectable |
| Compound 8 | 6.9 | 23%* | Not Detectable |
| Compound 9 | 3.8 | 40%* | Not Detectable |
| Compound 10 | 1.7 | 8.0 | 19% |
| Compound 11 | 20%* | ND* | Not Detectable |
| Compound 12 | 2.6 | 50% | Not Detectable |
| Compound 13 | 7.2 | 23%* | Not Detectable |
| Compound 14 | 3.0 | ND* | Not Detectable |
| Compound 15 | 7.0 | -ND* | Not Detectable |
| Compound 16 | 5.8 | 18%* | Not Detectable |
| Compound 17 | 6.5 | 17%* | Not Detectable |
| Compound 18 | 3.9 | 14%* | Not Detectable |
| Compound 19 | 2.5 | 6.0 | 50% |
| Compound 24 | 1.7 | 6.2 | 38% |
| Compound 25 | 4.4 | 30%* | Not Detectable |
| Compound 26 | 0.9 | 3.9 | 22% |
| Compound 27 | 1.0 | 3.6 | 38% |
| Compound 28 | 0.4 | 3.7 | 31% |
| Compound 29 | 0.6 | 4.4 | 36% |

*percentage of inhibition at 10 μM; ND: Not Detectable (at 10 μM).

The invention claimed is:
1. A compound of formula (I):

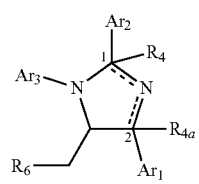

(I)

wherein
=== represents a single or double bond, with the proviso that one of the two bonds
=== is a single bond and the other is a double bond;
Ar₁ and Ar₂ are identical or different and are independently a mono or polycyclic C₅-C₁₂ aryl or mono or polycyclic C₃-C₁₂ heteroaryl group, optionally substituted with:
one to three substituents independently selected from the group consisting of: a halogen atom, OH, C₁-C₆ alkyl, C₃-C₇ cycloalkyl, C₁-C₆ alkoxy, C₃-C₇ cycloalkoxy, nitro, cyano, formyl, amino-C₁-C₁₀ alkoxy, (carboxylic acid)-C₁-C₁₀ alkoxy, (carboxylic (C₁-C₆)alkyl ester)-C₁-C₁₀ alkoxy, (1,2 diol)-C₂-C₁₀ alkoxy, —O—(C₁-C₆)alkyl-O—(C₁-C₆)alkyl-OH, (C₁-C₆)-alkoxy-(C₁-C₆)-alkyl, C₂-C₆ alkylcarbonyl, C₁-C₆ alkylthio, C₁-C₆ thioalkyl, (C₁-C₆)-alkylthio-(C₁-C₆)-alkyl, C₁-C₆ alkylsulfinyl, C₁-C₆ alkylsulfonyl, C₁-C₆ haloalkyl, C₁-C₆ haloalkoxy, C₁-C₆ haloalkoxy alkyl, C₂-C₆ haloalkylcarbonyl, C₁-C₆ haloalkylthio, C₁-C₆ haloalkylsulfinyl, C₁-C₆ haloalkylsulfonyl, C₂-C₆ alkenyl, C₂-C₆ alkynyl, C₂-C₆ haloalkynyl, C₂-C₆ haloalkenyl, C₂-C₆ haloalkenyloxy, C₂-C₆ haloalkynyloxy, C₂-C₆ alkenyloxy, C₂-C₆ alkynyloxy, C₂-C₆ alkenylthio, C₂-C₆ alkynylthio, $C_2$-$C_6$ haloalkenylthio, $C_2$-$C_6$ haloalkynylthio, and a $C_1$-$C_6$ alkoxy optionally substituted by a mono or polycyclic $C_5$-$C_{12}$ aryl group, a mono or polycyclic $C_5$-$C_{12}$ aryl or mono or polycyclic $C_3$-$C_{12}$ heteroaryl group optionally substituted with a halogen atom, OH, $C_1$-$C_6$ alkyl, or $C_1$-$C_6$ alkoxy; and/or a bridging group of formula —O—$CH_2$—O— or —O—$CH_2CH_2$—O—;

$Ar_3$ is a mono or polycyclic $C_5$-$C_{12}$ aryl group or mono or polycyclic $C_3$-$C_{12}$ heteroaryl group, optionally substituted with substituents independently selected from the group consisting of:

halogen atoms, OH, $C_1$-$C_6$ alkyl, $C_3$-$C_7$ cycloalkyl, $C_1$-$C_6$ alkoxy, $C_3$-$C_7$ cycloalkoxy, cyano, formyl, nitro, $C_1$-$C_6$ alkyl, $C_3$-$C_7$ cycloalkyl, $C_1$-$C_6$ alkoxy, ($C_1$-$C_6$)-alkoxy-($C_1$-$C_6$)-alkyl, $C_2$-$C_6$ alkylcarbonyl, $C_1$-$C_6$ alkylthio, $C_1$-$C_6$ thioalkyl, ($C_1$-$C_6$)-alkylthio-($C_1$-$C_6$)-alkyl, $C_1$-$C_6$alkylsulfinyl, $C_1$-$C_6$ alkylsulfonyl, $C_1$-$C_6$ haloalkyl, $C_1$-$C_6$ haloalkoxy, $C_1$-$C_6$ haloalkoxy alkyl, $C_2$-$C_6$ haloalkylcarbonyl, $C_1$-$C_6$ haloalkylthio, $C_1$-$C_6$ haloalkylsulfinyl, $C_1$-$C_6$ haloalkylsulfonyl, $C_2$-$C_6$ alkenyl, $C_2$-$C_6$ alkynyl, $C_2$-$C_6$ haloalkenyl, $C_2$-$C_6$ haloalkynyl, $C_2$-$C_6$ haloalkenyloxy, $C_2$-$C_6$ haloalkynyloxy, $C_2$-$C_6$ alkenyloxy, $C_2$-$C_6$ alkynyloxy, $C_2$-$C_6$ alkenylthio, $C_2$-$C_6$ alkynylthio, $C_2$-$C_6$ haloalkenylthio, $C_2$-$C_6$ haloalkynylthio group, and a monocyclic $C_5$-$C_6$ aryl group optionally substituted by a $C_1$-$C_6$ alkyloxy group, a mono or polycyclic $C_5$-$C_{12}$ aryl or mono or polycyclic $C_3$-$C_{12}$ heteroaryl group optionally substituted with a halogen atom, OH, $C_1$-$C_6$ alkyl, or $C_1$-$C_6$ alkoxy; and/or a bridging group of formula —O—$CH_2$—O— or —O—$CH_2CH_2$—O—;

$R_4$ is present when the bond ═ between the carbon 1 and the nitrogen atom is a single bond and is absent when the bond ═ between the carbon 1 and the nitrogen atom is a double bond;

$R_{4a}$ is present when the bond ═ between the carbon 2 and the nitrogen atom is a single bond and is absent when the bond ═ between the carbon 2 and the nitrogen atom is a double bond;

$R_{4a}$ is a $C_1$-$C_6$ alkyl group optionally substituted with substituents independently selected from the group consisting of: halogen atoms, hydroxyl (OH), oxo (═O), nitro, cyano, formyl, $C_3$-$C_7$ cycloalkyl, $C_1$-$C_6$-alkoxy, amino, arylimido optionally substituted, $C_1$-$C_6$alkylamino, di($C_1$-$C_6$)alkylamino, COOH, COO—($C_1$-$C_6$)alkyl, $CONH_2$, CONH($C_1$-$C_6$)alkyl, $C_1$-$C_6$ thioalkyl, SH, S($C_1$-$C_6$)alkyl, S(O)($C_1$-$C_6$)alkyl, $S(O_2)$($C_1$-$C_6$)alkyl, and a mono or polycyclic $C_5$-$C_{12}$ aryl group;

$R_4$ is a hydrogen atom or a $C_1$-$C_6$ alkyl group optionally substituted with substituents independently selected from the group consisting of: halogen atoms, hydroxyl (OH), nitro, cyano, formyl, $C_3$-$C_7$ cycloalkyl, $C_1$-$C_6$-alkoxy, amino, $C_1$-$C_6$alkylamino, di($C_1$-$C_6$)alkylamino, COOH, COO—($C_1$-$C_6$)alkyl, $CONH_2$, CONH($C_1$-$C_6$)alkyl, $C_1$-$C_6$ thioalkyl, SH, S($C_1$-$C_6$)alkyl, S(O)($C_1$-$C_6$)alkyl, $S(O_2)$($C_1$-$C_6$)alkyl, and a mono or polycyclic $C_5$-$C_{12}$ aryl group;

$R_6$ is a hydrogen atom, a halogen atom, a cyano, $C_1$-$C_{10}$ alkyl, $C_3$-$C_{10}$ cycloalkyl, $C_1$-$C_{10}$ alkoxy, $C_1$-$C_{10}$ haloalkoxy, ($C_1$-$C_6$)-alkoxy-($C_1$-$C_6$)-alkyl, ($C_1$-$C_6$)-haloalkoxy-($C_1$-$C_6$)-alkyl, $C_1$-$C_{10}$ thioalkyl, ($C_1$-$C_6$)-alkylthio-($C_1$-$C_6$)-alkyl, $C_1$-$C_{10}$ alkylsulfinyl, $C_1$-$C_{10}$ haloalkylsulfinyl, $C_1$-$C_{10}$ haloalkylsulfonyl, $C_1$-$C_{10}$ alkylsulfonyl, $C_5$-$C_{12}$ arylsulfonyl, formyl, $C_2$-$C_{10}$ alkylcarbonyl, $C_2$-$C_{10}$ alkenyl, $C_2$-$C_{10}$ alkynyl, $C_2$-$C_{10}$ alkenyloxy, $C_2$-$C_{10}$ alkynyloxy, $C_2$-$C_{10}$ alkenylthio, $C_2$-$C_{10}$ alkynylthio, $C_1$-$C_{10}$ haloalkyl, $C_2$-$C_{10}$ haloalkenyl, $C_2$-$C_{10}$ haloalkynyl, $C_2$-$C_{10}$ haloalkylcarbonyl, $C_1$-$C_{10}$ haloalkylthio, $C_2$-$C_{10}$ haloalkenyloxy, $C_2$-$C_{10}$ haloalkynyloxy, $C_2$-$C_{10}$ haloalkenylthio, $C_2$-$C_{10}$ haloalkynylthio, ($C_5$-$C_{12}$)-aryl-($C_1$-$C_6$)-alkyl, ($C_5$-$C_{12}$)-aryl-($C_1$-$C_6$)-alkyl ester or a mono or polycyclic $C_5$-$C_{12}$ aryl or mono or polycyclic $C_3$-$C_{12}$ heteroaryl group, each group being optionally substituted with substituents independently selected from the group consisting of: halogen atoms, hydroxyl (OH), nitro, cyano, formyl, $C_3$-$C_7$ cycloalkyl, $C_1$-$C_6$-alkoxy, amino, $C_1$-$C_6$alkylamino, di($C_1$-$C_6$)alkylamino, COOH, COO—($C_1$-$C_6$)alkyl, $CONH_2$, CONH($C_1$-$C_6$)alkyl, $C_1$-$C_6$ thioalkyl, SH, S($C_1$-$C_6$)alkyl, S(O)($C_1$-$C_6$)alkyl, $S(O_2)$($C_1$-$C_6$)alkyl, and a mono or polycyclic $C_5$-$C_{12}$ aryl group, or a pharmaceutically acceptable salt thereof.

2. The compound of claim 1, wherein:

$R_4$ is present and is a hydrogen atom, or $R_{4a}$ is present and is a group of formula —C(═X)$R_7$ with X representing O or N—$R_8$, $R_7$ representing a $C_1$-$C_6$ alkyl, and $R_8$ representing an aryl optionally substituted with 1 to 3 substituents selected from the group consisting of a halogen atom, $C_1$-$C_6$ alkyl, $C_1$-$C_6$ alkoxy, $C_1$-$C_6$ haloalkyl and $C_1$-$C_6$ haloalkoxy.

3. The compound of claim 1, wherein $R_6$ is a hydrogen atom, a halogen atom, $C_1$-$C_{10}$ alkyl, $C_3$-$C_{10}$ cycloalkyl, $C_1$-$C_{10}$ alkoxy, $C_1$-$C_{10}$ haloalkoxy, ($C_1$-$C_6$)-alkoxy-($C_1$-$C_6$)-alkyl, ($C_1$-$C_6$)-haloalkoxy-($C_1$-$C_6$)-alkyl, $C_1$-$C_{10}$ thioalkyl, ($C_1$-$C_6$)-alkylthio-($C_1$-$C_6$)-alkyl, $C_1$-$C_{10}$ alkylsulfinyl, $C_1$-$C_{10}$ haloalkylsulfinyl, $C_1$-$C_{10}$ haloalkylsulfonyl, $C_1$-$C_{10}$ alkylsulfonyl, $C_5$-$C_{12}$ arylsulfonyl, formyl, $C_2$-$C_{10}$ alkenyl, $C_2$-$C_{10}$ alkenyloxy, $C_2$-$C_{10}$ alkenylthio, $C_1$-$C_{10}$ haloalkyl, $C_2$-$C_{10}$ haloalkenyl, $C_1$-$C_{10}$ haloalkylthio, $C_2$-$C_{10}$ haloalkenyloxy, $C_2$-$C_{10}$ haloalkenylthio, ($C_5$-$C_{12}$)-aryl-($C_1$-$C_6$)-alkyl, ($C_5$-$C_{12}$)-aryl-($C_1$-$C_6$)-alkyl ester, a mono or polycyclic $C_5$-$C_{12}$ aryl, or mono or polycyclic $C_3$-$C_{12}$ heteroaryl group, in which each $C_1$-$C_{10}$ alkyl, $C_3$-$C_{10}$ cycloalkyl, $C_1$-$C_{10}$ alkoxy, $C_1$-$C_{10}$ haloalkoxy, ($C_1$-$C_6$)-alkoxy-($C_1$-$C_6$)-alkyl, ($C_1$-$C_6$)-haloalkoxy-($C_1$-$C_6$)-alkyl, $C_1$-$C_{10}$ thioalkyl, ($C_1$-$C_6$)-alkylthio-($C_1$-$C_6$)-alkyl, $C_1$-$C_{10}$ alkylsulfinyl, $C_1$-$C_{10}$ haloalkylsulfinyl, $C_1$-$C_{10}$ haloalkylsulfonyl, $C_1$-$C_{10}$ alkylsulfonyl, $C_5$-$C_{12}$ arylsulfonyl, formyl, $C_2$-$C_{10}$ alkenyl, $C_2$-$C_{10}$ alkenyloxy, $C_2$-$C_{10}$ alkenylthio, $C_1$-$C_{10}$ haloalkyl, $C_2$-$C_{10}$ haloalkenyl, $C_1$-$C_{10}$ haloalkylthio, $C_2$-$C_{10}$ haloalkenyloxy, $C_2$-$C_{10}$ haloalkenylthio, ($C_5$-$C_{12}$)-aryl-($C_1$-$C_6$)-alkyl, ($C_5$-$C_{12}$)-aryl-($C_1$-$C_6$)-alkyl ester, a mono or polycyclic $C_5$-$C_{12}$ aryl, or mono or polycyclic $C_3$-$C_{12}$ heteroaryl group is optionally substituted with 1 to 3 substituents independently selected from the group consisting of: halogen atoms, hydroxyl (OH), $C_1$-$C_6$-alkoxy, amino, $C_1$-$C_6$_alkylamino, di($C_1$-$C_6$)alkylamino, COOH, COO—($C_1$-$C_6$)alkyl, $CONH_2$, CONH($C_1$-$C_6$)alkyl, $C_1$-$C_6$ thioalkyl, SH, S(O)($C_1$-$C_6$)alkyl, $S(O_2)$($C_1$-$C_6$)alkyl, and a mono $C_5$-$C_6$ aryl group.

4. The compound of claim 3, wherein $R_6$ is a hydrogen atom.

5. The compound of claim 1, wherein $Ar_1$ and $Ar_2$ are independently a mono or polycyclic $C_5$-$C_{12}$ aryl, optionally substituted with 1 to 3 substituents selected from the group consisting of OH, $C_1$-$C_6$ alkyl, $C_3$-$C_7$ cycloalkyl, $C_1$-$C_6$ alkoxy, $C_3$-$C_7$ cycloalkoxy, (1,2 diol)-$C_2$-$C_{10}$ alkoxy, —O—($C_1$-$C_6$)alkyl-O—($C_1$-$C_6$)alkyl-OH, ($C_1$-$C_6$)-alkoxy-($C_1$-$C_6$)-alkyl, $C_1$-$C_6$ haloalkoxy, $C_1$-$C_6$ haloalkoxy alkyl, a $C_1$-$C_6$ alkoxy optionally substituted by a mono or polycyclic $C_5$-$C_{12}$ aryl group, and a bridging group of formula —O—CH$_2$—O— or —O—CH$_2$CH$_2$—O—.

6. The compound of claim 1, wherein $Ar_3$ is substituted with 1 to 3 substituents selected from the group consisting of halogen atoms, OH, $C_1$-$C_6$ alkyl, $C_3$-$C_7$ cycloalkyl, $C_1$-$C_6$ alkoxy, $C_3$-$C_7$ cycloalkoxy, ($C_1$-$C_6$)-alkoxy-($C_1$-$C_6$)-alkyl, $C_2$-$C_6$ alkylcarbonyl, $C_1$-$C_6$ alkylthio, $C_1$-$C_6$ thioalkyl, ($C_1$-$C_6$)-alkylthio-($C_1$-$C_6$)-alkyl, $C_1$-$C_6$alkylsulfinyl, $C_1$-$C_6$ alkylsulfonyl, $C_1$-$C_6$ haloalkyl, $C_1$-$C_6$ haloalkoxy, $C_1$-$C_6$ haloalkoxyalkyl, $C_2$-$C_6$ haloalkylcarbonyl, $C_1$-$C_6$ haloalkylthio, $C_1$-$C_6$ haloalkylsulfinyl, $C_1$-$C_6$ haloalkylsulfonyl, $C_2$-$C_6$ alkenyl, $C_2$-$C_6$ alkynyl, $C_2$-$C_6$ haloalkynyl, $C_2$-$C_6$ haloalkenyl, $C_2$-$C_6$ haloalkenyloxy, $C_2$-$C_6$ haloalkynyloxy, $C_2$-$C_6$ alkenyloxy, $C_2$-$C_6$ alkynyloxy, $C_2$-$C_6$ alkenylthio, $C_2$-$C_6$ alkynylthio, $C_2$-$C_6$ haloalkenylthio, $C_2$-$C_6$ haloalkynylthio group, and a monocyclic $C_5$-$C_6$ aryl group optionally substituted by a $C_1$-$C_6$ alkyloxy group.

7. The compound of claim 1, wherein $R_4$ is present and is a hydrogen atom or $R_{4a}$ is present and is a group of formula —C(=X)R$_7$ with X representing O or N—R$_8$, R$_7$ representing a $C_1$-$C_6$ alkyl, and R$_8$ representing an aryl optionally substituted with 1 to 3 substituents selected from the group consisting of a halogen atom, $C_1$-$C_6$ alkyl, $C_1$-$C_6$ alkoxy, $C_1$-$C_6$ haloalkyl and $C_1$-$C_6$ haloalkoxy;

$R_6$ is a hydrogen atom; and $Ar_1$, $Ar_2$ and $Ar_3$ are independently a mono or polycyclic $C_5$-$C_{12}$ aryl, optionally substituted with 1 to 3 substituents selected from the group consisting of a halogen atom, OH, $C_1$-$C_6$ alkyl, $C_1$-$C_6$ alkoxy, $C_1$-$C_6$ haloalkyl, $C_1$-$C_6$ haloalkoxy, and a bridging group of formula —O—CH$_2$—O— or —O—CH$_2$CH$_2$—O—, or selected from the group consisting of a halogen atom, $C_1$-$C_6$ alkyl, $C_1$-$C_6$ alkoxy, $C_1$-$C_6$ haloalkyl, and $C_1$-$C_6$ haloalkoxy.

8. The compound of claim 1, wherein the compound is a compound of formula (Ia):

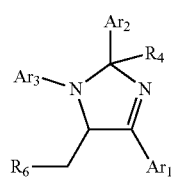

(Ia)

or a pharmaceutically acceptable salt thereof.

9. The compound of claim 1, wherein the compound is selected from the group consisting of:

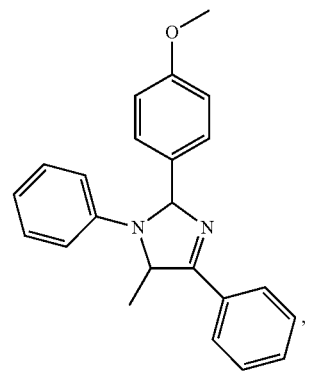

,

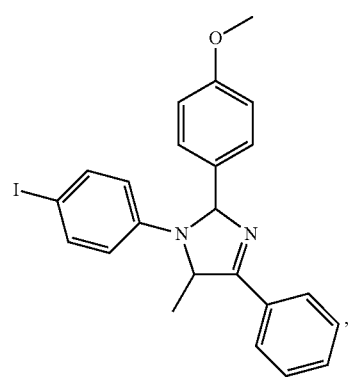

,

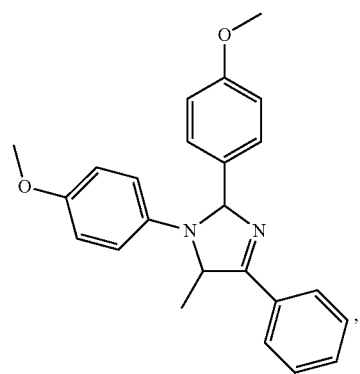

,

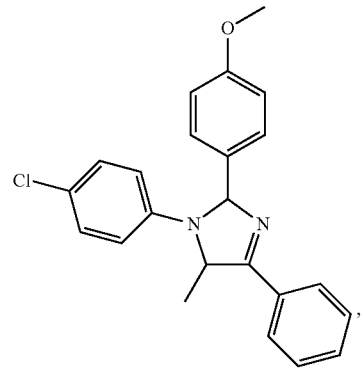

,

-continued
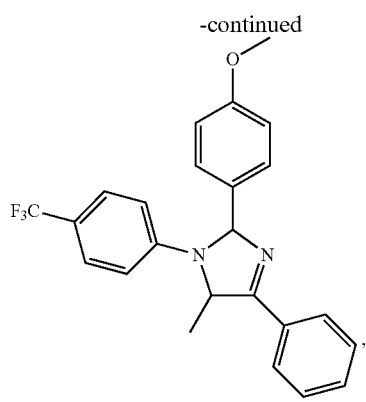
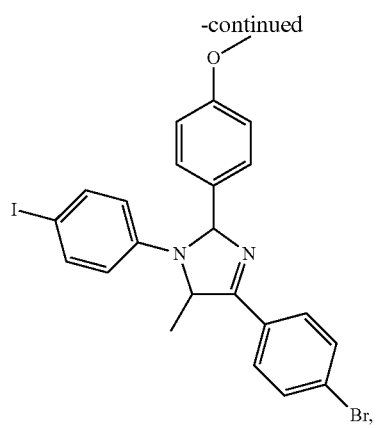
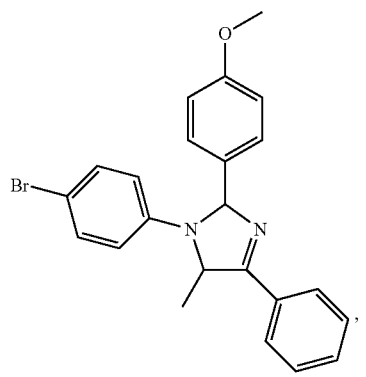
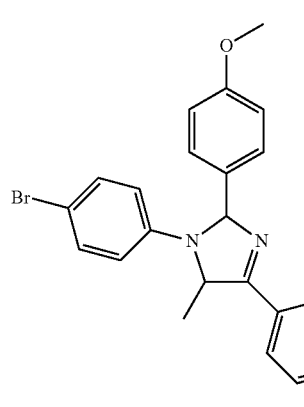
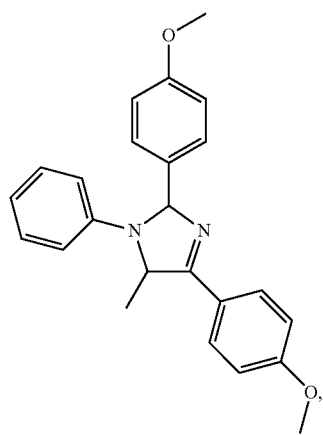
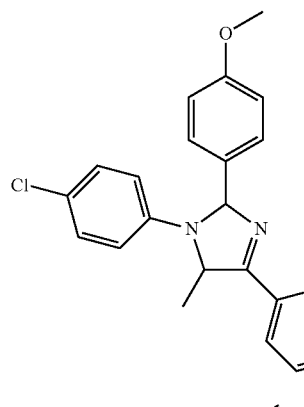
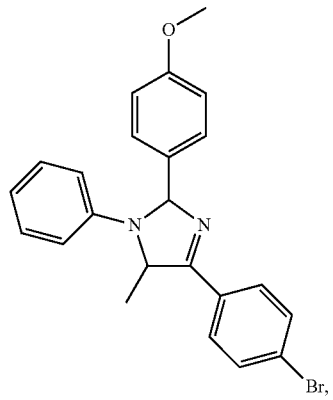
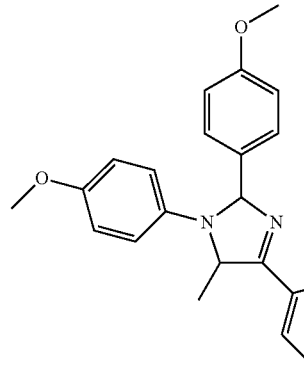

77
-continued
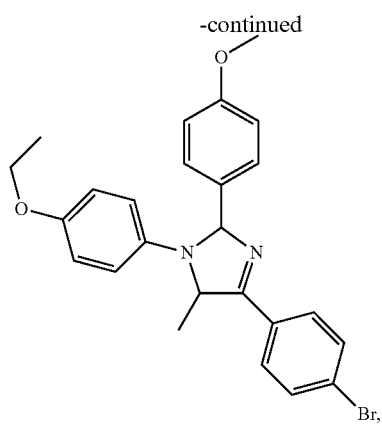
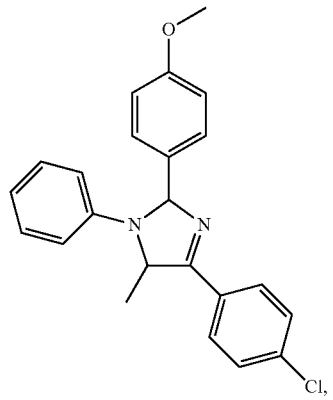
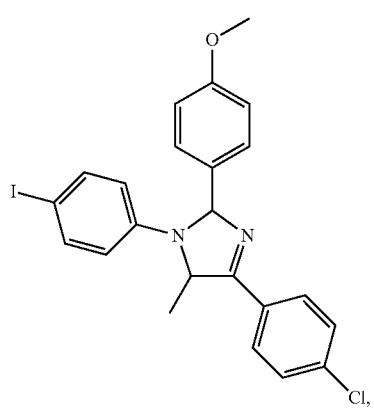
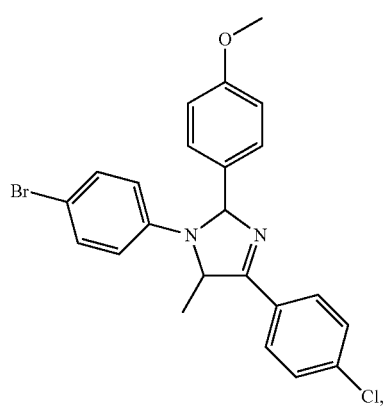
78
-continued
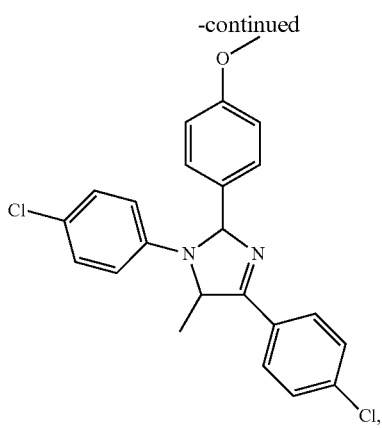
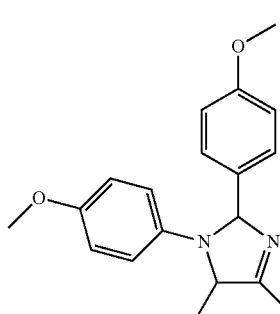
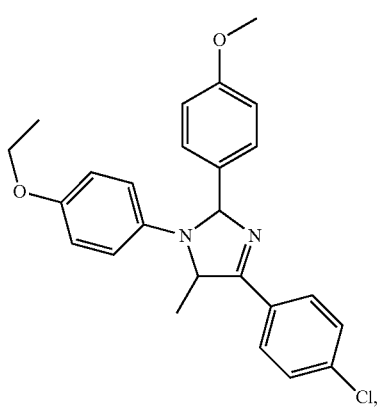
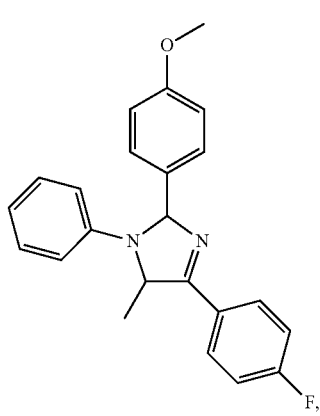

-continued
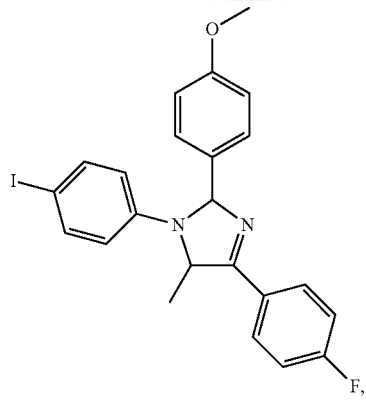
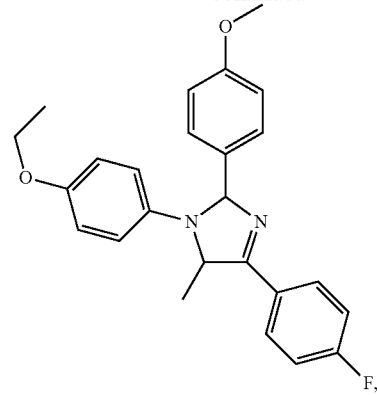
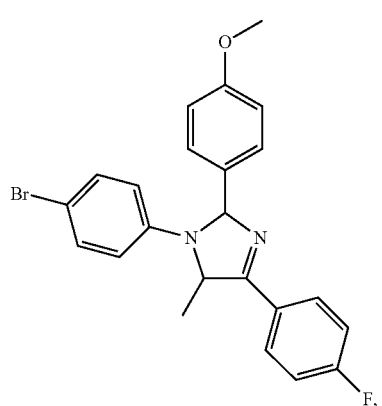
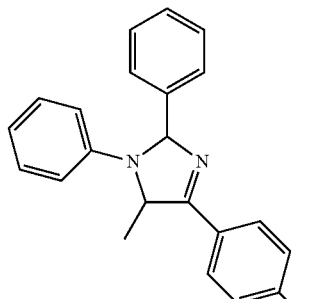
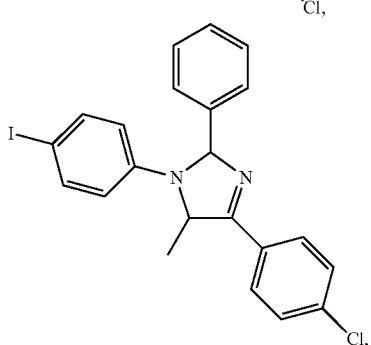
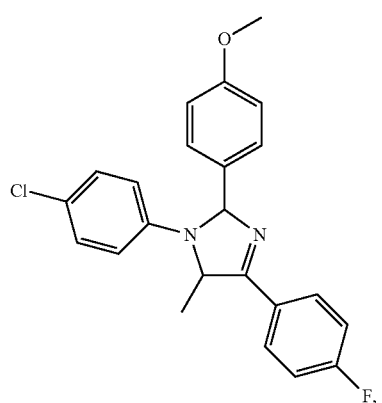
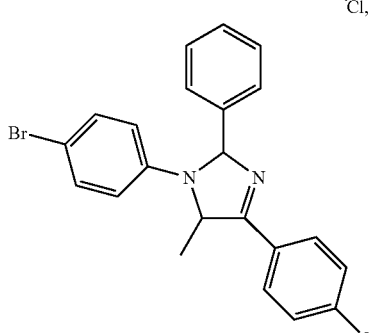
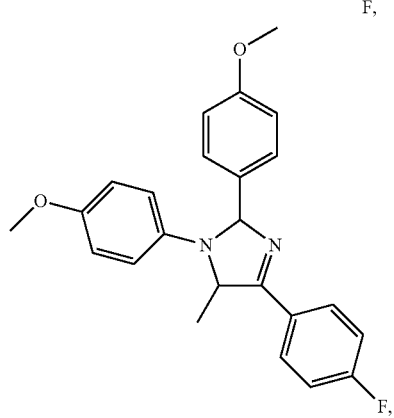
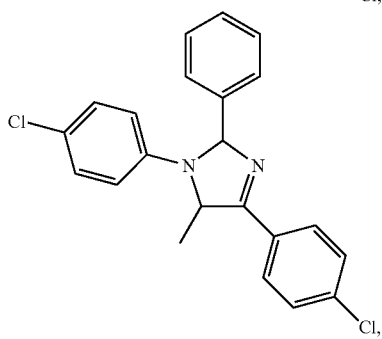

-continued
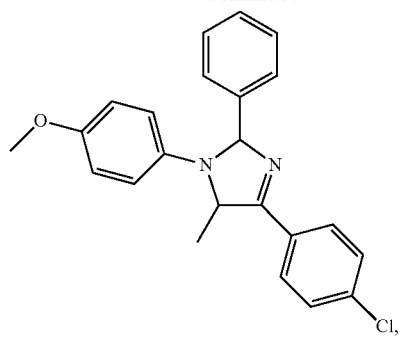
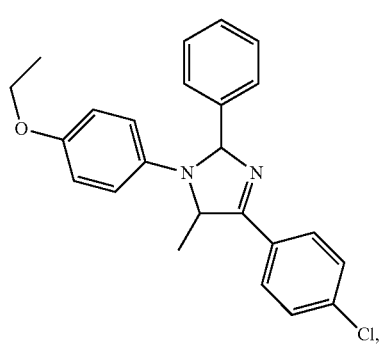
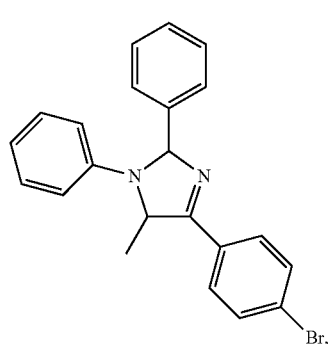
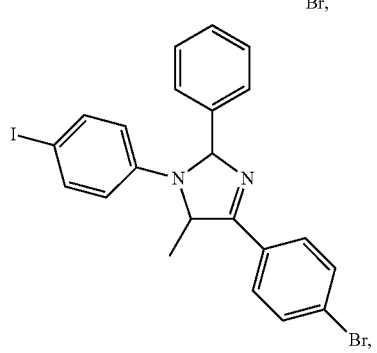
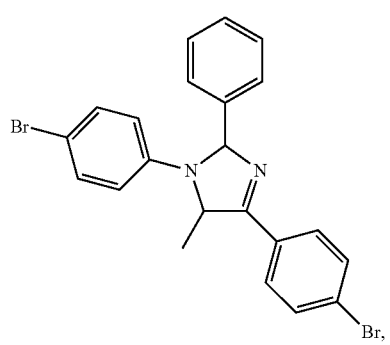
-continued
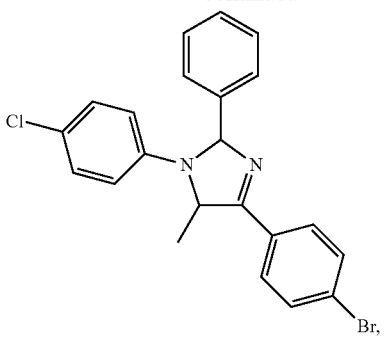
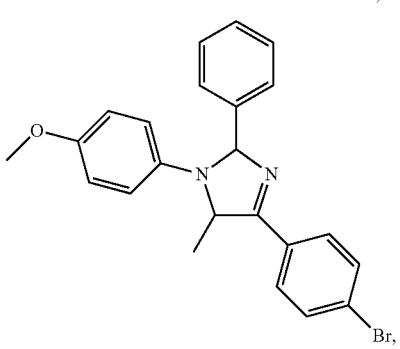
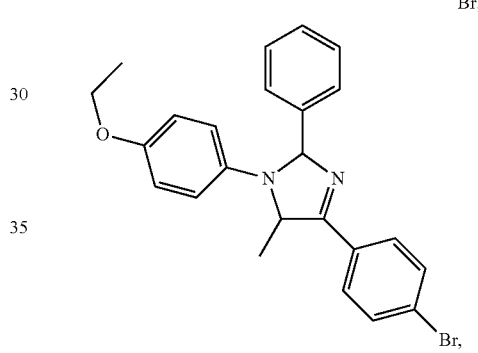
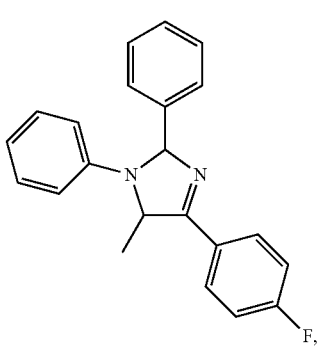
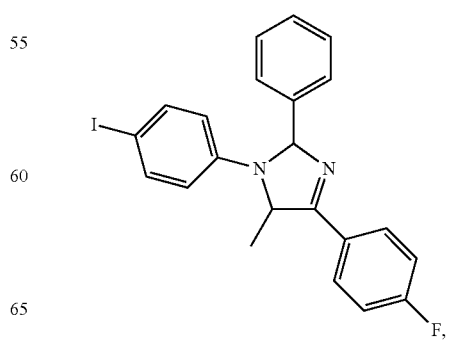

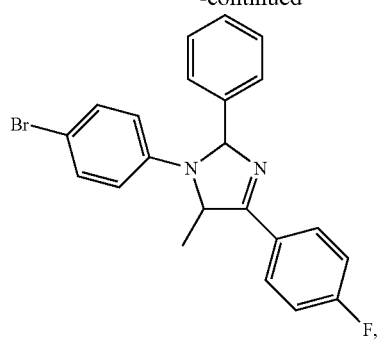
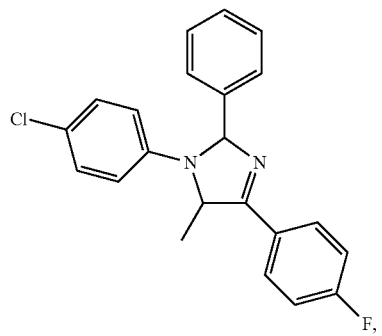
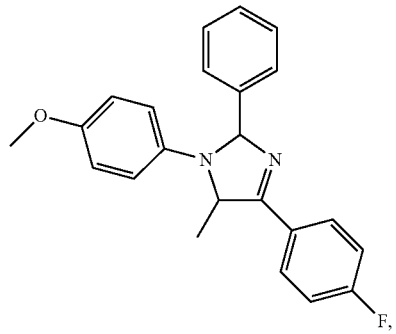
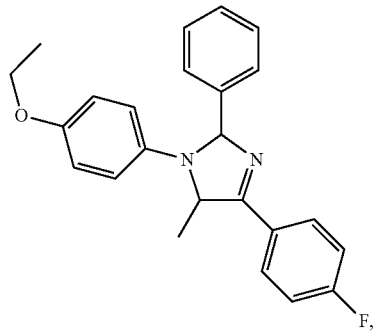
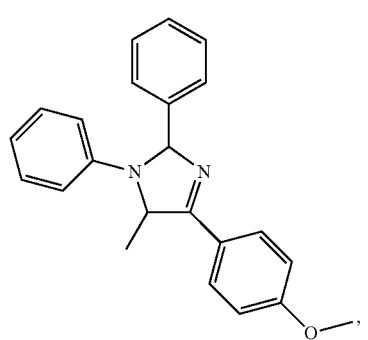
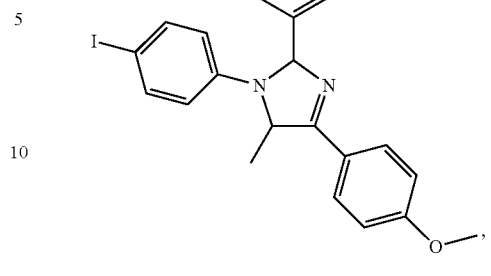
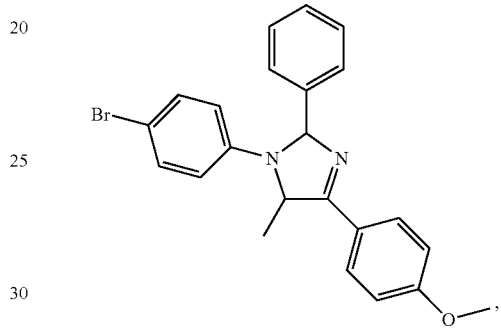
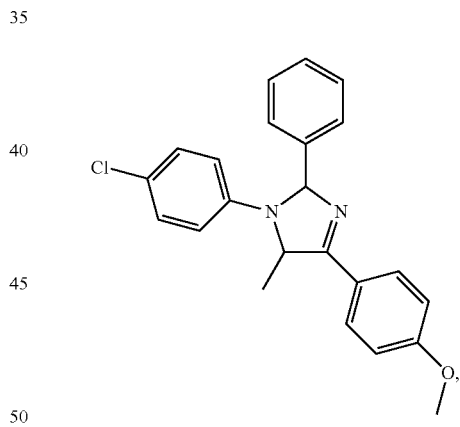
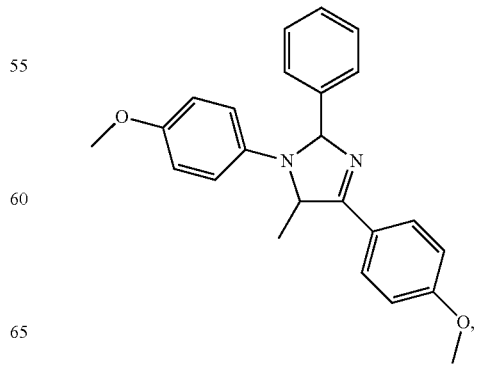

85
-continued
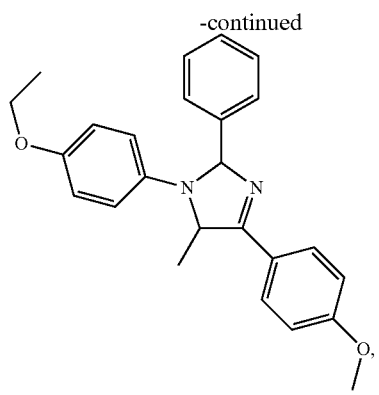
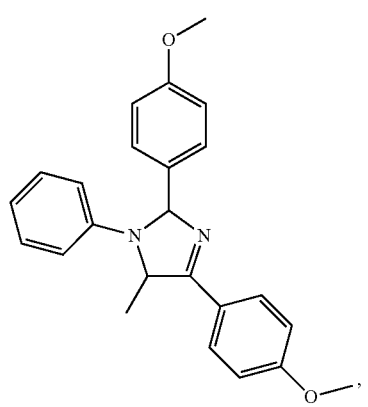
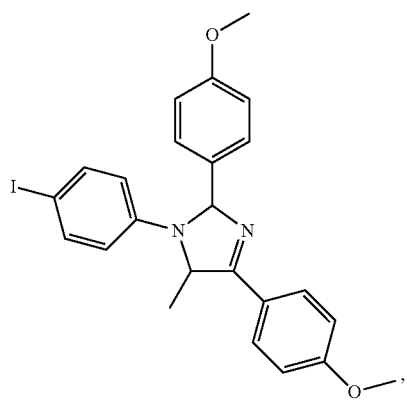
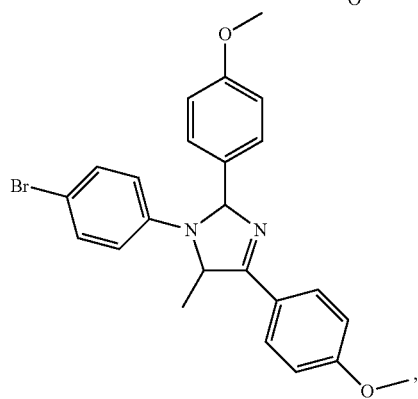
86
-continued
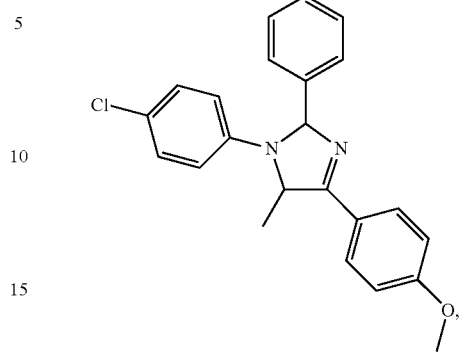
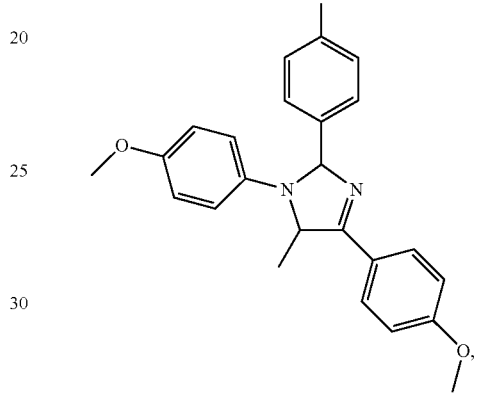
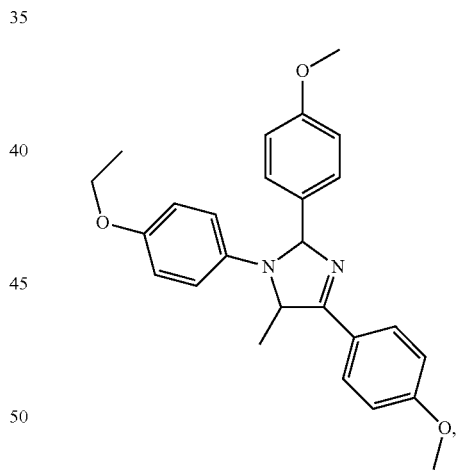
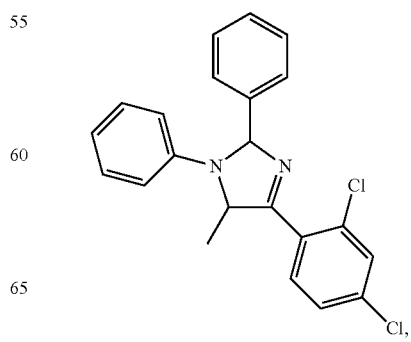

87
-continued
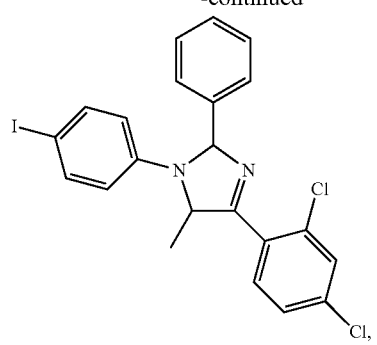
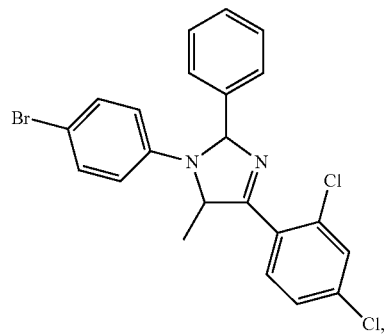
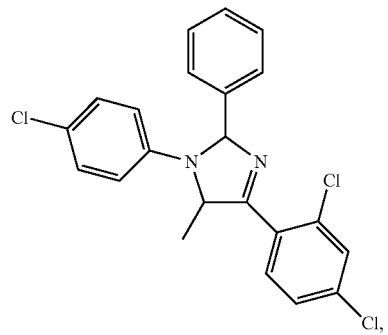
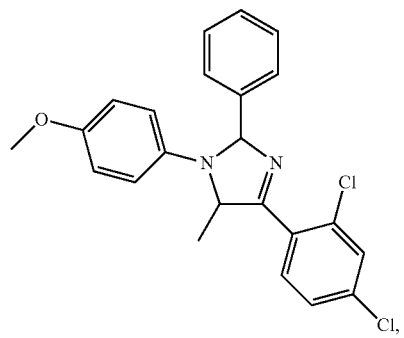
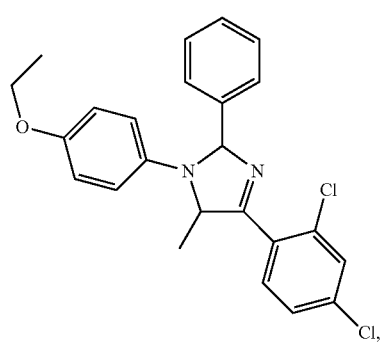
88
-continued
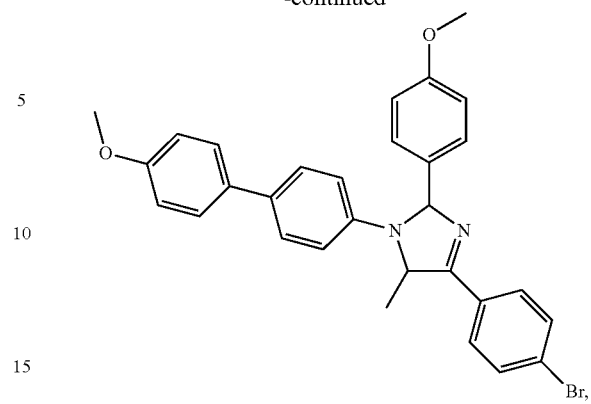
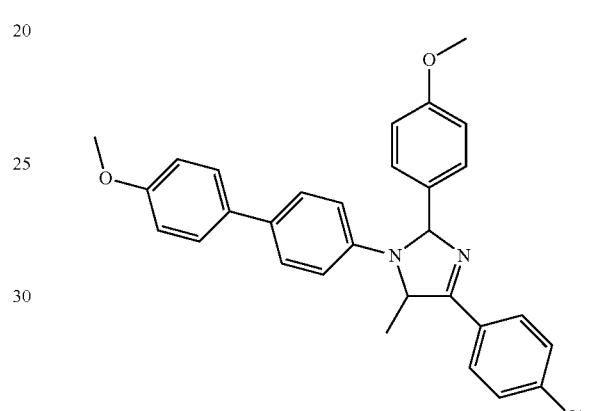
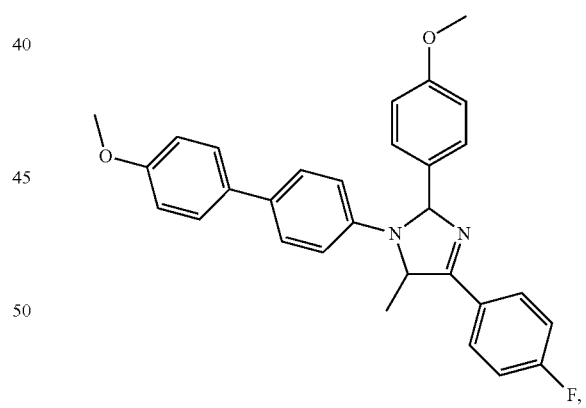
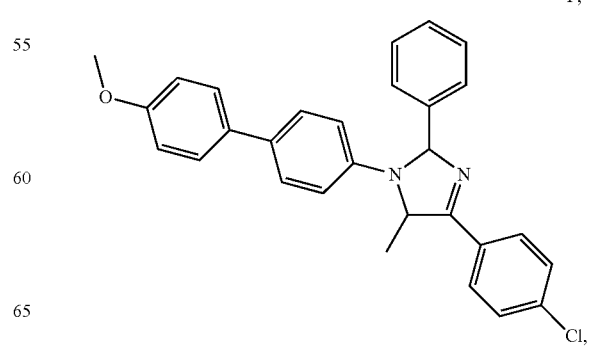

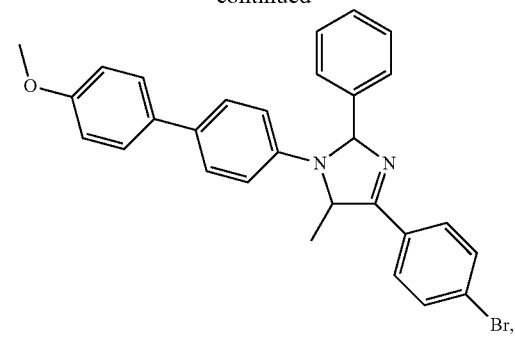
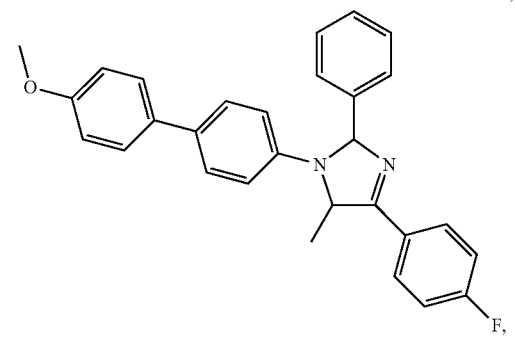
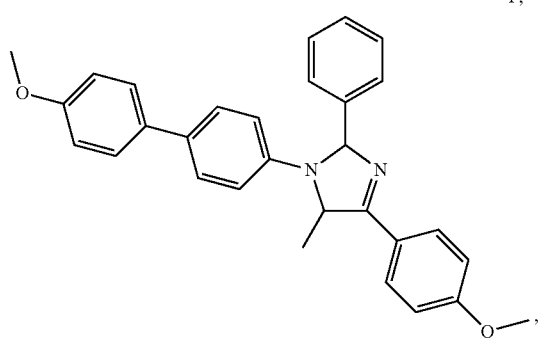
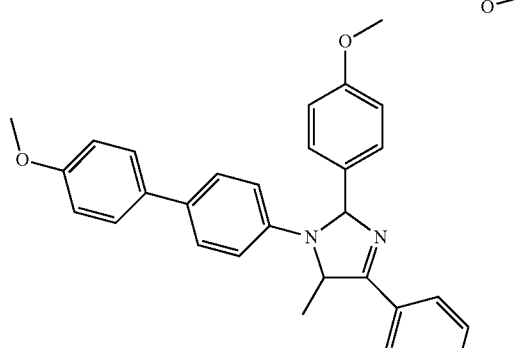
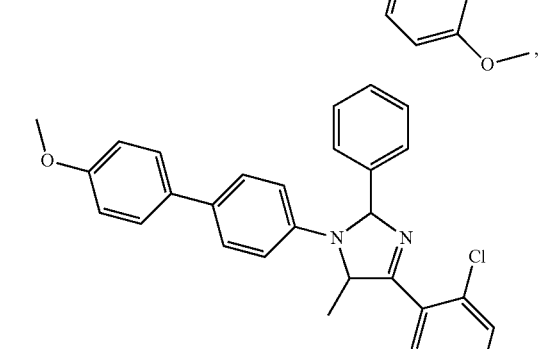
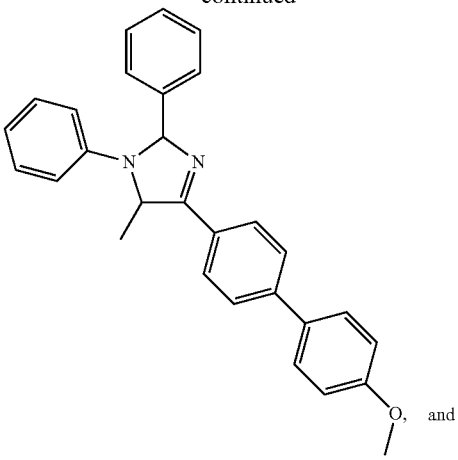
or a pharmaceutically acceptable salt thereof.
10. The compound of claim 1, wherein the compound is selected from the group consisting of:
Compound 1

Compound 2
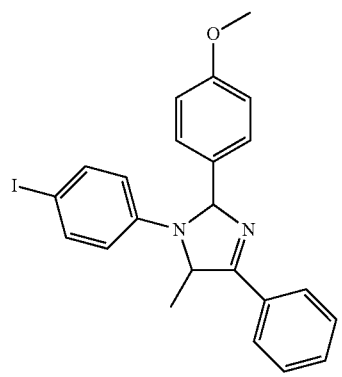
Compound 3
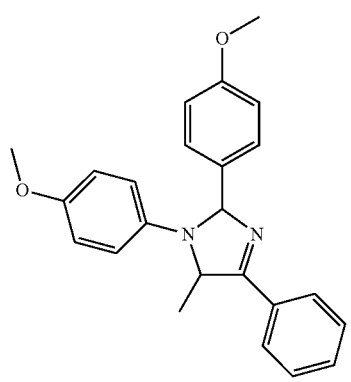
Compound 4
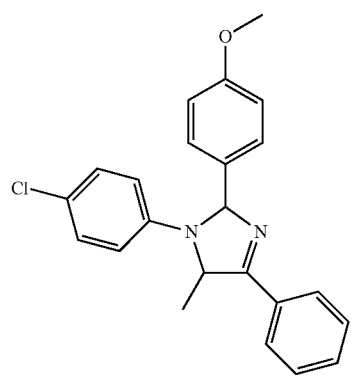
Compound 5
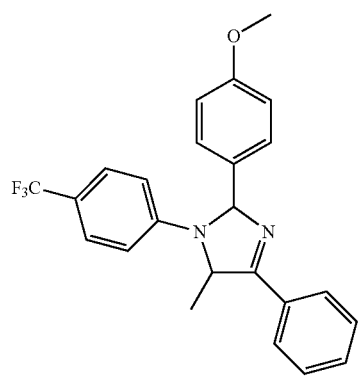
Compound 6
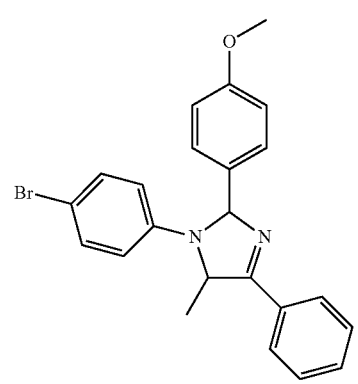
Compound 7
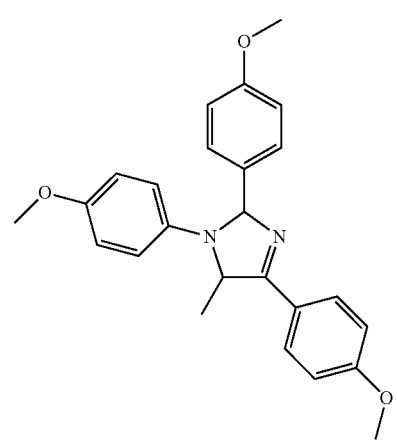
Compound 8
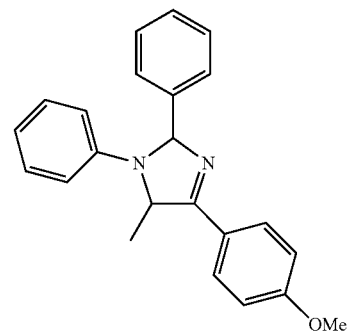
Compound 9
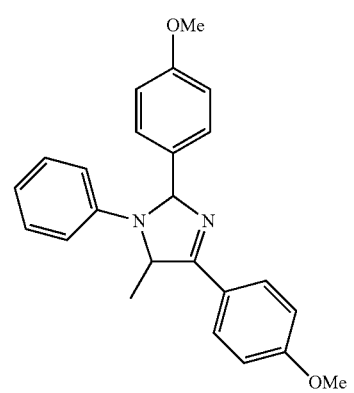

Compound 10
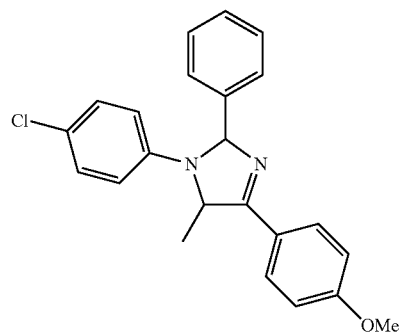
Compound 11
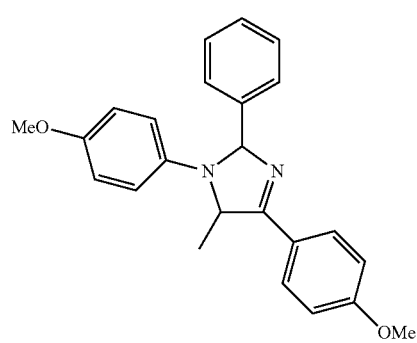
Compound 12
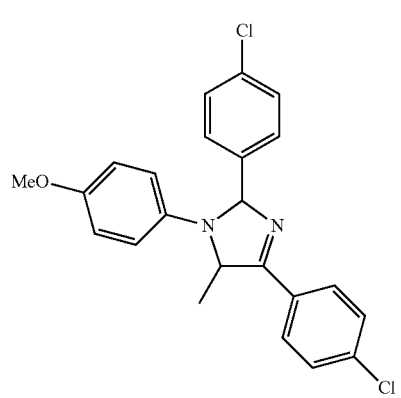
Compound 13
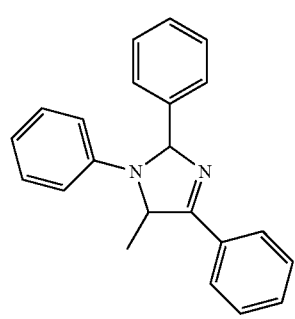
Compound 14
Compound 15
Compound 16
Compound 17
Compound 18
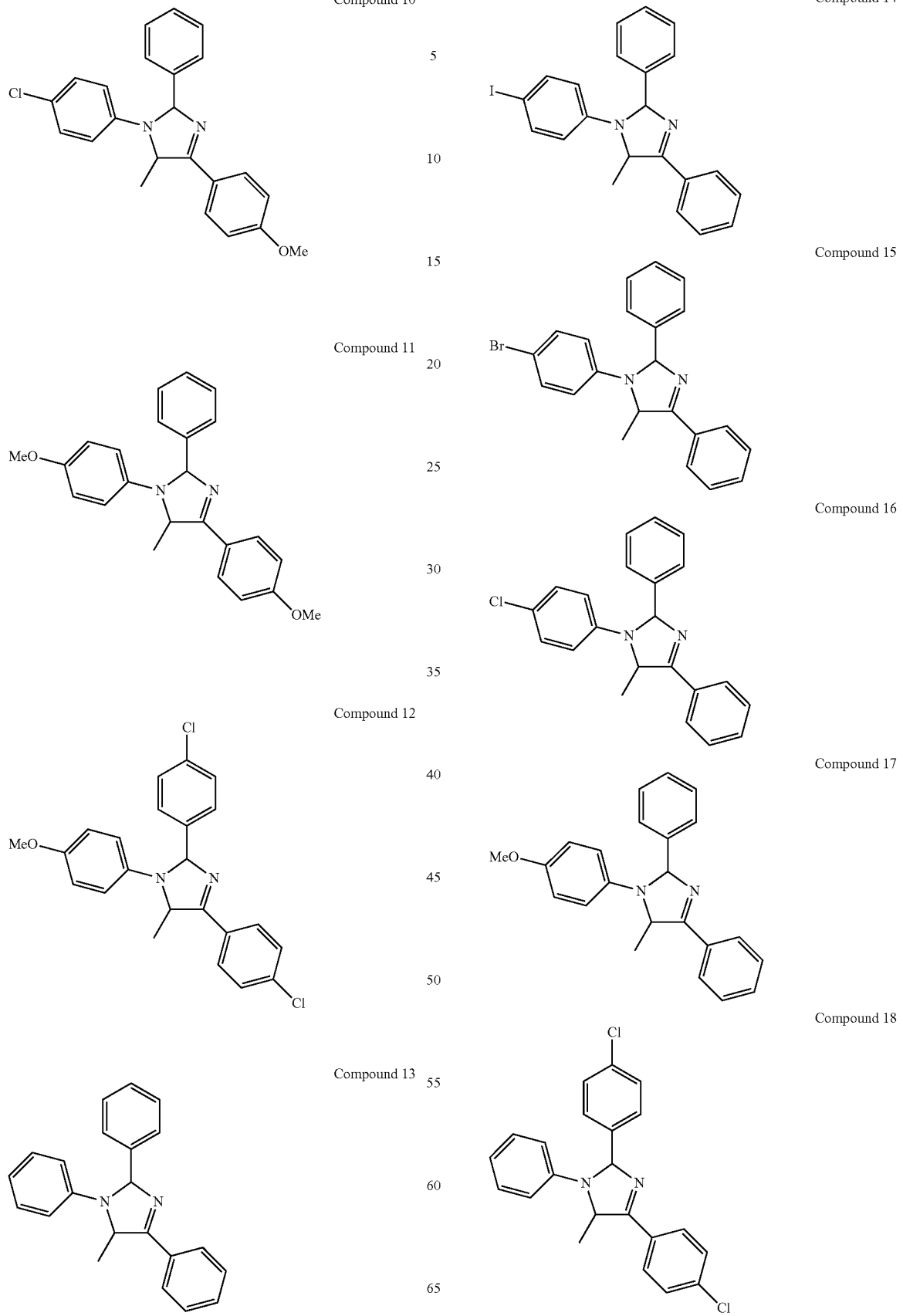

Compound 19
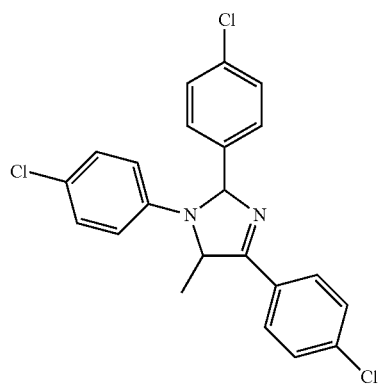
Compound 20
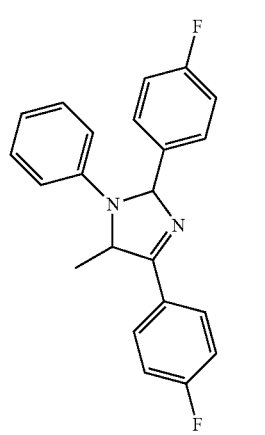
Compound 21
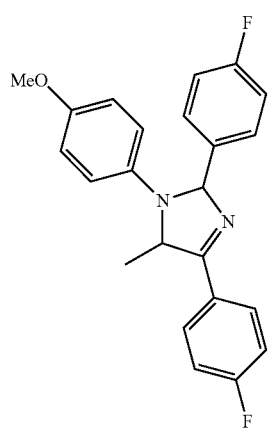
Compound 22
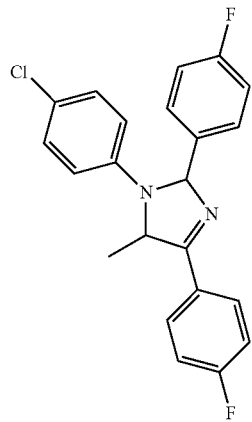
Compound 23
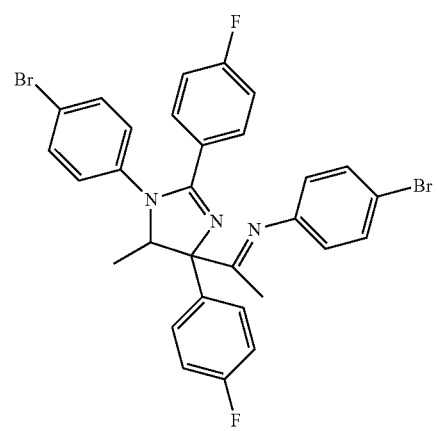
Compound 24
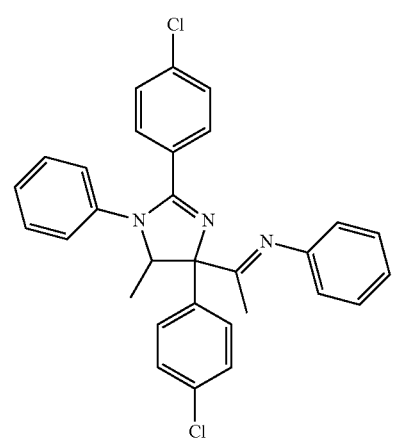
Compound 25
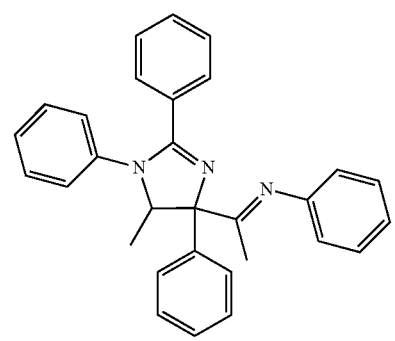
Compound 26
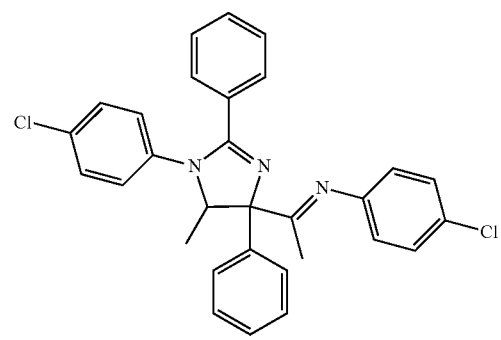

Compound 27

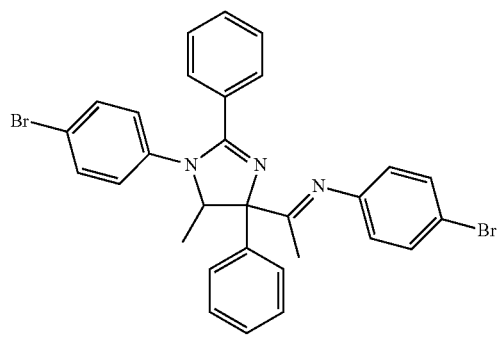

Compound 28

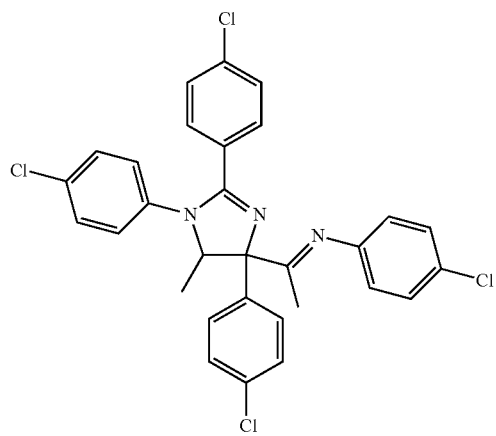

Compound 29

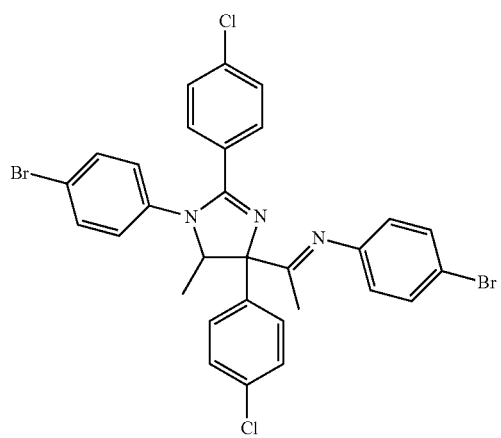

Compound 30

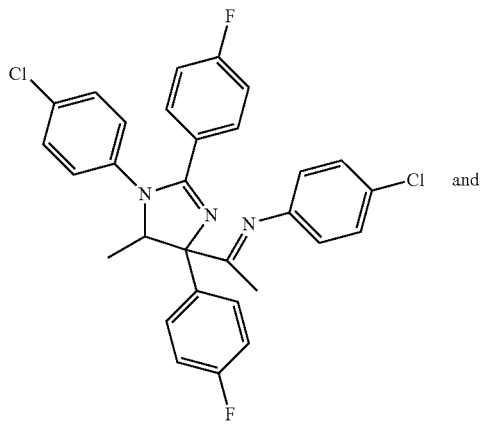

Compound 31

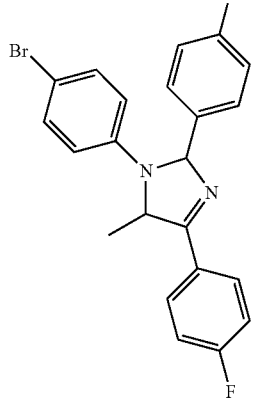

and the pharmaceutically acceptable salts thereof.

11. A method for preparing a compound of formula (I) according to claim 1, comprising:
a) adding a compound of formula (II):

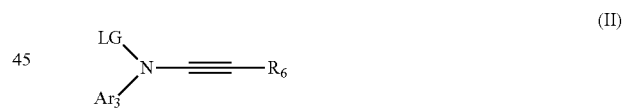

(II)

where
LG represents a leaving group;
$Ar_3$ is a mono or polycyclic $C_5$-$C_{12}$ aryl group or mono or polycyclic $C_3$-$C_{12}$ heteroaryl group, optionally substituted with substituents independently selected from the group consisting of:
halogen atoms, OH, $C_1$-$C_6$ alkyl, $C_3$-$C_7$ cycloalkyl, $C_1$-$C_6$ alkoxy, $C_3$-$C_7$ cycloalkoxy, cyano, formyl, nitro, $C_1$-$C_6$ alkyl, $C_3$-$C_7$ cycloalkyl, $C_1$-$C_6$ alkoxy, $(C_1$-$C_6)$-alkoxy-$(C_1$-$C_6)$-alkyl, $C_2$-$C_6$ alkylcarbonyl, $C_1$-$C_6$ alkylthio, $C_1$-$C_6$ thioalkyl, $(C_1$-$C_6)$-alkylthio-$(C_1$-$C_6)$-alkyl, $C_1$-$C_6$ alkylsulfinyl, $C_1$-$C_6$ alkylsulfonyl, $C_1$-$C_6$ haloalkyl, $C_1$-$C_6$ haloalkoxy, $C_1$-$C_6$ haloalkoxy alkyl, $C_2$-$C_6$ haloalkylcarbonyl, $C_1$-$C_6$ haloalkylthio, $C_1$-$C_6$ haloalkylsulfinyl, $C_1$-$C_6$ haloalkylsulfonyl, $C_2$-$C_6$ alkenyl, $C_2$-$C_6$ alkynyl, $C_2$-$C_6$ haloalkynyl, $C_2$-$C_6$ haloalkenyl, $C_2$-$C_6$ haloalkenyloxy, $C_2$-$C_6$ haloalkynyloxy, $C_2$-$C_6$ alkenyloxy, $C_2$-$C_6$ alkynyloxy, $C_2$-$C_6$ alkenylthio, $C_2$-$C_6$ alkynylthio, $C_2$-$C_6$ haloalkenylthio, $C_2$-$C_6$ haloalkynylthio group, and/or a monocyclic $C_5$-$C_6$ aryl group optionally substituted by a $C_1$-$C_6$ alkyloxy group, a mono or polycyclic $C_5$-$C_{12}$ aryl or mono or polycyclic $C_3$-$C_{12}$ heteroaryl group optionally substituted with a halogen atom, OH, $C_1$-$C_6$ alkyl, or $C_1$-$C_6$ alkoxy; and/or a bridging group of formula —O—CH$_2$—O— or —O—CH$_2$CH$_2$—O—;

$R_6$ is a hydrogen atom, a halogen atom, a cyano, $C_1$-$C_{10}$ alkyl, $C_3$-$C_{10}$ cycloalkyl, $C_1$-$C_{10}$ alkoxy, $C_1$-$C_{10}$ haloalkoxy, ($C_1$-$C_6$)-alkoxy-($C_1$-$C_6$)-alkyl, ($C_1$-$C_6$)-haloalkoxy-($C_1$-$C_6$)-alkyl, $C_1$-$C_{10}$ thioalkyl, ($C_1$-$C_6$)-alkylthio-($C_1$-$C_6$)-alkyl, $C_1$-$C_{10}$ alkylsulfinyl, $C_1$-$C_{10}$ haloalkylsulfinyl, $C_1$-$C_{10}$ haloalkylsulfonyl, $C_1$-$C_{10}$ alkylsulfonyl, $C_5$-$C_{12}$ arylsulfonyl, formyl, $C_2$-$C_{10}$ alkylcarbonyl, $C_2$-$C_{10}$ alkenyl, $C_2$-$C_{10}$ alkynyl, $C_2$-$C_{10}$ alkenyloxy, $C_2$-$C_{10}$ alkynyloxy, $C_2$-$C_{10}$ alkenylthio, $C_2$-$C_{10}$ alkynylthio, $C_1$-$C_{10}$ haloalkyl, $C_2$-$C_{10}$ haloalkenyl, $C_2$-$C_{10}$ haloalkynyl, $C_2$-$C_{10}$ haloalkylcarbonyl, $C_1$-$C_{10}$ haloalkylthio, $C_2$-$C_{10}$ haloalkenyloxy, $C_2$-$C_{10}$ haloalkynyloxy, $C_2$-$C_{10}$ haloalkenylthio, $C_2$-$C_{10}$ haloalkynylthio, ($C_5$-$C_{12}$)-aryl-($C_1$-$C_6$)-alkyl, ($C_5$-$C_{12}$)-aryl-($C_1$-$C_6$)-alkyl ester or a mono or polycyclic $C_5$-$C_{12}$ aryl or mono or polycyclic $C_3$-$C_{12}$ heteroaryl group, each group being optionally substituted with substituents independently selected from the group consisting of: halogen atoms, hydroxyl (OH), nitro, cyano, formyl, $C_3$-$C_7$ cycloalkyl, $C_1$-$C_6$-alkoxy, amino, $C_1$-$C_6$alkylamino, di($C_1$-$C_6$)alkylamino, COOH, COO—($C_1$-$C_6$)alkyl, CONH$_2$, CONH($C_1$-$C_6$)alkyl, $C_1$-$C_6$ thioalkyl, SH, S($C_1$-$C_6$)alkyl, S(O)($C_1$-$C_6$)alkyl, S(O$_2$)($C_1$-$C_6$)alkyl, a mono or polycyclic $C_5$-$C_{12}$ aryl group, to a compound of formula (III):

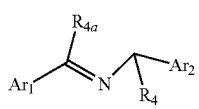

(III)

where

Ar$_1$ and Ar$_2$ are identical or different and are independently a mono or polycyclic $C_5$-$C_{12}$ aryl or mono or polycyclic $C_3$-$C_{12}$ heteroaryl group, optionally substituted with:

one to three substituents independently selected from the group consisting of: a halogen atom, OH, $C_1$-$C_6$ alkyl, $C_3$-$C_7$ cycloalkyl, $C_1$-$C_6$ alkoxy, $C_3$-$C_7$ cycloalkoxy, nitro, cyano, formyl, amino-$C_1$-$C_{10}$ alkoxy, (carboxylic acid)-$C_1$-$C_{10}$ alkoxy, (carboxylic ($C_1$-$C_6$)alkyl ester)-$C_1$-$C_{10}$ alkoxy, (1,2 diol)-$C_2$-$C_{10}$ alkoxy, —O—($C_1$-$C_6$)alkyl-O—($C_1$-$C_6$)alkyl-OH, ($C_1$-$C_6$)-alkoxy-($C_1$-$C_6$)-alkyl, $C_2$-$C_6$ alkylcarbonyl, $C_1$-$C_6$ alkylthio, $C_1$-$C_6$ thioalkyl, ($C_1$-$C_6$)-alkylthio-($C_1$-$C_6$)-alkyl, $C_1$-$C_6$ alkylsulfinyl, $C_1$-$C_6$ alkylsulfonyl, $C_1$-$C_6$ haloalkyl, $C_1$-$C_6$ haloalkoxy, $C_1$-$C_6$ haloalkoxy alkyl, $C_2$-$C_6$ haloalkylcarbonyl, $C_1$-$C_6$ haloalkylthio, $C_1$-$C_6$ haloalkylsulfinyl, $C_1$-$C_6$ haloalkylsulfonyl, $C_2$-$C_6$ alkenyl, $C_2$-$C_6$ alkynyl, $C_2$-$C_6$ haloalkynyl, $C_2$-$C_6$ haloalkenyl, $C_2$-$C_6$ haloalkenyloxy, $C_2$-$C_6$ haloalkynyloxy, $C_2$-$C_6$ alkenyloxy, $C_2$-$C_6$ alkynyloxy, $C_2$-$C_6$ alkenylthio, $C_2$-$C_6$ alkynylthio, $C_2$-$C_6$ haloalkenylthio, $C_2$-$C_6$ haloalkynylthio and/or a $C_1$-$C_6$ alkoxy optionally substituted by a mono or polycyclic $C_5$-$C_{12}$ aryl group, a mono or polycyclic $C_5$-$C_{12}$ aryl or mono or polycyclic $C_3$-$C_{12}$ heteroaryl group optionally substituted with a halogen atom, OH, $C_1$-$C_6$ alkyl, or $C_1$-$C_6$ alkoxy; and/or a bridging group of formula —O—CH$_2$—O— or —O—CH$_2$CH$_2$—O—;

$R_4$ is present when the bond ═ between the carbon 1 and the nitrogen atom in the compound of formula (I) is a single bond and is absent when the bond ═ between the carbon 1 and the nitrogen atom in the compound of formula (I) is a double bond;

$R_{4a}$ is present when the bond ═ between the carbon 2 and the nitrogen atom in the compound of formula (I) is a single bond and is absent when the bond ═ between the carbon 2 and the nitrogen atom in the compound of formula (I) is a double bond;

$R_{4a}$ is a $C_1$-$C_6$ alkyl group optionally substituted with substituents independently selected from the group consisting of: halogen atoms, hydroxyl (OH), oxo (═O), nitro, cyano, formyl, $C_3$-$C_7$ cycloalkyl, $C_1$-$C_6$-alkoxy, amino, arylimido optionally substituted, $C_1$-$C_6$alkylamino, di($C_1$-$C_6$)alkylamino, COOH, COO—($C_1$-$C_6$)alkyl, CONH$_2$, CONH($C_1$-$C_6$)alkyl, $C_1$-$C_6$ thioalkyl, SH, S($C_1$-$C_6$)alkyl, S(O)($C_1$-$C_6$)alkyl, S(O$_2$)($C_1$-$C_6$)alkyl, a mono or polycyclic $C_5$-$C_{12}$ aryl group;

$R_4$ is a hydrogen atom or a $C_1$-$C_6$ alkyl group optionally substituted with substituents independently selected from the group consisting of: halogen atoms, hydroxyl (OH), nitro, cyano, formyl, $C_3$-$C_7$ cycloalkyl, $C_1$-$C_6$-alkoxy, amino, $C_1$-$C_6$alkylamino, di($C_1$-$C_6$)alkylamino, COOH, COO—($C_1$-$C_6$)alkyl, CONH$_2$, CONH ($C_1$-$C_6$)alkyl, $C_1$-$C_6$ thioalkyl, SH, S($C_1$-$C_6$)alkyl, S(O) ($C_1$-$C_6$)alkyl, S(O$_2$)($C_1$-$C_6$)alkyl, a mono or polycyclic $C_5$-$C_{12}$ aryl group;

in the presence of a base B1 selected from the group consisting of hydroxide salts, C1-C6 alkoxide salts, and phenoxide salts, wherein optionally (a) is carried out under pressure and/or at a temperature above 50° C.; and b) isolating the compound of formula (I).

12. A conjugate of a compound of formula (I) or (I') with an antibiotic through a linker, represented by formula (IV):

Inhibitor-Linker-Antibio     (IV)

wherein Inhibitor is a compound of formula (I) as defined in claim 1, or a compound of formula (I')

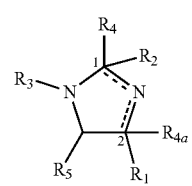

(I')

wherein

═ represents a single or double bond, with the proviso that one of the two bonds ═ is a single bond and the other is a double bond;

$R_1$, $R_2$, and $R_3$ are identical or different, and are independently one from each other a hydrogen, halogen, nitro, cyano, formyl, $C_1$-$C_{10}$ alkyl, $C_3$-$C_{10}$ cycloalkyl, 3- to 8-membered heterocycle, $C_1$-$C_{10}$ alkoxy, $C_2$-$C_{10}$ alkylcarbonyl, a $C_6$-$C_{13}$ arylcarbonyl, a $C_4$-$C_{13}$ heteroaryl carbonyl, $C_1$-$C_{10}$ haloalkoxy, $(C_1$-$C_6)$-alkoxy-$(C_1$-$C_6)$-alkyl, $(C_1$-$C_6)$-haloalkoxy-$(C_1$-$C_6)$-alkyl, $C_1$-$C_{10}$ thioalkyl, $(C_5$-$C_{12})$-aryl-$(C_1$-$C_6)$-alkyl ester, $(C_1$-$C_6)$-alkylthio-$(C_1$-$C_6)$-alkyl, $C_1$-$C_{10}$ alkylsulfinyl, $C_1$-$C_{10}$ haloalkylsulfinyl, $C_1$-$C_{10}$ haloalkylsulfonyl, $C_1$-$C_{10}$ alkylsulfonyl, $C_5$-$C_{12}$ arylsulfonyl, $C_2$-$C_{10}$ alkenyl, $C_2$-$C_{10}$ alkynyl, $C_2$-$C_{10}$ alkenyloxy, $C_2$-$C_{10}$ alkynyloxy, $C_2$-$C_{10}$ alkenylthio, $C_2$-$C_{10}$ alkynylthio, $C_1$-$C_{10}$ haloalkyl, $C_2$-$C_{10}$ haloalkenyl, $C_2$-$C_{10}$ haloalkynyl, $C_2$-$C_{10}$ haloalkylcarbonyl, $C_1$-$C_{10}$ haloalkylthio, $C_2$-$C_{10}$ haloalkenyloxy, $C_2$-$C_{10}$ haloalkynyloxy, $C_2$-$C_{10}$ haloalkenylthio, $C_2$-$C_{10}$ haloalkynylthio, $(C_5$-$C_{12})$-aryl-$(C_1$-$C_6)$-alkyl, a $(C_1$-$C_6)$alkyl-$(C_5$-$C_{12})$aryl, a $(C_1$-$C_6)$alkyl-$(C_5$-$C_{12})$heteroaryl, a mono or polycyclic $C_5$-$C_{12}$ aryl or mono or polycyclic $C_3$-$C_{12}$ heteroaryl fragments, wherein the $C_1$-$C_{10}$ alkyl, $C_3$-$C_{10}$ cycloalkyl, 3- to 8-membered heterocycle, $C_1$-$C_{10}$ alkoxy, $C_2$-$C_{10}$ alkylcarbonyl, a $C_6$-$C_{13}$ arylcarbonyl, a $C_4$-$C_{13}$ heteroaryl carbonyl, $C_1$-$C_{10}$ haloalkoxy, $(C_1$-$C_6)$-alkoxy-$(C_1$-$C_6)$-alkyl, $(C_1$-$C_6)$-haloalkoxy-$(C_1$-$C_6)$-alkyl, $C_1$-$C_{10}$ thioalkyl, $(C_5$-$C_{12})$-aryl-$(C_1$-$C_6)$-alkyl ester, $(C_1$-$C_6)$-alkylthio-$(C_1$-$C_6)$-alkyl, $C_1$-$C_{10}$ alkylsulfinyl, $C_1$-$C_{10}$ haloalkylsulfinyl, $C_1$-$C_{10}$ haloalkylsulfonyl, $C_1$-$C_{10}$ alkylsulfonyl, $C_5$-$C_{12}$ arylsulfonyl, $C_2$-$C_{10}$ alkenyl, $C_2$-$C_{10}$ alkynyl, $C_2$-$C_{10}$ alkenyloxy, $C_2$-$C_{10}$ alkynyloxy, $C_2$-$C_{10}$ alkenylthio, $C_2$-$C_{10}$ alkynylthio, $C_1$-$C_{10}$ haloalkyl, $C_2$-$C_{10}$ haloalkenyl, $C_2$-$C_{10}$ haloalkynyl, $C_2$-$C_{10}$ haloalkylcarbonyl, $C_1$-$C_{10}$ haloalkylthio, $C_2$-$C_{10}$ haloalkenyloxy, $C_2$-$C_{10}$ haloalkynyloxy, $C_2$-$C_{10}$ haloalkenylthio, $C_2$-$C_{10}$ haloalkynylthio, $(C_5$-$C_{12})$-aryl-$(C_1$-$C_6)$-alkyl, a $(C_1$-$C_6)$alkyl-$(C_5$-$C_{12})$aryl, a $(C_1$-$C_6)$alkyl-$(C_5$-$C_{12})$heteroaryl, a mono or polycyclic $C_5$-$C_{12}$ aryl or mono or polycyclic $C_3$-$C_{12}$ heteroaryl fragment is optionally substituted with:

one or several (1 to 3) halogen atoms, hydroxyl (OH), nitro, cyano, formyl, $C_1$-$C_6$ alkyl, $C_3$-$C_7$ cycloalkyl, 3- to 8-membered heterocycle, amino-$C_1$-$C_{10}$ alkoxy, (carboxylic acid)-$C_1$-$C_{10}$ alkoxy, (carboxylic $(C_1$-$C_6)$alkyl ester)-$C_1$-$C_{10}$ alkoxy, (1,2 diol)-$C_2$-$C_{10}$ alkoxy, —O—$(C_1$-$C_6)$alkyl-O—$(C_1$-$C_6)$alkyl-OH, $(C_1$-$C_6)$-alkoxy-$(C_1$-$C_6)$-alkyl, $C_2$-$C_6$ alkylcarbonyl, $C_1$-$C_6$ alkylthio, $C_1$-$C_6$ thioalkyl, $(C_1$-$C_6)$-alkylthio-$(C_1$-$C_6)$-alkyl, $C_1$-$C_6$ alkylsulfinyl, $C_1$-$C_6$ alkylsulfonyl, $C_1$-$C_6$ haloalkyl, $C_1$-$C_6$ haloalkoxy, $C_1$-$C_6$ haloalkoxy alkyl, $C_2$-$C_6$ haloalkylcarbonyl, $C_1$-$C_6$ haloalkylthio, $C_1$-$C_6$ haloalkylsulfinyl, $C_1$-$C_6$ haloalkylsulfonyl, $C_2$-$C_6$ alkenyl, $C_2$-$C_6$ alkynyl, $C_2$-$C_6$ haloalkynyl, $C_2$-$C_6$ haloalkenyl, $C_2$-$C_6$ haloalkenyloxy, $C_2$-$C_6$ haloalkynyloxy, $C_2$-$C_6$ alkenyloxy, $C_2$-$C_6$ alkynyloxy, $C_2$-$C_6$ alkenylthio, $C_2$-$C_6$ alkynylthio, $C_2$-$C_6$ haloalkenylthio, $C_2$-$C_6$ haloalkynylthio and/or a $C_1$-$C_6$ alkoxy optionally substituted by a mono or polycyclic $C_5$-$C_{12}$ aryl group, a mono or polycyclic $C_5$-$C_{12}$ aryl or mono or polycyclic $C_3$-$C_{12}$ heteroaryl group optionally substituted with a halogen atom, OH, $C_1$-$C_6$ alkyl, or $C_1$-$C_6$ alkoxy; and/or a bridging group of formula —O—$CH_2$—O— or —O—$CH_2CH_2$—O—, said bridging group being useable when the fragment contains an aryl or heteroaryl moiety, or when the fragment is a $C_6$-$C_{13}$ arylcarbonyl, a $C_4$-$C_{13}$ heteroaryl carbonyl, $(C_5$-$C_{12})$-aryl-$(C_1$-$C_6)$-alkyl ester, $C_5$-$C_{12}$ arylsulfonyl, $(C_5$-$C_{12})$-aryl-$(C_1$-$C_6)$-alkyl, a $(C_1$-$C_6)$alkyl-$(C_5$-$C_{12})$aryl, a $(C_1$-$C_6)$alkyl-$(C_5$-$C_{12})$heteroaryl, a mono or polycyclic $C_5$-$C_{12}$ aryl or mono or polycyclic $C_3$-$C_{12}$ heteroaryl fragment;

$R_4$ is present when the bond ═ between the carbon 1 and the nitrogen atom is a single bond and is absent when the bond ═ between the carbon 1 and the nitrogen atom is a double bond;

$R_{4a}$ is present when the bond ═ between the carbon 2 and the nitrogen atom is a single bond and is absent when the bond ═ between the carbon 2 and the nitrogen atom is a double bond;

$R_4$ is a hydrogen atom or a $C_1$-$C_6$ alkyl group optionally substituted with substituents independently selected from the group consisting of: halogen atoms, hydroxyl (OH), nitro, cyano, formyl, $C_3$-$C_7$ cycloalkyl, 3- to 8-membered heterocycle, $C_1$-$C_6$-alkoxy, amino, $C_1$-$C_6$alkylamino, di$(C_1$-$C_6)$alkylamino, COOH, COO—$(C_1$-$C_6)$alkyl, $CONH_2$, CONH$(C_1$-$C_6)$alkyl, $C_1$-$C_6$ thioalkyl, SH, S$(C_1$-$C_6)$alkyl, S(O)$(C_1$-$C_6)$alkyl, S$(O_2)(C_1$-$C_6)$alkyl, and a mono or polycyclic $C_5$-$C_{12}$ aryl group;

$R_{4a}$ is a $C_1$-$C_6$ alkyl group optionally substituted with substituents independently selected from the group consisting of: halogen atoms, hydroxyl (OH), oxo (═O), nitro, cyano, formyl, $C_3$-$C_7$ cycloalkyl, $C_1$-$C_6$-alkoxy, amino, arylimido optionally substituted, $C_1$-$C_6$alkylamino, di$(C_1$-$C_6)$alkylamino, COOH, COO—$(C_1$-$C_6)$alkyl, $CONH_2$, CONH$(C_1$-$C_6)$alkyl, $C_1$-$C_6$ thioalkyl, SH, S$(C_1$-$C_6)$alkyl, S(O)$(C_1$-$C_6)$alkyl, S$(O_2)(C_1$-$C_6)$alkyl, and a mono or polycyclic $C_5$-$C_{12}$ aryl group;

$R_5$ is a hydrogen atom, a halogen atom, a cyano, $C_1$-$C_{10}$ alkyl, $C_3$-$C_{10}$ cycloalkyl, 3-to 8-membered heterocycle, $C_1$-$C_{10}$ alkoxy, $C_1$-$C_{10}$ haloalkoxy, $(C_1$-$C_6)$-alkoxy-$(C_1$-$C_6)$-alkyl, $(C_1$-$C_6)$-haloalkoxy-$(C_1$-$C_6)$-alkyl, $C_1$-$C_{10}$ thioalkyl, $(C_1$-$C_6)$-alkylthio-$(C_1$-$C_6)$-alkyl, $C_1$-$C_{10}$ alkylsulfinyl, $C_1$-$C_{10}$ haloalkylsulfinyl, $C_1$-$C_{10}$ haloalkylsulfonyl, $C_1$-$C_{10}$ alkylsulfonyl, $C_5$-$C_{12}$ arylsulfonyl, formyl, $C_2$-$C_{10}$ alkylcarbonyl, $C_2$-$C_{10}$ alkenyl, $C_2$-$C_{10}$ alkynyl, $C_2$-$C_{10}$ alkenyloxy, $C_2$-$C_{10}$ alkynyloxy, $C_2$-$C_{10}$ alkenylthio, $C_2$-$C_{10}$ alkynylthio, $C_1$-$C_{10}$ haloalkyl, $C_2$-$C_{10}$ haloalkenyl, $C_2$-$C_{10}$ haloalkynyl, $C_2$-$C_{10}$ haloalkylcarbonyl, $C_1$-$C_{10}$ haloalkylthio, $C_2$-$C_{10}$ haloalkenyloxy, $C_2$-$C_{10}$ haloalkynyloxy, $C_2$-$C_{10}$ haloalkenylthio, $C_2$-$C_{10}$ haloalkynylthio, $(C_5$-$C_{12})$-aryl-$(C_1$-$C_6)$-alkyl, $(C_5$-$C_{12})$-aryl-$(C_1$-$C_6)$-alkyl ester, a $(C_1$-$C_6)$alkyl-$(C_5$-$C_{12})$aryl, a $(C_1$-$C_6)$alkyl-$(C_5$-$C_{12})$heteroaryl, a $C_5$-$C_{12}$ aryl or a $C_3$-$C_{12}$ heteroaryl group, each group being optionally substituted with substituents independently selected from the group consisting of: halogen atoms, hydroxyl (OH), nitro, cyano, formyl, $C_3$-$C_7$ cycloalkyl, $C_1$-$C_6$-alkoxy, amino, $C_1$-$C_6$alkylamino, di$(C_1$-$C_6)$alkylamino, COOH, COO—$(C_1$-$C_6)$alkyl, $CONH_2$, CONH$(C_1$-$C_6)$alkyl, $C_1$-$C_6$ thioalkyl, SH, S$(C_1$-$C_6)$alkyl, S(O)$(C_1$-$C_6)$alkyl, S$(O_2)(C_1$-$C_6)$alkyl, and a mono or polycyclic $C_5$-$C_{12}$ aryl group;

Linker is a covalent linking group or a bond; and

Antibio is an antibiotic.

13. The compound as defined in claim 1 wherein said compound is an inhibitor of a carbapenemase enzyme.

14. The compound according to claim 13, wherein said compound is in combination with an antibiotic.

15. A pharmaceutical composition comprising at least one compound of formula (I) as defined in claim 1 and a pharmaceutically acceptable carrier.

16. The pharmaceutical composition of claim 15, further comprising an antibiotic.

17. A drug comprising a compound of formula (I) as defined in claim 1.

18. The drug according to claim 17, wherein the drug is an antibiotic.

19. The compound according to claim 14, wherein the antibiotic is a specific antibiotic for gram-negative bacteria.

20. A kit comprising:
- at least one first container containing a first therapeutically active compound of formula (I) as defined in claim 1, and
- at least one second container containing a second therapeutically active substance which is an antibiotic, as a combination product for simultaneous, sequential, or separate use.

21. The compound according to claim 13, wherein the carbapenemase enzyme is selected from the group consisting of class A enzyme, a class B enzyme, and a class D enzyme.

22. The compound according to claim 13 wherein the carbapenemase enzyme is selected from the group consisting of a NDM-1 type enzyme, OXA-48 type enzyme, and a KPC-type enzyme.

23. A kit comprising:
- at least one first container containing a first therapeutically active compound of at least a compound of formula (I') or at least one conjugate of formula (IV) as defined in claim 12, and
- at least one second container containing a second therapeutically active substance which is an antibiotic,
- as a combination product for simultaneous, sequential, or separate use.

* * * * *